US007393657B2

(12) United States Patent
Diss et al.

(10) Patent No.: US 7,393,657 B2
(45) Date of Patent: Jul. 1, 2008

(54) DIAGNOSIS AND TREATMENT OF CANCER: I

(75) Inventors: James K. J. Diss, London (GB); Raoul C. Coombes, London (GB); Mustafa B. A. Djamgoz, London (GB); Scott P. Fraser, London (GB)

(73) Assignee: Imperial College Innovations Limited, London (GB)

( * ) Notice: Subject to any disclaimer, the term of this patent is extended or adjusted under 35 U.S.C. 154(b) by 390 days.

(21) Appl. No.: 10/474,778

(22) PCT Filed: Apr. 11, 2002

(86) PCT No.: PCT/GB02/01692

§ 371 (c)(1),
(2), (4) Date: Mar. 4, 2004

(87) PCT Pub. No.: WO02/083945

PCT Pub. Date: Oct. 24, 2002

(65) Prior Publication Data

US 2004/0146877 A1 Jul. 29, 2004

Related U.S. Application Data

(60) Provisional application No. 60/283,295, filed on Apr. 12, 2001.

(51) Int. Cl.
*G01N 33/574* (2006.01)
*G01N 33/53* (2006.01)
*C12Q 1/68* (2006.01)

(52) U.S. Cl. .............................. 435/7.23; 435/6; 435/7.1

(58) Field of Classification Search ........................ None
See application file for complete search history.

(56) References Cited

U.S. PATENT DOCUMENTS

| 5,599,673 A | 2/1997 | Keating et al. |
| 2006/0166194 A1* | 7/2006 | Djamgoz et al. ............... 435/6 |

FOREIGN PATENT DOCUMENTS

WO    WO 02/18637    3/2002

OTHER PUBLICATIONS

Lee et al, J Cell Biochem, 1997, 65:513-526.*
Tockman et al., Cancer Res., 1992, 52:2711s-2718s.*
Greenbaum et al., Genome Biology, 2003, vol. 4, Issue 9, pp. 117.1-117.8.*
Diss et al, FEBS Letters, *Expression of Skeletal Muscle-Type Voltage-gated $Na^+$ Channel in rat and Human Prostate Cancer Cell Lines*, vol. 427, (1998), pp. 5-10.
Fletcher et al, Anesthesiology, *Sodium Channel in Human Malignant Hyperthermia*, vol. 86, (1997), pp. 1023-1032.
Grant et al, American Journal of Medicine, *Molecular Biology of Sodium Channels and Their Role in Cardiac Arrhythmias*, vol. 110, (2001), pp. 296-305.
Grimes et al, FEBS Letters, *Differential Expression of Voltage-Activated $Na^+$ Currents in two Prostatic Tumour Cell Lines: Contribution to Invasiveness* in Vitro, vol. 369, (1995), pp. 290-294.
Laniado et al, American Journal of Path, *Expression and Functional Analysis of Voltage-Activated $Na^+$ Channels in Human Prostate Cancer Cell Lines and Their Contribution to Invasion* in Vitro, vol. 4, (1997), pp. 1213-1221.
Smith et al, FEBS Letters, *Sodium Channel Protein Expression Enhances the Invasiveness of Rat and Human Prostate Cancer Cells*, vol. 423, (1998), pp. 19-24.
Akopian et al, FEBS Letters, *Structure and Distribution of a Broadly Expressed Atypical Sodium Channel*, vol. 400, (1997), pp. 183-187.
Alekov et al, Journal of Physiology, *A Sodium Channel Mutation Cuasing Epilepsy in Man Exhibits Subtle Defects in Fast Inactivation and Activation* in Vitro, vol. 529, (2000), pp. 533-539.
Bartolomei et al, Journal of Neurocytology, *Changes in the mRNAs Encoding Subtypes I, II and III Sodium Channel Alpha Subunits Following Kainate-Induced Seizures in Rat Brain*, vol. 26, (1997), pp. 667-678.
Beckers et al, Genomics, *A New Sodium Channel α-Subunit Gene (Scn9a) from Schwann Cells Maps to the Scn1a, Scn2a, Scn3a Cluster of Mouse Chromosome 2*, vol. 36, (1997), pp. 202-205.
Belcher et al, Proc. Natl. Academy Science USA, *Cloning of a Sodium Channel α Subunit from Rabbit Schwann Cells*, vol. 92, (1995), pp. 11034-11038.
Black and Waxman, Develop Neurosci, *Sodium Channel Expression: A Dynamic Process in Neurons and Non-Neuronal Cells*, vol. 18, (1996), pp. 139-152.
Black et al, Mol Brain Res, *Spinal Sensory Neurons Express Multiple Sodium Channel α-Subunit mRNAs*, vol. 43, (1996), pp. 117-131.
Black et al, GLIA, *Glial Cells Have Heart: rH1 $Na^+$ Channel mRNA and Protein in Spinal Cord Astrocytes*, vol. 3, (1998), pp. 200-208.

(Continued)

*Primary Examiner*—Misook Yu
*Assistant Examiner*—Mark Halvorson
(74) *Attorney, Agent, or Firm*—Nikolai & Mersereau, P.A.; C. G. Mersereau

(57) ABSTRACT

A method of diagnosing cancer comprising the steps of (i) obtaining a sample containing nucleic acid and/or protein from the patient; and (ii) determining whether the sample contains a level of SCN5A (and optionally also SCN9A) voltage-gated Na+ channel nucleic acid or protein associated with cancer. A method of diagnosing breast cancer comprising the steps of (i) obtaining a sample containing nucleic acid and/or protein from the patient; and (ii) determining whether the sample contains a level of voltage-gated Na+ channel nucleic acid or protein, preferably SCN5A or 5CN9A, associated with cancer. A method of treating cancer comprising the step of administering to the patient an agent which selectively prevents the function of SCN5A (and optionally also SCN9A) voltage-gated Na+ channel. A method of treating breast cancer comprising the step of administering to the patient an agent which selectively prevents the function of a voltage-gated Na+ channel, preferably SCN5A or 5CN9A. Genetic constructs and molecules useful in such methods. The methods and compositions are particularly suited to breast cancer.

9 Claims, 7 Drawing Sheets

OTHER PUBLICATIONS

Figure 1:
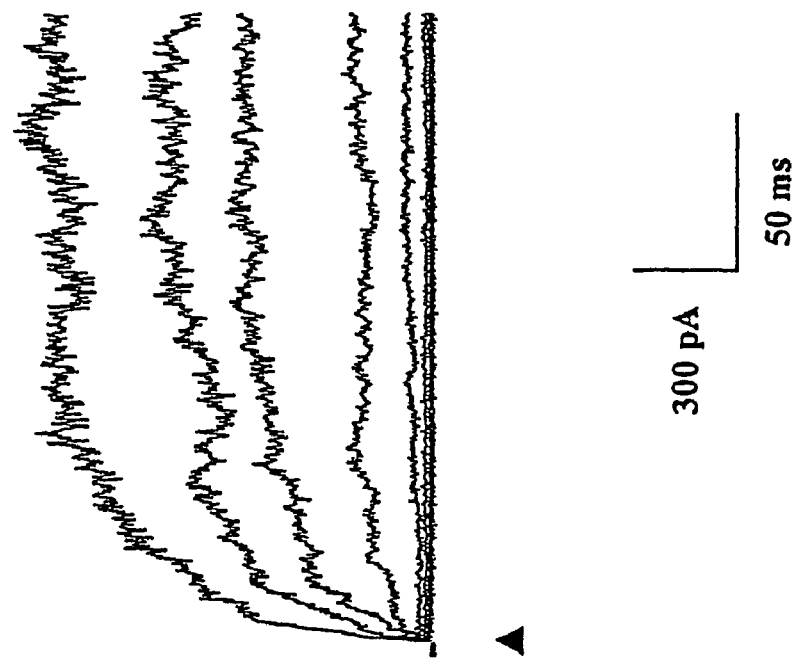
Figure 1:
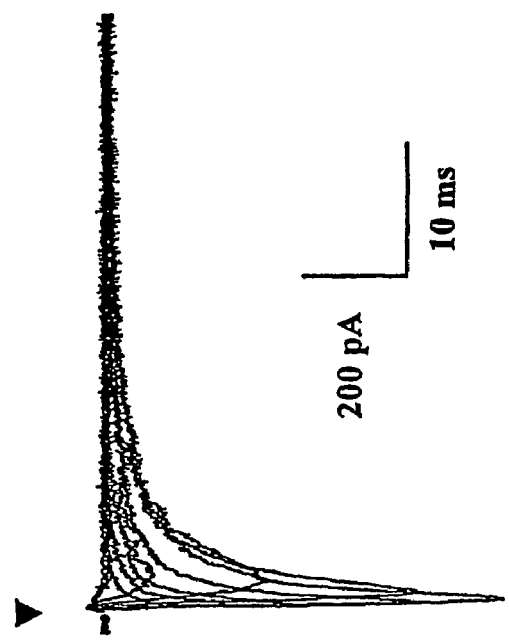
Figure 1:
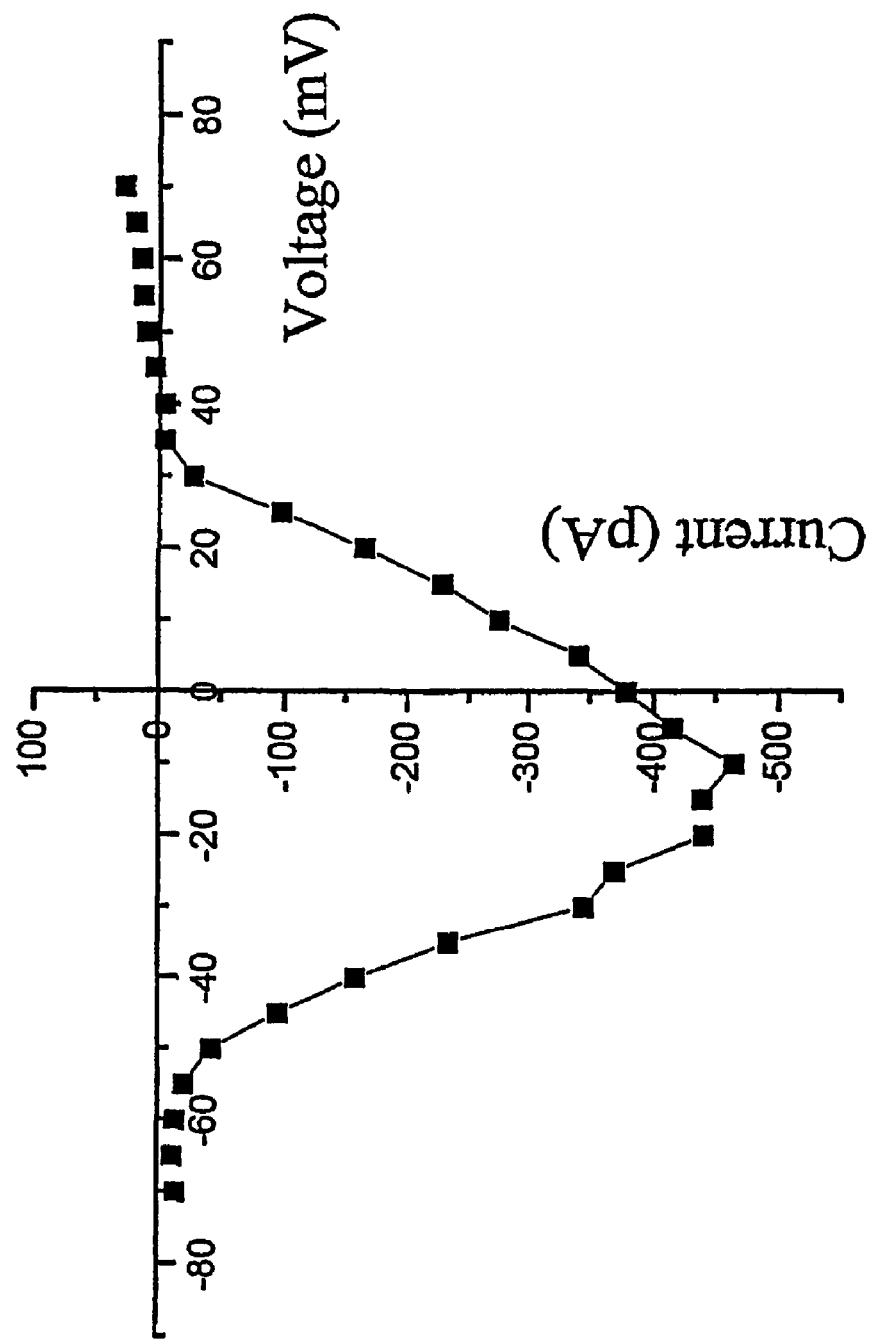

Black et al, Mol Brain Res, *Sodium Channel mRNAs in Cultured Spinal Cord Astrocytes: in situ Hybridization in Identified Cell Types*, vol. 23, (1994), pp. 235-245.

Blandino et al, Membrane Biol, *Voltage-Dependent Sodium Channels in Human Small-Cell Lung Cancer Cells: Role in Action Potentials and Inhibition by Lambert-Eaton Syndrome IgG*, vol. 143, (1995), pp. 153-163.

Bonhaus et al, Neuropharmacol, *The β1 Sodium Channel Subunit Modifies the Interactions of Neurotoxins and Local Anesthetics with the Rat Brain IIA α Sodium Channel in Isolated Membranes but not in Intact Cells*, vol. 35, (1996), pp. 605-613.

Bullman, Hum Mol Genet, *Phenotype Variation and Newcomers in Ion Channel Disorders*, vol. 6, (1997), pp. 1679-1685.

Burgess et al, Nature Genet, *Mutation of a New Sodium Channel Gene, Scn8a, in the Mouse Mutant 'Motor Endplate Disease'*, vol. 10, (1995), pp. 461-465.

Cannon, Mol Neurology (JB Martin, ED) Scientific American Inc., NY, *Ion Channel Defects in the Hereditary Myotonias and Periodic Paralyses*, (1998), pp. 257-277.

Cannon et al, Pflugers Arch, *Modification of the $Na^+$ Current Conducted by the Rat Skeletal Muscle α Subunit by Coexpression with a Human β Subunit*, vol. 423, (1993), pp. 155-157.

Catalano and Shatz, Science, *Activity-Dependent Cortical Target Selection by Thalamic Axons*, vol. 281, (1998), pp. 559-562.

Catterall, Neuron, *Review from Ionic Currents to Molecular Mechanisms: The Structure and Function of Voltage-Gated Sodium Channels*, vol. 26, (2000), pp. 13-25.

Catterall, Ann Rev Biochem, *Molecular Properties of Voltage-Sensitive Sodium Channels*, vol. 55, (1986), pp. 953-985.

Cohen and Levitt, Circ Rec, *Partial Characterization of the rH1 Sodium Channel Protein From Rat Heart Using Subtype-Specific Antibodies*, vol. 73, (1993), pp. 735-742.

Cushman et al, Thromb Vasc Biol, *Tamoxifen and Cardiac Risk Factors in Healthy Women*, vol. 21, (2001), pp. 255-261.

Cuzick et al, The Lancet, *Electropotential Measurements as a New Diagnostic Modality for Breast Cancer*, vol. 352, (1998), pp. 359-363.

Dawes et al, Visual Neuroscience, *Identification of Sodium Channel Subtypes Induced in Cultured Retinal Pigment Epithelium Cells*, vol. 12, (1995), pp. 1001-1005.

Dib-Hajj et al, Proc Natl Acad Sci USA, *NaN, a Novel Voltage-Gated Na Channel, is expressed Preferentially in Peripheral Sensory Neurons and Down-regulated After Axotomy*, vol. 95, (1998), pp. 8963-8968.

Dib-Hajj et al, Proc Natl Acad Sci USA, *Down-Regulation of Transcripts for Na Channel α-SNS in Spinal Sensory Neurons Following Axotomy*, vol. 93, (1996), pp. 14950-14954.

Dib-Hajj et al, FEBS Letters, *Sodium Channel in mRNA in the B104 Neuroblastoma Cell Line*, vol. 384, (1996), pp. 78-82.

Dib-Hajj et al, Journal of Neurophysiology, *Rescue of α-SNS Sodium Channel Expression in Small Dorsal Root Ganglion Neurons After Axotomy by Nerve Growth Factor in Vivo*, vol. 79, (1998), pp. 2668-2676.

Dib-Hajj et al, Genomics, *Coding Sequence, Genomic Organization, and Conserved Chromosomal Localization of the Mouse Gene Scn11a Encoding the Sodium Channel NaN*, vol. 59, (1999), pp. 309-318.

Diss et al, Prostate, *Expression Profiles of Voltage-Gated $Na^+$ Channel α-Subunit Genes in Rat and Human Prostate Cancer Cell Lines*, vol. 48, (2001), pp. 165-178.

Diss et al, FEBS Letters, *Expression of Skeletal Muscle-Type Voltage-Gated $Na^+$ Channel in Rat and Human Prostate Cancer Cell Lines*, vol. 427, (1998), pp. 5-10.

Donahue et al, Devel Biol, *Segregation of $Na^+$-Channel Gene Expression During Neuronal-Glial Branching of a Rat PNS-Derived Stem Cell Line, RT4-AC*, vol. 147, (1991), pp. 415-424.

Fjell et al, Mol. Brain Res, *Differential Role of GDNF and NGF in the Maintenance of Two TTX-Resistance Sodium Channels in Adult DRG Neurons*, vol. 67, (1999), pp. 267-282.

Fozzard and Hanck, Physiological Rev, *Structure and Function of Voltage-Dependent Sodium Channels: Comparison of Brain II and Cardiac Isoforms*, vol. 76, (1996), pp. 887-926.

Fraser et al, J Physio, *Voltage-Gated $Na^+$ Channel Activity Contributes to Rodent Prostate Cancer Cell Migration* in Vitro, (1998), pp. 513P, 131P.

Fraser et al, Cell Tissue Res; *Tetrodotoxin Suppresses Morphological Enhancement of the Metastatic MAT-LyLu Rat Prostate Cancer Cell Line*, vol. 295, (1999), pp. 505-512.

Gellens et al, Proc Natl Acad Sci USA, *Primary Structure and Functional Expression of the Human Cardiac Tetradotoxin-Insensitive Voltage-Dependent Sodium Channel*, vol. 89, (1992), pp. 554-558.

GenBank Accession No. AB027567.
GenBank Accession No. M77235.
GenBank Accession No. AJ276141.
GenBank Accession No. AJ276142.
GenBank Accession No. AJ310882.
GenBank Accession No. AJ310883.
GenBank Accession No. AJ310884.
GenBank Accession No. AJ310885.
GenBank Accession No. AJ310886.
GenBank Accession No. AJ310887.
GenBank Accession No. AJ310888.
GenBank Accession No. AJ310889.
GenBank Accession No. AJ310890.
GenBank Accession No. AJ310891.
GenBank Accession No. AJ310892.
GenBank Accession No. AJ310893.
GenBank Accession No. AJ310894.
GenBank Accession No. AJ310895.
GenBank Accession No. AJ310896.
GenBank Accession No. AJ310897.
GenBank Accession No. AJ310898.
GenBank Accession No. AJ310899.
GenBank Accession No. AJ310900.
GenBank Accession No. X82835.

George et al, Genomics, *Genomic Organization of the Human Skeletal Muscle Sodium Channel Gene*, vol. 15, (1993), pp. 598-606.

George et al, Genomics, *Assignment of a Human Voltage-Dependent Sodium Channel α-Subunit Gene (SCN6A) to 2Q21-Q23*, vol. 19, (1994), pp. 395-397).

George et al, Proc Natl Acad Sci USA, *Molecular Cloning of an Atypical Voltage-Gated Sodium Channel Expressed in Human Heart and Uterus: Evidence for a Distinct Gene Family*, vol. 89, (1992), pp. 4893-4897.

Goldin, Ann Rev Physiol, *Resurgence of Sodium Channel Research*, vol. 63, (2001), pp. 871-894.

Goldin et al, Proc Natl Acad Sci USA, *Messenger RNA Coding for only the α Subunit of the Rat Brain Na Channel is Sufficient for Expression of Functional Channels in Xenopus Oocytes*, vol. 83, (1986), pp. 7503-7507.

Grimes and Djamgoz, J Cell Physiol, *Electrophysiological Characterization of Voltage-Gated $Na^+$ Current Expressed in the Highly Metastitic Mat-Lylu Cell Line of Rat Prostate Cancer*, vol. 175, (1998), pp. 50-58.

Grimes et al, FEBS Letters, *Differential Expression of Voltage-Activated $Na^+$ Currents in Two Prostatic Tumour Cell Lines: Contribution to Invasiveness* in Vitro, vol. 369, (1995), pp. 290-294.

Gu et al, J Neurophysiol, *TTX-Sensitive and -Resistant $Na^+$ Currents and mRNA for the TTX-Resistant rH1 Channel, Are Expressed in B104 Neuroblastoma Cells*, vol. 77, (1997), pp. 236-246.

Hardy et al, FEBS Letters, *Inhibition of Voltage-Gated Cationic Channels in Rat Embryonic Hypothalamic Neurones and C1300 Neuroblastoma Cells by Triphenylethylene Antioestrogens*, vol. 434, (1998), pp. 236-240.

Isom et al, Science, *Primary Structure and Functional Expression of the $β_1$ Subunit of the Rat Brain Sodium Channel*, vol. 256, (1992), pp. 839-842.

Isom et al, Cell, *Structure and Function of the β2 Subunit of Brain Sodium Channels, a Transmembrane Glycoprotein with a CAM Motif*, vol. 83, (1995), pp. 433-442.

Jeong et al, Biochem Biophys Res Commun, *Identification of a Novel Human Voltage-Gated Sodium Channel α Subunit Gene, SCN12A*, vol. 267, (2000), pp. 262-270.

Jongsma, Curr Biol, *Sudden Cardiac Death: A Matter of Faulty Ion Channels?*, vol. 8, (1998), pp. R568-R571.

Kallen et al, Neuron, *Primary Structure and Expression of a Sodium Channel Characteristic of Denervated and Immature Rat Skeletal Muscle*, vol. 4, (1990), pp. 233-242.

Kanazirska et al, Biochem Biophys Res Comm, *Voltage-Dependent Effect of $Al^{3+}$ on Channel Activities in Hippocampal Neurons*, vol. 232, (1997), pp. 84-87.

Kayano et al, FEBS Letters, *Primary Structure of Rat Brain Sodium Channel III Deducted from the cDNA Sequence*, vol. 228, (1988), pp. 187-194.

Klugbauer et al, EMBO J, *Structure and Functional Expression of a New Member of the Tetradotoxin-Sensitive Voltage-Activated Sodium Channel Family From Human Neuroendocrine Cells*, (1995), pp. 1084-1090.

Loughey et al, Cell, *Molecular Analysis of the Para Locus, a Sodium Channel Gene in Drosophila*, vol. 58, (1989), pp. 1143-1154.

Malo et al, Cytogen Cell Genet, *Localization of a Putative Human Brain Sodium Channel Gene (SCN1A) to Chromosome Band 2q24*, vol. 67, (1994), pp. 178-186.

Malo et al, Proc Natl Acad Sci USA, *Targeted Gene Walking by Low Stringency Polymerase Chain Reaction: Assignment of a Putative Human Brain Sodium Channel Gene (SCN3A) to Chromosome 2q24-31*, vol. 91, (1994), pp. 2975-2979.

Marban et al, J Physiol, *Structure and Function of Voltage-Gated Sodium Channels*, vol. 508, (1998), pp. 647-657.

Morgan et al, Proc Natl Acad Sci USA, *β3: An Additional Auxiliary Subunit of the Voltage-Sensitive Sodium Channel that Modulates Channel Gating with Distinct Kinetics*, vol. 97, (2000), pp. 2308-2313.

Mycielska et al, J Cell Physiol, *Contributions of Functional Voltage-Gated $Na^+$ Channel Expression to Cell Behaviors Involved in the Metastatic Cascade in Rat Prostate Cancer: II. Secretory Membrane Activity*, vol. 195, (2003), pp. 461-469.

Noda et al, Nature, *Expression of Functional Sodium Channels from Cloned cDNA*, vol. 322, (1986), pp. 826-828.

Oh and Waxman, Neuroreport, *Novel Splice Variants of the Voltage-Sensitive Sodium Channel Alpha Subunit*, vol. 9, (1998), pp. 1267-1271.

Patt et al, Neurosci, *Neuron-like Physiological Properties of Cells from Human Oligodendroglial Tumors*, vol. 71, (1996), pp. 601-611.

Patt et al, Brain Pathol, *Influence of Voltage-Activated Sodium Channels on Growth and Motility of Human Neuroblastoma Cells* in Vitro, vol. 10, (2000), pp. 738.

Penn et al, Science, *Competition in Retinogeniculate Patterning Driven by Spontaneous Activity*, vol. 279, (1988), pp. 2108-2112.

Plummer and Meisler, Genomics, *Evolution and Diversity of Mammalian Sodium Channel Genes*, vol. 57, (1998), pp. 323-331.

Plummer et al, J Biol Chem, *Alternative Splicing of the Sodium Channel SCN8A Predicts a Truncated Two-Domain Protein in Fetal Brain and Non-Neuronal Cells*, vol. 272, (1997), pp. 24008-24015.

Plummer et al, Genomics, *Exon Organization, Coding Sequence, Physical Mapping, and Polymorphic Intragenic Markers for the Human Neuronal Sodium Channel Gene SCN8A*, vol. 54, (1998), pp. 287-296.

Rich et al, Neurobiol. Dis, *Altered Gene Expression in Steriod-Treated Denervated Muscle*, vol. 6, (1999), pp. 515-522.

Rodriguez et al, Epidemiology, *Family History of Breast Cancer as a Predictor for Fatal Prostate*, vol. 9, (1998), pp. 525-529.

Rogart et al, Proc Natl Acad Sci USA, *Molecular Cloning of a Putative Tetrodotoxin-Resistant Rat Heart $Na^+$ Channel Isoform*, vol. 86, (1989), pp. 8170-8174.

Sangameswaren et al, J Biol Chem, *A Novel Tetrodotoxin-Sensitive, Voltage-Gated Sodium Channel Expressed in Rat and Human Dorsal Root Ganglia*, vol. 272, (1997), pp. 14805-14809.

Santana et al, Science *$Ca^{2+}$ Flux Through Promiscuous Cardiac $Na^+$ Channels: Slip-Mode Conductance*, vol. 279, (1998), pp. 1027-1033.

Schlief et al, Eur Biophys, *Pore Properties of Rat Brain II Sodium Channels Mutated in the Selectivity Filter Domain*, vol. 25, (1996), pp. 75-91.

Shatz, Neuron, *Impulse Activity and the Patterning of Connections During CNS Development*, vol. 5, (1990), pp. 745-756.

Skaper et al, FASEB J, *Melatonin Prevents the Delayed Death of* , vol. 12, (1998), pp. 725-731.

Smith et al, FEBS Letters, *Sodium Channel Protein Expression Enhances the Invasiveness of Rat and Human Prostate Cancer Cells*, vol. 423, (1998), pp. 19-24.

Souslova et al, Genomics, *Cloning and Characterization of a Mouse Sensory Neuron Tetrodotoxim-Resistant Voltage-Gated Sodium Channel Gene, Scn10a*, vol. 41, (1997), pp. 201-209.

Tanaka et al, Neuroreport, *SNS $Na^+$ Channel Expression Increases in Dorsal Root Ganglion Neurons in the Carrageenan Inflammatory Pain Model*, vol. 9, (1998), pp. 967-972.

Toledo-Aral et al, Proc Natl Acad Sci USA, *Identification of PN1, a Predominant Voltage-Dependent Sodium Channel Expressed Principally in Peripheral Neurons*, vol. 94, (1997), pp. 1527-1532.

Wang et al, Genomics, *Genomic Organization of the Human SCN5A Gene Encoding the Cardiac Sodium Channel*, vol. 34, (1996), pp. 9-16.

Wang et al, Biophys J, *Comparison of Heterologously Expressed Human Cardiac and Skeletal Muscle Sodium Channels*, vol. 70, (1996), pp. 238-245.

White et al, Mol Pharmacol, *SkM2, a $Na^+$ Channel cDNA Clone from Denervated Skeletal Muscle, Encodes a Tetrodotoxin-Insensitive $Na^+$ Channel*, vol. 39, (1991), pp. 604-608.

Yang et al, Neuron, *TTX-Sensitive and TTX-Insensitive Sodium Channel mRNA Transcripts ARe Independently Regulated in Adult Skeletal Muscle After Denervation*, vol. 7, (1991), pp. 421-427.

Zeng et al, Am J Physiol, *Cardiac Sodium Channels Expressed in a Peripheral Neurotumor-Derived Cell Line, RT4-B8*, vol. 39, (1996), pp. C1522-C1531.

Zhang et al, Invasion Metastasis, *Relative Malignant Potential of Human Breast Carcinoma Cell Lines Established from Pleural Effusions and a Brain Metastisis*, vol. 11, (1991), pp. 204-215.

Zhou and Hoffman, J Biol Chem, *Pathophysiology of Sodium Channelopathies*, vol. 269, (1994), pp. 18563-18571.

* cited by examiner

DIAGNOSIS AND TREATMENT OF CANCER: I

The present invention relates to methods of determining whether a patient has cancer and whether the cancer is likely to metastasise; and it relates to methods of treating cancer, particularly breast cancer.

Cancer is a serious disease and a major killer. Although there have been advances in the diagnosis and treatment of certain cancers in recent years, there is still a need for improvements in diagnosis and treatment.

Cancer is a genetic disease and in most cases involves mutations in one or more genes. There are believed to be around 40,000 genes in the human genome but only a handful of these genes have been shown to be involved in cancer. Although it is surmised that many more genes than have been presently identified will be found to be involved in cancer, progress in this area has remained slow despite the availability of molecular analytical techniques. This may be due to the varied structure and function of genes which have been identified to date which suggests that cancer genes can take many forms, occur in different combinations and have many different functions.

Breast cancer is one of the most significant diseases that affects women. At the current rate, American women have a 1 in 8 risk of developing cancer by the age of 95 (American Cancer Society, Cancer Facts and Figures, 1992, American Cancer Society, Atlanta, Ga., USA). Genetic factors contribute to an ill-defined proportion of breast cancer cases, estimated to be about 5% of all cases but approximately 25% of cases diagnosed before the age of 40 (Claus et al (1991) *Am J. Hum. Genet.* 48, 232-242). Breast cancer has been divided into two types, early-age onset and late stage onset, based on an inflection in the age-specific incidence curve at around the age of 50. Mutation of one gene, BRCA1, is thought to account for approximately 45% of familial breast cancer, but at least 80% of families with both breast and ovarian cancer (Easton et al (1993) *Am. J. Hum. Genet.* 52, 678-701).

Breast carcinoma is potentially curable only when truly localised. The most common problem is either late presentation with overt metastases or, more frequently, the development of systemic metastases after apparent local cure. Metastatic breast carcinoma is highly chemosensitive and effective chemotherapy routinely induces disease remission, allowing delay in the onset of secondary disease or amelioration of the symptoms of extensive disease.

Recently, the role of tumour-associated antigens in the biology of cancer has begun to be investigated. Probably the best studied example of tumour-associated antigens are the MAGE antigens which are involved in melanoma and certain other cancers, such as breast cancer. Therapeutic and diagnostic approaches making use of the MAGE antigens are described in Gattoni-Celli & Cole (1996) *Seminars in Oncology* 23, 754-758, Itoh et al (1996) *J. Biochem.* 119, 385-390, WO 92/20356, WO 94/23031, WO 94/05304, WO 95/20974 and WO 95/23874. However, other tumour-associated antigens have also been implicated in breast cancer. For example, studies concerning the antigens expressed by breast cancer cells, and in particular how these relate to the antigenic profile of the normal mammary epithelial cell, have been and continue to be a major activity in breast cancer research. The role of certain antigens in breast cancer, especially the role of polymorphic epithelial mucin (PEM; the product of the MUC1 gene) and the c-erbB2 protooncogene, are reviewed in Taylor-Papadimitriou et al (1993) *Annals NY Acad. Sci.* 698, 3147. Other breast cancer associated antigens include MAGE-1 and CEA.

Immunotherapeutic strategies and vaccines involving the MUC1 gene or PEM are described in Burchell et al (1996), pp 309-313, In Breast Cancer, Advances in Biology and Therapeutics, Calvo et al (eds), John Libbey Eurotext; Graham et al (1996) *Int. J. Cancer* 65, 664-670; Graham et al (1995) *Tumor Targeting* 1, 211-221; Finn et al (1995) *Immunol. Rev.* 145, 61-89; Burchell et al (1993) *Cancer Surveys* 18, 135-148; Scholl & Pouillart (1997) *Bull. Cancer* 84, 61-64; and Zhang et al (1996) *Cancer Res.* 56, 3315-3319.

Despite the recent interest in the breast cancer predisposing genes, BRCA1 and BRCA2, there remains the need for further information on breast cancer, and the need for further diagnostic markers and targets for therapeutic intervention.

For cancers such as breast cancer, present screening methods are therefore unsatisfactory; there is no reliable method for diagnosing the cancer, or predicting or preventing its possible metastatic spread, which is the main cause of death for most patients.

Grimes et al (1995) *FEBS Lett.* 369, 290-294 describes the differential expression of voltage-gated $Na^+$ currents in two prostatic tumour cell lines and discusses their contribution to invasiveness in vitro. The cell lines studied were rat cell lines and there is no indication of which particular voltage-gated $Na^+$ channels may be involved.

Laniado et al (1997) *Am J. Pathol.* 150, 1213-1221 describes the expression and functional analysis of voltage-gated $Na^+$ channels in human prostate cancer cell lines and discusses their contribution to invasion in vitro. There is no indication of which particular voltage-gated $Na^+$ channels may be involved.

Smith et al (1998) *FEBS Lett.* 423, 19-24 suggests that $Na^+$ channel protein expression enhances the invasiveness of rat and human prostate cancer cell lines.

Grimes & Djamgoz (1998) *J. Cell. Physiol.* 175, 50-58 describes the electrophysiological and pharmacological characterisation of voltage-gated $Na^+$ current expressed in the highly metastatic Mat-LyLu cell line of rat prostate cancer. The underlying VGSC is identified as belonging to the "tetrodotoxin-sensitive" class.

Dawes et al (1995) *Visual Neuroscience* 12, 1001-1005 describes the identification of voltage-gated $Na^+$ channel subtypes induced in cultured retinal pigment epithelium cells.

UK Patent application No 0021617.6 entitled "Diagnosis and treatment of cancer" filed on 2 Sep. 2000 relates to methods of treatment and diagnosis of cancer, particularly prostate cancer concerning expression of VGSCs. VGSC expression correlates with pathological progression and a VGSC which is associated with human cancer, particularly prostate cancer and its metastases, is hNe—Na (SCN9A). The amino acid sequence of the protein, and cDNA of the mRNA encoding it is known (Klugbauer et al (1995) *EMBO J.* 14, 1084-1090).

Reviews of voltage-gated $Na^+$ channels may be found in, for example, Black & Waxman (1996) *Develop. Neurosci.* 18, 139-152; Fozzard & Hanck (1996) *Physiol. Rev.* 76, 887-926; Bullman (1997) *Hum. Mol. Genet.* 6, 1679-1685; Cannon (1999); Marban et al (1998) *J. Physiol.* 508, 647-657; Catterall (2000) *Neuron* 26, 13-25; Plummer & Meisler (1999) *Genomics* 57, 323-331, and Goldin (2001) *Ann Rev Physiol* 63, 871-894. Some $Na^+$ and other ion channels are well known to underly certain genetic defects as is described in Bullman (1997) *Hum. Mol. Genet.* 6, 1679-1685; Burgess et al (1995) *Nature Genet.* 10, 461-465; and Cannon (1998) *Mol Neurology* (J B Martin, Ed) Scientific American Inc., NY.

The involvement of VGSCs in breast cancer has not been demonstrated, and the particular VGSC(s) involved in human breast cancer have not been identified.

We have now found, surprisingly, that VGSC expression correlates with pathological progression and that VGSCs which are associated with human cancer, particularly breast cancer and its metastases, are SCN5A, SCN8A and SCN9A, particularly SCN5A (also termed h1, SkM2 and $Na_v1.5$). These are known VGSCs (although for SCN5A and SCN8A not previously known to be associated with human cancer, in particular human breast cancer) and amino acid sequences of the proteins, and cDNA of the mRNA encoding them have been reported (SCN9A: Klugbauer et al (1995) *EMBO J.* 14, 1084-1090, GenBank Accession No. X82835; SCN5A: Gellens et al (1992) Proc. Natl. Acad. Sci. U.S.A. 89 (2), 554-558, GenBank Accession No. M77235; SCN8A: GenBank Accession No. AB027567). Splice variants (for example neonatal splice variants; discussed further below) and other variants of the reported SCN5A, SCN8A and SCN9A are included by the terms SCN5A, SCN8A and SCN9A. For example, sequences determined in the present work are included and particularly preferred, and are discussed in Example 1.

The chromosomal location of SCN9A (also termed hNe—Na (human) and PN1 (rat), and recently $Na_v1.7$) has not yet been determined. However, the mouse equivalent has been located to the voltage-gated $Na^+$ channel cluster on mouse chromosome 2 (Beckers et al (1997) *Genomics* 36, 202-205). This cluster is also present in human chromosome 2 where SCN9A may similarly be present (Malo et al (1994) *Cytogen. Cell. Genet.* 67, 178-186; Malo et al (1994) *Proc. Natl. Acad. Sci. USA* 91, 2975-2979; George et al (1994) *Genomics* 19, 395-397). The hNe—Na gene (human SCN9A) intron/exon organisation has not yet been determined but could be inferred from other known, conserved VGSC intron positions, as reported in gene structure studies on SCN4A (George et al (1993) *Genomics* 15, 598-606), SCN5A (Wang et al (1996) *Genomics* 34, 9-16), SCN10A (Sonslova et al (1997) *Genomics* 41, 201-209) and the *Drosophila para* VGSC gene (Loughey et al (1989) *Cell* 58, 1143-1154).

The brain-type voltage-gated $Na^+$ channels (rat brain I-III (Noda et al (1986) *Nature* 322, 826-828; Kayano et al (1988) *FEBS Lett.* 228, 187-194) that are most similar to hNe—Na are 20% different over the whole sequence (human skeletal, 30%; heart 34% different). However, (i) if sequence comparison is made within specific structural/functional domains this homology is much reduced (eg first one-third of DII-DIII cytoplasmic linker region is only 45% homologous to the most similar channel (RBII/HBII); (ii) hNe—Na has sufficiently different regions (eg residues 446-460: EYTSIRRSRIMGLSE) to make specific antibodies (see, for example, Toledo-Aral et al (1997) *Proc. Natl. Acad. Sci. USA* 94, 1527-1532).

Subtype-specific antibodies for SCN5A are described in, for example, Cohen & Levitt (1993) *Circ Res* 73, 735-742.

SCN8A is most similar to the brain-type VGSCs, sharing 70% amino acid similarity (and approximately 60% similarity with other VGSCs). SCN5A shares 60% similarity with most VGSCs, including the brain types.

It is an object of the invention to provide methods useful in providing diagnoses and prognoses of cancer, especially breast cancer, and for aiding the clinician in the management of cancer, particularly breast cancer. In particular, an object of the invention is to provide a method of assessing the metastatic potential of cancer, in particular breast cancer.

Further objects of the invention include the provision of methods of treatment of cancer, in particular breast cancer, and methods of identifying compounds which selectively inhibit the VGSCs associated with human cancer, particularly breast cancer, since these may be useful in treating cancer.

A first aspect of the invention provides a method of determining the susceptibility of a human patient to cancer comprising the steps of (i) obtaining a sample containing nucleic acid and/or protein from the patient; and (ii) determining whether the sample contains a level of SCN5A voltage-gated $Na^+$ channel nucleic acid or protein associated with cancer.

A second aspect of the invention provides a method of diagnosing cancer in a human patient comprising the steps of (i) obtaining a sample containing nucleic acid and/or protein from the patient; and (ii) determining whether the sample contains a level of SCN5A voltage-gated $Na^+$ channel nucleic acid or protein associated with cancer.

It will be appreciated that determining whether the sample contains a level of SCN5A (or SCN9A in relation to the fourth and fifth aspects of the invention) VGSC nucleic acid or protein associated with cancer may in itself be diagnostic of cancer or it may be used by the clinician as an aid in reaching a diagnosis.

For example, in relation to breast cancer, it is useful if the clinician undertakes a histopathological examination of biopsy tissue or carries out external digital examination or carries out imaging. Clinical examination of breast cancer is done currently through morphological assessment of cells removed in a needle aspirate and also by mammography. Mammography is also dependent on morphological changes on the mammogram. There is currently no biochemical assessment which is used routinely to distinguish between cancer and non cancer in relation to breast cancer. Screening tests mentioned above relating to BRCA1 and BRCA2 may be used. It will be appreciated that the clinician will wish to take in to account these or other factors, as well as consider the level of a said VGSC, before making a diagnosis.

A third aspect of the invention provides a method of predicting the relative prospects of a particular outcome of a cancer in a human patient comprising the steps of (i) obtaining a sample containing nucleic acid and/or protein from the patient; and (ii) determining whether the sample contains a level of SCN5A voltage-gated $Na^+$ channel nucleic acid or protein associated with cancer.

A fourth aspect of the invention provides a method of determining the susceptibility of a human patient to breast cancer comprising the steps of (i) obtaining a sample containing nucleic acid and/or protein from the patient; and (ii) determining whether the sample contains a level of voltage-gated $Na^+$ channel nucleic acid or protein associated with cancer. Preferably the method comprises the step of determining whether the sample contains a level of SCN5A and/or SCN9A voltage-gated $Na^+$ channel nucleic acid or protein associated with cancer.

A fifth aspect of the invention provides a method of diagnosing breast cancer in a human patient comprising the steps of (i) obtaining a sample containing nucleic acid and/or protein from the patient; and (ii) determining whether the sample contains a level of voltage-gated $Na^+$ channel nucleic acid or protein associated with cancer. Preferably the method comprises the step of determining whether the sample contains a level of SCN5A and/or SCN9A voltage-gated $Na^+$ channel nucleic acid or protein associated with cancer.

A sixth aspect of the invention provides a method of predicting the relative prospects of a particular outcome of a breast cancer in a human patient comprising the steps of (i) obtaining a sample containing nucleic acid and/or protein from the patient; and (ii) determining whether the sample contains a level of voltage-gated $Na^+$ channel nucleic acid or protein associated with cancer. Preferably the method comprises the step of determining whether the sample contains a level of SCN5A and/or SCN9A voltage-gated $Na^+$ channel nucleic acid or protein associated with cancer. Thus, the method of the third or sixth aspect of the invention may be useful in prognosis or aiding prognosis. The method may be used as an adjunct to known prognostic methods such as histopathological examination of biopsy tissue, external digital examination or imaging.

It is preferred for each of the preceding aspects of the invention, particularly the third and sixth aspects, that the method comprises the step of determining whether the sample contains a level of SCN5A voltage-gated Na$^+$ channel nucleic acid or protein associated with cancer. The method may further comprise the step of determining whether the sample contains a level of SCN9A voltage-gated Na$^+$ channel nucleic acid or protein associated with cancer.

It will be appreciated that determination of the level of a said VGSC (including determination of the level of more than one, for example two said VGSCs) in the sample will be useful to the clinician in determining how to manage the cancer in the patient. For example, since elevated levels of a said VGSC, particularly SCN5A, are associated with metastatic potential, particularly in a breast cancer, the clinician may use the information concerning the levels of the said VGSC(s) to facilitate decision making regarding treatment of the patient. Thus, if the level of said VGSC (preferably SCN5A) is indicative of a low metastatic potential of the cancer, preferably a breast cancer, unnecessary radical surgery may be avoided. Similarly, if the level of said VGSC is indicative of a high metastatic potential of said cancer, preferably breast cancer, radical surgery (ie mastectomy) may be the preferred treatment. Even if it is not appropriate to alter the type of surgery carried out, determining whether the level of said VGSC is indicative of a high metastatic potential may help the clinician decide whether the patient needs adjuvant systemic treatment or not. At present, a major aim in oncology is to be able to distinguish those breast cancers with a high metastatic potential from those with a low metastatic potential, because those with a low metastatic potential should not need to be put through six months of very toxic chemotherapy treatment.

It will be appreciated from the foregoing, and from the Examples below, that the determination of the levels of the said VGSC(s), preferably SCN5A, may be exploited diagnostically to predict whether a given cancer, particularly breast cancer, would metastasise since expression of said VGSC, preferably SCN5A, is believed to correspond to possible future spread of a tumour.

It is particularly preferred if the cancer under consideration is breast cancer. Other appropriate cancers may include prostate cancer, small cell carcinoma of the lung and glioma (brain cancer).

It is also particularly preferred if the method of the invention is employed to predict whether a given breast cancer would metastasise.

The level of said VGSC which is indicative of cancer or metastatic potential may be defined as the increased level present in known cancerous or metastatic breast cells (preferably epithelial cells but possibly also or alternatively other cell types such as neuroendocrine or myoepithelial cells) over known non-cancerous or non-metastatic breast cells. The level of said VGSC protein may be, for example, at least 1½ fold higher in cancerous cells or metastatic cells, or it may be at least 2-fold or 3-fold higher. Quantitative analysis by micro-densitometry of immunohistochemically processed tissue sections may be used. An antibody that is believed to react with all VGSCs may be used, possibly in combination with PCR analysis, which may be capable of distinguishing between VGSC types. The level of mRNA encoding said VGSC may be, for example, at least 1½ fold higher in cancerous cells or metastatic cells, or it may be at least 2-fold or 3-fold higher, or at least 10, 50, 100, 500, 1000, 1200, 1500 or 1800-fold higher. Measurements by semi-quantitative PCR indicates that the level of SCN5A mRNA is about 1800-fold higher in the highly metastatic cell lines than in the lowly-metastatic cell lines, as described in the Examples.

In one preferred embodiment of the invention it is determined whether the level of said VGSC (preferably SCN5A) nucleic acid, in particular mRNA, is a level associated with cancer or metastatic potential. Preferably, the sample contains nucleic acid, such as mRNA, and the level of said VGSC is measured by contacting said nucleic acid with a nucleic acid which hybridises selectively to said VGSC nucleic acid.

By "selectively hybridising" is meant that the nucleic acid has sufficient nucleotide sequence similarity with the said human nucleic acid that it can hybridise under moderately or highly stringent conditions. As is well known in the art, the stringency of nucleic acid hybridization depends on factors such as length of nucleic acid over which hybridisation occurs, degree of identity of the hybridizing sequences and on factors such as temperature, ionic strength and CG or AT content of the sequence. Thus, any nucleic acid which is capable of selectively hybridising as said is useful in the practice of the invention.

Nucleic acids which can selectively hybridise to the said human nucleic acid include nucleic acids which have >95% sequence identity, preferably those with >98%, more preferably those with >99% sequence identity, over at least a portion of the nucleic acid with the said human nucleic acid. As is well known, human genes usually contain introns such that, for example, a mRNA or cDNA derived from a gene would not match perfectly along its entire length with the said human genomic DNA but would nevertheless be a nucleic acid capable of selectively hybridising to the said human DNA. Thus, the invention specifically includes nucleic acids which selectively hybridise to said VGSC mRNA or cDNA but may not hybridise to a said VGSC gene. For example, nucleic acids which span the intron-exon boundaries of the said VGSC gene may not be able to selectively hybridise to the said VGSC mRNA or cDNA.

Typical moderately or highly stringent hybridisation conditions which lead to selective hybridisation are known in the art, for example those described in *Molecular Cloning, a laboratory manual*, 2nd edition, Sambrook et al (eds), Cold Spring Harbor Laboratory Press, Cold Spring Harbor, N.Y., USA, incorporated herein by reference.

An example of a typical hybridisation solution when a nucleic acid is immobilised on a nylon membrane and the probe nucleic acid is $\geq$500 bases or base pairs is:
6×SSC (saline Na$^+$ citrate)
0.5% Na$^+$ dodecyl sulphate (SDS)
100 µg/ml denatured, fragmented salmon sperm DNA The hybridisation is performed at 68° C. The nylon membrane, with the nucleic acid immobilised, may be washed at 68° C. in 1×SSC or, for high stringency, 0.1×SSC.

20×SSC may be prepared in the following way. Dissolve 175.3 g of NaCl and 88.2 g of Na$^+$ citrate in 800 ml of H$_2$O. Adjust the pH to 7.0 with a few drops of a 10 N solution of NaOH. Adjust the volume to 1 litre with H$_2$O. Dispense into aliquots. Sterilize by autoclaving.

An example of a typical hybridisation solution when a nucleic acid is immobilised on a nylon membrane and the probe is an oligonucleotide of between 15 and 50 bases is:
3.0 M trimethylammonium chloride (TMACl)
0.01 M Na$^+$ phosphate (pH 6.8)
1 mm EDTA (pH 7.6)

0.5% SDS
100 µg/ml denatured, fragmented salmon sperm DNA
0.1% nonfat dried milk The optimal temperature for hybridization is usually chosen to be 5° C. below the $T_i$ for the given chain length. $T_i$ is the irreversible melting temperature of the hybrid formed between the probe and its target sequence. Jacobs et al (1988) *Nucl. Acids Res*. 16, 4637 discusses the determination of $T_i$s. The recommended hybridization temperature for 17-mers in 3 M TMACl is 48-50° C.; for 19-mers, it is 55-57° C.; and for 20-mers, it is 58-66° C.

By "nucleic acid which selectively hybridises" is also included nucleic acids which will amplify DNA from the said VGSC mRNA by any of the well known amplification systems such as those described in more detail below, in particular the polymerase chain reaction (PCR). Suitable conditions for PCR amplification include amplification in a suitable 1× amplification buffer:

10× amplification buffer is 500 mM KCl; 100 mM Tris.Cl (pH 8.3 at room temperature); 15 mM $MgCl_2$; 0.1% gelatin.

A suitable denaturing agent or procedure (such as heating to 95° C.) is used in order to separate the strands of double-stranded DNA.

Suitably, the annealing part of the amplification is between 37° C. and 60° C., preferably 50° C.

Although the nucleic acid which is useful in the methods of the invention may be RNA or DNA, DNA is preferred. Although the nucleic acid which is useful in the methods of the invention may be double-stranded or single-stranded, single-stranded nucleic acid is preferred under some circumstances such as in nucleic acid amplification reactions.

The nucleic acid which is useful in the methods of the invention may be any suitable size. However, for certain diagnostic, probing or amplifying purposes, it is preferred if the nucleic acid has fewer than 10 000, more preferably fewer than 1000, more preferably still from 10 to 100, and in further preference from 15 to 30 base pairs (if the nucleic acid is double-stranded) or bases (if the nucleic acid is single stranded). As is described more fully below, single-stranded DNA primers, suitable for use in a polymerase chain reaction, are particularly preferred.

The nucleic acid for use in the methods of the invention is a nucleic acid capable of hybridising to the said VGSC mRNA or mRNAs. Fragments of the said VGSC genes and cDNAs derivable from the mRNA encoded by the said VGSC genes are also preferred nucleic acids for use in the methods of the invention.

It is particularly preferred if the nucleic acid for use in the methods of the invention is an oligonucleotide primer which can be used to amplify a portion of the said VGSC nucleic acid, particularly VGSC mRNA.

Nucleic acids for use in the invention may hybridise to more than one, for example all, substantially all or a particular subset of VGSC mRNAs. The SCN5A, SCN8A and SCN9A mRNAs are similar to, but distinct from other VGSC mRNAs. This is discussed further in Examples 1 and 2. Thus the nucleic acid for use in the invention may hybridise to a part of VGSC mRNAs that encodes a region of the VGSC polypeptide that is conserved between VGSCs, for example has the same amino acid sequence in all, substantially all or a particular subset of VGSCs. Preferred nucleic acids for use in the invention are those that selectively hybridise to the SCN5A, SCN8A or SCN9A mRNA and do not hybridise to other VGSC mRNAs. Such selectively hybridising nucleic acids can be readily obtained, for example, by reference to whether or not they hybridise to the said VGSC mRNA and not to other VGSC mRNAs.

For example, SCN5A may be distinguished from other VGSCαs by possession of C-terminal PDZ domains, as discussed in Example 1; a nucleic acid hybridising to a nucleic acid encoding at least part of this C-terminal region in combination with a nucleic acid hybridising to a nucleic acid encoding another (non-PDZ domain) portion of SCN5A may be specific for SCN5A. The nucleic acids may be part of the same nucleic acid molecule or may be separate nucleic acid molecules.

Methods and nucleic acids as described, for example, in Example 1, may be used. In particular, a semi-quantitative PCR technique, for example as described in Example 1, may be used. Examples of selectively hybridising nucleic acids for SCN5A, SCN8A and SCN9A are shown in Table 1.

The methods are suitable in respect of any cancer but it is preferred if the cancer is breast cancer. The cancer may be small cell carcinoma of the lung or a glioma or ovarian cancer or prostate cancer. It will be appreciated that the methods of the invention include methods of prognosis and methods which aid diagnosis. It will also be appreciated that the methods of the invention are useful to the physician or surgeon in determining a course of management or treatment of the patient.

The diagnostic and prognostic methods of the invention are particularly suited to female patients.

It is preferred if the nucleic acid is derived from a sample of the tissue in which cancer is suspected or in which cancer may be or has been found. For example, if the tissue in which cancer is suspected or in which cancer may be or has been found is breast, it is preferred if the sample containing nucleic acid is derived from the breast (including armpit tissue, for example lymph node tissue) of the patient. Samples of breast may be obtained by surgical excision, "true cut" biopsies, needle biopsy, nipple aspirate, aspiration of a lump or image-guided biopsy. The image may be generated by X-ray, ultrasound or (less preferably) technetium-99-labelled antibodies or antibody fragments which bind or locate selectively at the breast. Magnetic resonance imaging (MRI) may be used to distinguish fibrosis from breast cancer.

The sample may be directly derived from the patient, for example, by biopsy of the tissue, or it may be derived from the patient from a site remote from the tissue, for example because cells from the tissue have migrated from the tissue to other parts of the body. Alternatively, the sample may be indirectly derived from the patient in the sense that, for example, the tissue or cells therefrom may be cultivated in vitro, or cultivated in a xenograft model; or the nucleic acid sample may be one which has been replicated (whether in vitro or in vivo) from nucleic acid from the original source from the patient. Thus, although the nucleic acid derived from the patient may have been physically within the patient, it may alternatively have been copied from nucleic acid which was physically within the patient. The tumour tissue may be taken from the primary tumour or from metastases. The sample may be lymph nodes, lymph or blood and the spread of disease detected.

Conveniently, the nucleic acid capable of hybridising to the said VGSC mRNA and which is used in the methods of the invention further comprises a detectable label.

By "detectable label" is included any convenient radioactive label such as $^{32}P$, $^{33}P$ or $^{35}S$ which can readily be incorporated into a nucleic acid molecule using well known methods; any convenient fluorescent or chemiluminescent label which can readily be incorporated into a nucleic acid is also included. In addition the term "detectable label" also includes a moiety which can be detected by virtue of binding to another moiety (such as biotin which can be detected by binding to streptavidin); and a moiety, such as an enzyme, which can be detected by virtue of its ability to convert a colourless compound into a coloured compound, or vice versa (for example, alkaline phosphatase can convert colourless o-nitrophenylphosphate into coloured o-nitrophenol). Conveniently, the nucleic acid probe may occupy a certain position in a fixed assay and whether the nucleic acid hybridises to the said VGSC nucleic acid can be determined by reference to the position of hybridisation in the fixed assay. The detectable label may also be a fluorophore-quencher pair as described in Tyagi & Kramer (1996) *Nature Biotechnology* 14, 303-308.

Other types of labels and tags are disclosed above. The nucleic acid may be branched nucleic acid (see Urdea et al (1991) *Nucl. Acids Symposium Series* 24, 197-200).

It will be appreciated that the aforementioned methods may be used for presymptomatic screening of a patient who is in a risk group for cancer. High risk patients for screening include patients over 50 years of age or patients who carry a gene resulting in increased susceptibility (eg predisposing versions of BRCA1, BRCA2 or p53); patients with a family history of breast/ovarian cancer; patients with affected siblings; nulliparous women; and women who have a long interval between menarche and menopause. Similarly, the methods may be used for the pathological classification of tumours such as breast tumours.

Conveniently, in the methods of the invention the nucleic acid which is capable of the said selective hybridisation (whether labelled with a detectable label or not) is contacted with nucleic acid (eg mRNA) derived from the patient under hybridising conditions. Suitable hybridising conditions include those described above.

The presence of a complex which is selectively formed by the nucleic acid hybridising to the VGSC mRNA may be detected, for example the complex may be a DNA:RNA hybrid which can be detected using antibodies. Alternatively, the complex formed upon hybridisation may be a substrate for an enzymatic reaction the product of which may be detected (suitable enzymes include polymerases, ligases and endonucleases).

It is preferred that if the sample containing nucleic acid (eg mRNA) derived from the patient is not a substantially pure sample of the tissue or cell type in question that the sample is enriched for the said tissue or cells.

For example, enrichment for breast cells in a sample such as a blood sample may be achieved using, for example, cell sorting methods such as fluorescent activated cell sorting (FACS) using a breast cell-selective antibody, or at least an antibody which is selective for an epithelial cell. For example, anti-MUC1 antibodies such as HMFG-1 and HMFG-2 may be used (Taylor-Papadimitriou et al (1986) *J. Exp. Pathol.* 2, 247-260); other anti-MUC1 antibodies which may be useful are described in Cao et al (1998) *Tumour Biol.* 19, (Suppl 1), 88-99. The source of the said sample also includes biopsy material as discussed above and tumour samples, also including fixed paraffin mounted specimens as well as fresh or frozen tissue. The nucleic acid sample from the patient may be processed prior to contact with the nucleic acid which selectively hybridises to the VGSC mRNA. For example, the nucleic acid sample from the patient may be treated by selective amplification, reverse transcription, immobilisation (such as sequence specific immobilisation), or incorporation of a detectable marker.

Cells may be analysed individually, for example using single-cell immobilisation techniques. Methods by which single cells may be analysed include methods in which the technique of Laser Capture Microdissection (LCM) is used. This technique may be used to collect single cells or homogeneous cell populations for molecular analysis and is described in, for example, Jin et al (1999) *Lab Invest* 79(4), 511-512; Simone et al (1998) *Trends Genet* 14(7), 272-276; Luo et al (1999) *Nature Med* 5(1), 117-122; Arcuturs Updates, for example June 1999 and February 1999; U.S. Pat. No. 5,859,699 (all incorporated herein by reference). The cells of interest are visualised, for example by immunohistochemical techniques, and transferred to a polymer film that is activated by laser pulses. The technique may also be used for isolation of cells which are negative for a particular component. Microscopes useful in performing LCM are manufactured by Arcturus Engineering, Inc., 1220 Terra Bella Avenue, Mountain View, Calif. 94042, USA.

LCM may be used with other isolation or enrichment methods. For example, LCM may be used following a method which enriches the sample for the target cell type.

It will be appreciated that the VGSC mRNA may be identified by reverse-transcriptase polymerase chain reaction (RT-PCR) using methods well known in the art.

Primers which are suitable for use in a polymerase chain reaction (PCR; Saild et al (1988) *Science* 239, 487-491) are preferred. Suitable PCR primers may have the following properties:

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artifactual product called "primer dimer". When the 3' ends of the two primers hybridize, they form a "primed template" complex, and primer extension results in a short duplex product called "primer dimer".

Internal secondary structure should be avoided in primers. For symmetric PCR, a 40-60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37-55° C. region, so primer extension will occur during the annealing step and the hybrid will be stabilized. The concentrations of the primers are equal in conventional (symmetric) PCR and, typically, within 0.1- to 1-µM range.

Any of the nucleic acid amplification protocols can be used in the method of the invention including the polymerase chain reaction, QB replicase and ligase chain reaction. Also, NASBA (nucleic acid sequence based amplification), also called 3SR, can be used as described in Compton (1991) *Nature* 350, 91-92 and *AIDS* (1993), Vol 7 (Suppl 2), S108 or SDA (strand displacement amplification) can be used as described in Walker et al (1992) *Nucl. Acids Res.* 20, 1691-1696. The polymerase chain reaction is particularly preferred because of its simplicity.

When a pair of suitable nucleic acids of the invention are used in a PCR it is convenient to detect the product by gel electrophoresis and ethidium bromide staining. As an alternative to detecting the product of DNA amplification using agarose gel electrophoresis and ethidium bromide staining of the DNA, it is convenient to use a labelled oligonucleotide capable of hybridising to the amplified DNA as a probe.

When the amplification is by a PCR the oligonucleotide probe hybridises to the interprimer sequence as defined by the two primers. The oligonucleotide probe is preferably between 10 and 50 nucleotides long, more preferably between 15 and 30 nucleotides long. The probe may be labelled with a radionuclide such as $^{32}P$, $^{33}P$ and $^{35}S$ using standard techniques, or may be labelled with a fluorescent dye. When the oligonucleotide probe is fluorescently labelled, the amplified DNA product may be detected in solution (see for example Balaguer et al (1991) "Quantification of DNA sequences obtained by polymerase chain reaction using a bioluminescence adsorbent" *Anal. Biochem.* 195, 105-110 and Dilesare et al (1993) "A high-sensitivity electrochemiluminescence-based detection system for automated PCR product quantitation" *BioTechniques* 15, 152-157.

PCR products can also be detected using a probe which may have a fluorophore-quencher pair or may be attached to a solid support or may have a biotin tag or they may be detected using a combination of a capture probe and a detector probe.

Fluorophore-quencher pairs are particularly suited to quantitative measurements of PCR reactions (eg RT-PCR). Fluorescence polarisation using a suitable probe may also be used to detect PCR products.

Oligonucleotide primers can be synthesised using methods well known in the art, for example using solid-phase phosphoramidite chemistry.

The present invention provides the use of a nucleic acid which selectively hybridises to SCN5A nucleic acid (eg mRNA) in a method of diagnosing cancer or prognosing cancer or determining susceptibility to cancer (preferably breast cancer); or in the manufacture of a reagent for carrying out these methods. The present invention further provides the use of a nucleic acid which selectively hybridises to VGCS nucleic acid (eg mRNA), preferably SCN5A and/or SCN9A nucleic acid, in a method of diagnosing breast cancer or prognosing breast cancer or determining susceptibility to breast cancer; or in the manufacture of a reagent for carrying out these methods.

Other methods of detecting mRNA levels are included.

Methods for determining the relative amount of the said VGSC mRNA include: in situ hybridisation (In Situ Hybridization Protocols. Methods in Molecular Biology Volume 33. Edited by K H A Choo. 1994, Humana Press Inc (Totowa, N.J., USA) pp 480p and In Situ Hybridization: A Practical Approach. Edited by D G Wilkinson. 1992, Oxford University Press, Oxford, pp 163), in situ amplification, northerns, nuclease protection, probe arrays, and amplification based systems;

The mRNA may be amplified prior to or during detection and quantitation. 'Real time' amplification methods wherein the product is measured for each amplification cycle may be particularly useful (eg Real time PCR Hid et al (1996) *Genome Research* 6, 986-994, Gibson et al (1996) *Genome Research* 6, 995-1001; Real time NASBA Oehlenschlager et al (1996 Nov. 12) *PNAS (USA)* 93(23), 12811-6. Primers should be designed to preferentially amplify from an mRNA template rather than from the DNA, or be designed to create a product where the mRNA or DNA template origin can be distinguished by size or by probing. NASBA may be particularly useful as the process can be arranged such that only RNA is recognised as an initial substrate.

Detecting mRNA includes detecting mRNA in any context, or detecting that there are cells present which contain mRNA (for example, by in situ hybridisation, or in samples obtained from lysed cells). It is useful to detect the presence of mRNA or that certain cells are present (either generally or in a specific location) which can be detected by virtue of their expression of the said VGSC mRNA. As noted, the presence versus absence of the said VGSC mRNA may be a useful marker, or low levels versus high levels of the said VGSC mRNA may be a useful marker, or specific quantified levels may be associated with a specific disease state. It will be appreciated that similar possibilities exist in relation to using the said VGSC polypeptide as a marker.

In a further preferred embodiment, the level of said VGSC protein is measured. Preferably, the level of said protein is measured by contacting the protein with a molecule which selectively binds to said VGSC polypeptide.

The sample containing protein derived from the patient is conveniently a sample tissue. It may be useful to measure the presence (tumour) versus absence (normal) of the said VGSC polypeptide in some circumstances, such as when assessing breast tissue. The methods of the invention also include the measurement and detection of the said VGSC polypeptide in test samples and their comparison in a control sample.

The sample containing protein derived from the patient is conveniently a sample of the tissue in which cancer is suspected or in which cancer may be or has been found. These methods may be used for any cancer, but they are particularly suitable in respect of breast cancer. Methods of obtaining suitable samples are described in relation to earlier methods. The sample may also be blood, serum or lymph node-derived material which may be particularly useful in determining whether a cancer has spread. Single cells may be analysed, as noted above.

The methods of the invention involving detection of the said VGSC proteins are particularly useful in relation to historical samples such as those containing paraffin-embedded sections of tumour samples.

The level of said VGSC protein may be determined in a sample in any suitable way.

It is particularly preferred if the molecule which selectively binds to the said VGSC (for example all VGSCs or selected VGSC(s), for example SCN5A) is an antibody.

Antibodies which can selectively bind to VGSCs or a particular form or forms of VGSC are described above and can be made, for example, by using peptides which are respectively conserved in all or in particular VGSCs, or which encompass the differences between one form of VGSC and the other forms. For example, SCN5A may be distinguished from other VGSCαs by possession of C-terminal PDZ domains, as discussed in Example 1; an antibody binding to part of this C-terminal region may be useful in distinguishing SCN5A from other VGSCs (for example in conjunction with an antibody binding to another portion of SCN5A (and other VGSCs)).

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

The level of the said VGSC which is indicative of cancer or metastatic potential may be defined as the increased level present in known cancerous or metastatic cells, preferably cancerous or metastatic breast cells over known non-cancerous or non-metastatic breast cells. The level may be, for example, at least 1½ fold higher in cancerous or metastatic cells, or it may be at least 2-fold or 3-fold higher.

By "the relative amount of said VGSC protein" is meant the amount of said VGSC protein per unit mass of sample tissue or per unit number of sample cells compared to the amount of said VGSC protein per unit mass of known normal tissue or per unit number of normal cells. The relative amount may be determined using any suitable protein quantitation method. In particular, it is preferred if antibodies are used and that the amount of said VGSC protein is determined using methods which include quantitative western blotting, enzyme-linked immunosorbent assays (ELISA) or quantitative immunohistochemistry.

As noted above, an increased level of the said VGSC, for example SCN5A in a sample compared with a known normal tissue sample is suggestive of a tumorigenic sample, with high metastatic potential. In relation to breast tissue, the presence of the said VGSC(SCN5A and/or SCN9A), compared to its absence, is suggestive of carcinogenesis.

Other techniques for raising and purifying antibodies are well known in the art and any such techniques may be chosen to achieve the preparations useful in the methods claimed in this invention. In a preferred embodiment of the invention, antibodies will immunoprecipitate said VGSC proteins from solution as well as react with said VGSC protein on western or immunoblots of polyacrylamide gels. In another preferred embodiment, antibodies will detect said VGSC proteins in paraffin or frozen tissue sections, using immunocytochemical techniques.

Preferred embodiments relating to methods for detecting said VGSC protein include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference.

It will be appreciated that other antibody-like molecules may be used in the method of the inventions including, for example, antibody fragments or derivatives which retain their antigen-binding sites, synthetic antibody-like molecules such as single-chain Fv fragments (ScFv) and domain antibodies (dAbs), and other molecules with antibody-like antigen binding motifs.

A further aspect of the invention provides the use of a molecule which selectively binds to SCN5A VGSC polypeptide (including a natural fragment or variant thereof) in a method of diagnosing cancer or prognosing cancer or determining susceptibility to cancer (preferably breast cancer); or in the manufacture of a reagent for diagnosing cancer or prognosing cancer or determining susceptibility to cancer. The present invention further provides the use of a molecule which selectively binds to a VGSC polypeptide (including a natural fragment or variant thereof), preferably SCN5A or SCN9A, in a method of diagnosing breast cancer or prognosing breast cancer or determining susceptibility to breast cancer; or in the manufacture of a reagent for carrying out these methods.

In a further embodiment the level of the said VGSC is measured by selectively assaying its activity in the sample. The activity of VGSC, for example SCN5A VGSC, in a sample may be assayed by dissociating a biopsy into single cells and in culture assaying (i) the effect of voltage-gated $Na^+$ channel blockers on their motility and (ii) detecting goltage-gated $Na^+$ channel activity by electrophysiological recording. Suitable methods and voltage-gated $Na^+$ channel blockers are described in Example 1.

Preferred diagnostic methods of the invention include what can broadly be described as "invasive" methods and "non-invasive" methods. Invasive methods include, for example, the taking of a biopsy for detection of voltage-gated $Na^+$ channel expression by, for example, (a) immunohistochemical application of a sequence-specific antibody, (b) in situ PCR on tissue sections, or (c) reverse transcription (RT)-PCR of cells, for example epithelial cells (and/or other cell types, for example neuroendocrine or myoepithelial cells) after separating them from the biopsy. Non-invasive methods include obtaining breast-derived cells from blood, which may be separated by affinity and assayed for voltage-gated $Na^+$ channel expression by PCR.

A further aspect of the invention provides the use of an agent which is an agent useful in selectively assaying the activity of SCN5A voltage-gated $Na^+$ channel protein in a sample in a method of diagnosing cancer or prognosing cancer or determining susceptibility to cancer (preferably breast cancer); or in the manufacture of a reagent for diagnosing cancer or prognosing cancer or determining susceptibility to cancer. The present invention further provides the use of an agent which is an agent useful in selectively assaying the activity of a voltage-gated $Na^+$ channel protein, preferably SCN5A or SCN9A, in a sample in a method of diagnosing breast cancer or prognosing breast cancer or determining susceptibility to breast cancer; or in the manufacture of a reagent for carrying out these methods.

The agents as defined are therefore useful in a method of diagnosing cancer.

A further aspect of the invention provides a kit of parts useful for diagnosing cancer, especially breast cancer, comprising an agent which is capable of use in determining the level of SCN5A (and optionally SCN9A) VGSC protein or nucleic acid in a sample. The agent may be a nucleic acid which selectively hybridises to the said VGSC nucleic acid or the agent may be a molecule which selectively binds to the said VGSC protein or the agent may be an agent useful in selectively assaying the activity of the said VGSC.

Preferably, the kit further comprises a control sample containing the said VGSC nucleic acid or protein wherein the control sample may be a negative control (which contains a level of the said VGSC protein or nucleic acid which is not associated with cancer or a high metastatic potential for cancer) or it may be a positive control (which contains a level of the said VGSC protein or nucleic acid which is associated with cancer or a high metastatic potential for cancer). The kit may contain both negative and positive controls. The kit may usefully contain controls of the said VGSC protein or nucleic acid which correspond to different amounts such that a calibration curve may be made.

Suitably, the kit further comprises means for separating breast cells (for example epithelial cells, neuroendocrine or myoepithelial cells) from a sample in order to carry out said VGSC assay. Preferably, the means for separating breast cells includes antibody-coated micro-beads or columns. These are coated with antibodies to cell membrane proteins. For example, as noted above, anti-MUC1 antibodies such as HMFG-1 and HMFG-2 may be used (Taylor-Papadimitriou et al (1986) *J. Exp. Pathol.* 2, 247-260); other anti-MUC1 antibodies which may be useful are described in Cao et al (1998) *Tumour Biol.* 19, (Suppl 1), 88-99. However, anti-MUC1 antibodies may bind to normal bone marrow cells. It is preferred to use an anti epithelial cell adhesion molecule antibody, preferably coated on magnetic beads. A preferred antibody is termed BER-EP-4.

A further aspect of the invention provides a kit of parts useful for diagnosing breast cancer, comprising (1) an agent which is capable of use in determining the level of VGSC, preferably SCN5A or SCN9A, protein or nucleic acid in a sample, and (2) means for separating breast cells (for example epithelial cells, neuroendocrine or myoepithelial cells) from a sample in order to carry out said VGSC assay.

The kits may usefully further comprise a component for testing for a further cancer-related polypeptide such as antibodies which are reactive with one or more of the following cancer-related polypeptides, all of which are well known in the art: MAGE-1, MAGE-3, BAGE, GAGE-1, CAG-3, CEA, p53, oestrogen receptor (ER), progesterone receptor (PR), MUC1, p52 trefoil peptide, Her2, PCNA, Ki67, cyclin D, p90$^{rak3}$, p170 glycoprotein (mdr-1) CA-15-3, c-erbB1, cathepsin D, PSA, CA125, CA19-9, PAP, myc, cytokeratins, bcl-2, telomerase, glutathione S transferases, rad51, VEGF, thymidine phosphorylase, Flk1 or Flk2.

The kit may usefully still further or alternatively comprise a nucleic acid which selectively hybridises to a further cancer-related nucleic acid such as a gene or mRNA which encodes any of the cancer-related polypeptides as described above. In addition, useful nucleic acids which may be included in the kit are those which selectively hybridise with the genes or mRNAs: ras, APC, BRCA1, BRCA2, ataxia telangiectasia (ATM), hMSH2, hMCH1, hPMS2 or hPMS1. It is preferred if the further nucleic acid is one which selectively hybridises to the gene or mRNA of any of erbB2, p53, BRCA1, BRCA2 or ATM.

The kits usefully may contain controls and detection material, (for example, for immunohistochemistry, secondary antibodies labelled fluorophores, or enzymes, or biotin, or digoxygenin or the like). For immunoassays, additional components to the kit may include a second antibody to a different epitope on the VGSC (optionally labelled or attached to a support), secondary antibodies (optionally labelled or attached to a support), and dilution and reaction buffers. Similar additional components may usefully be included in all of the kits of the invention.

A further aspect of the invention provides a method of treating cancer comprising the step of administering to the patient an agent which selectively prevents the function of SCN5A (and optionally also SCN9A) voltage-gated Na$^+$ channel.

A further aspect of the invention provides a method of treating breast cancer comprising the step of administering to the patient an agent which selectively prevents the function of a voltage-gated Na$^+$ channel, preferably SCN5A or SCN9A, still more preferably selectively SCN5A or SCN9A.

By "an agent which selectively prevents the function of a voltage-gated Na$^+$ channel" we include agents that (a) inhibit the expression of a said VGSC or (b) inhibit the activity of a said VGSC.

Agents that prevent the expression of said VGSC include but are not limited to antisense agents and ribozymes.

Antisense oligonucleotides are single-stranded nucleic acid, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise sequence-specific molecules which specifically bind double-stranded DNA via recognition of major groove hydrogen binding sites.

By binding to the target nucleic acid, the above oligonucleotides can inhibit the function of the target nucleic acid. This could, for example, be a result of blocking the transcription, processing, poly(A) addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene. Antisense oligonucleotides were first discovered to inhibit viral replication or expression in cell culture for Rous sarcoma virus, vesicular stomatitis virus, herpes simplex virus type 1, simian virus and influenza virus. Since then, inhibition of mRNA translation by antisense oligonucleotides has been studied extensively in cell-free systems including rabbit reticulocyte lysates and wheat germ extracts. Inhibition of viral function by antisense oligonucleotides has been demonstrated in vitro using oligonucleotides which were complementary to the AIDS HIV retrovirus RNA (Goodchild, J. 1988 "Inhibition of Human Immunodeficiency Virus Replication by Antisense Oligodeoxynucleotides", *Proc. Natl. Acad. Sci. (USA)* 85(15), 5507-11). The Goodchild study showed that oligonucleotides that were most effective were complementary to the poly(A) signal; also effective were those targeted at the 5' end of the RNA, particularly the cap and 5' untranslated region, next to the primer binding site and at the primer binding site. The cap, 5' untranslated region, and poly(A) signal lie within the sequence repeated at the ends of retrovirus RNA (R region) and the oligonucleotides complementary to these may bind twice to the RNA.

Oligonucleotides are subject to being degraded or inactivated by cellular endogenous nucleases. To counter this problem, it is possible to use modified oligonucleotides, eg having altered internucleotide linkages, in which the naturally occurring phosphodiester linkages have been replaced with another linkage. For example, Agrawal et al (1988) *Proc. Natl. Acad. Sci. USA* 85, 7079-7083 showed increased inhibition in tissue culture of HIV-1 using oligonucleotide phosphoramidates and phosphorothioates. Sarin et al (1988) *Proc. Natl. Acad. Sci. USA* 85, 7448-7451 demonstrated increased inhibition of HIV-1 using oligonucleotide methylphosphonates.

Agrawal et al (1989) *Proc. Natl. Acad. Sci. USA* 86, 7790-7794 showed inhibition of HIV-1 replication in both early-infected and chronically infected cell cultures, using nucleotide sequence-specific oligonucleotide phosphorothioates. Leither et al (1990) *Proc. Natl. Acad. Sci. USA* 87, 3430-3434 report inhibition in tissue culture of influenza virus replication by oligonucleotide phosphorothioates.

Oligonucleotides having artificial linkages have been shown to be resistant to degradation in vivo. For example, Shaw et al (1991) in *Nucleic Acids Res*. 19, 747-750, report that otherwise unmodified oligonucleotides become more resistant to nucleases in vivo when they are blocked at the 3' end by certain capping structures and that uncapped oligonucleotide phosphorothioates are not degraded in vivo.

A detailed description of the H-phosphonate approach to synthesizing oligonucleoside phosphorothioates is provided in Agrawal and Tang (1990) *Tetrahedron Letters* 31, 7541-7544, the teachings of which are hereby incorporated herein by reference. Syntheses of oligonucleoside methylphosphonates, phosphorodithioates, phosphoramidates, phosphate esters, bridged phosphoramidates and bridge phosphorothioates are known in the art. See, for example, Agrawal and Goodchild (1987) *Tetrahedron Letters* 28, 3539; Nielsen et al (1988) *Tetrahedron Letters* 29, 2911; Jager et al (1988) *Biochemistry* 27, 7237; Uznanski et al (1987) *Tetrahedron Letters* 28, 3401; Bannwarth (1988) *Helv. Chim. Acta*. 71, 1517; Crosstick and Vyle (1989) *Tetrahedron Letters* 30, 4693;

Agrawal et al (1990) *Proc. Natl. Acad. Sci. USA* 87, 1401-1405, the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesized and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example, by replacing phosphate with sulphur in the linkage. Examples of linkages that may be used include phosphorothioates, methylphosphonates, sulphone, sulphate, ketyl, phosphorodithioates, various phosphoramidates, phosphate esters, bridged phosphorothioates and bridged phosphoramidates. Such examples are illustrative, rather than limiting, since other internucleotide linkages are known in the art. See, for example, Cohen, (1990) *Trends in Biotechnology*. The synthesis of oligonucleotides having one or more of these linkages substituted for the phosphodiester internucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-Link II™ from Applied BioSystems Inc, Foster City, Calif. Methods for capping are described, for example, by Shaw et al (1991) *Nucleic Acids Res*. 19, 747-750 and Agrawal et al (1991) *Proc. Natl. Acad. Sci. USA* 88(17), 7595-7599, the teachings of which are hereby incorporated herein by reference.

A further method of making oligonucleotides resistant to nuclease attack is for them to be "self-stabilized" as described by Tang et al (1993) *Nucl. Acids Res*. 21, 2729-2735 incorporated herein by reference. Self-stabilized oligonucleotides have hairpin loop structures at their 3' ends, and show increased resistance to degradation by snake venom phosphodiesterase, DNA polymerase I and fetal bovine serum. The self-stabilized region of the oligonucleotide does not interfere in hybridization with complementary nucleic acids, and pharmacokinetic and stability studies in mice have shown increased in vivo persistence of self-stabilized oligonucleotides with respect to their linear counterparts.

In accordance with the invention, the inherent binding specificity of antisense oligonucleotides characteristic of base pairing is enhanced by limiting the availability of the antisense compound to its intend locus in vivo, permitting lower dosages to be used and minimizing systemic effects. Thus, oligonucleotides are applied locally to achieve the desired effect. The concentration of the oligonucleotides at the desired locus is much higher than if the oligonucleotides were administered systemically, and the therapeutic effect can be achieved using a significantly lower total amount. The local high concentration of oligonucleotides enhances penetration of the targeted cells and effectively blocks translation of the target nucleic acid sequences.

The oligonucleotides can be delivered to the locus by any means appropriate for localized administration of a drug. For example, a solution of the oligonucleotides can be injected directly to the site or can be delivered by infusion using an infusion pump. The oligonucleotides also can be incorporated into an implantable device which when placed at the desired site, permits the oligonucleotides to be released into the surrounding locus.

The oligonucleotides may be administered via a hydrogel material. The hydrogel is noninflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10 to about 80% by weight ethylene oxide and from about 20 to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic$^R$.

In this embodiment, the hydrogel is cooled to a liquid state and the oligonucleotides are admixed into the liquid to a concentration of about 1 mg oligonucleotide per gram of hydrogel. The resulting mixture then is applied onto the surface to be treated, for example by spraying or painting during surgery or using a catheter or endoscopic procedures. As the polymer warms, it solidifies to form a gel, and the oligonucleotides diffuse out of the gel into the surrounding cells over a period of time defined by the exact composition of the gel.

The oligonucleotides can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the oligonucleotides. The oligonucleotides can be incorporated into the material as it is polymerized or solidified, using melt or solvent evaporation techniques, or mechanically mixed with the material. In one embodiment, the oligonucleotides are mixed into or applied onto coatings for implantable devices such as dextran coated silica beads, stents, or catheters. Polymeric nanoparticles/biodegradable drug carriers may also be used (Mader (1998) *Radiol. Oncol*. 32, 89-94).

The dose of oligonucleotides is dependent on the size of the oligonucleotides and the purpose for which it is administered. In general, the range is calculated based on the surface area of tissue to be treated. The effective dose of oligonucleotide is somewhat dependent on the length and chemical composition of the oligonucleotide but is generally in the range of about 30 to 3000 µg per square centimetre of tissue surface area.

The oligonucleotides may be administered to the patient systemically for both therapeutic and prophylactic purposes. The oligonucleotides may be administered by any effective method, for example, parenterally (eg intravenously, subcutaneously, intramuscularly) or by oral, nasal or other means which permit the oligonucleotides to access and circulate in the patient's bloodstream. Oligonucleotides administered systemically preferably are given in addition to locally administered oligonucleotides, but also have utility in the absence of local administration. A dosage in the range of from about 0.1 to about 10 grams per administration to an adult human generally will be effective for this purpose.

It will be appreciated that it may be desirable to target the antisense oligonucleotides to the cancerous tissue, for example to the breast. This may be achieved by administering the antisense oligonucleotides to the cancer location (for example the breast), or it may be achieved by using antisense oligonucleotides which are in association with a molecule which selectively directs the antisense oligonucleotide to the cancer location. For example, the antisense oligonucleotide may be associated with an antibody or antibody like molecule which selectively binds a breast-related antigen such as MUC-1. By "associated with" we mean that the antisense oligonucleotide and the cancer-directing entity are so associated that the cancer-directing entity is able to direct the antisense oligonucleotide to the location of the cancer cells, for example breast cells.

It will be appreciated that antisense agents also include larger molecules, for example of around one hundred to several hundred bases which bind to said VGSC mRNA or genes and substantially prevent expression of said VGSC mRNA or genes and substantially prevent expression of said VGSC protein. Thus, expression of an antisense molecule which is substantially complementary to said VGSC mRNA is envisaged as part of the invention.

Thus, in this approach, synthetic oligonucleotides with antisense sequence to specific regions of (i) SCN5A (and optionally also SCN9A) channels or (ii) (for patients with or at risk of breast cancer) SCN5A or SCN9A channels or VGSCs generally, are administered (preferably to patients with or at risk of breast cancer) to block channel activity. Details of particular synthetic oligonucleotides are given in Example 2. It is noteworthy that antisense oligonucleotide technology has already been used to manipulate potassium channels in vitro (Roy et al (1996) *Glia* 18, 174-188) and VGSCs in vitro (*Biochem Biophys Res Comm* (1997) 234, 235-241) and in blocking neuropathic pain (Lai et al (1999) "Blockade of neuropathic pain by antisense targeting of tetrodotoxin-resistant sodium channels in sensory neurons" *Methods in Enzymol* 314, 201-213).

A further method for blocking said VGSC activity includes dominant negative suppression. In this technique, a mutated VGSC gene product suppresses or eliminates the activity of the corresponding normal gene product when the two are co-expressed. In the case of voltage-gated potassium channels (VGPCs) which comprise 4 alpha subunits, such an approach making use of a highly truncated gene product, has been used successfully to suppress functional expression of VGPCs in vitro (Tu et al (1995) *Biophys. J.* 68, 147-156) and in vivo (London et al (1998) *Proc. Natl. Acad. Sci. USA* 95, 2926-2931). The truncated subunit is capable of binding to other VGPC subunits but does not contain the residues required for channel functioning. Thus, the activity of the "combined" VGPC is blocked. A number of naturally occurring alternatively spliced channel subunits have been detected which may function to suppress VGPC activity by a similar mechanism in vivo (Baumann et al (1987) *EMBO J.* 6, 3419-3429; Kamb et al (1988) *Neuron* 1, 421-430; and Pongs et al (1988) *EMBO J.* 7, 1087-1096). We believe that VGSC may similarly be suppressed by interfering with functional channel formation. Although VGSCs are formed from a single alpha subunit (comprising four functional domains), recent studies have demonstrated the specific expression (during development in human, mouse and fish) of truncated VGSC proteins possessing only two domains which might function in a dominant negative manner to control VGSC activity (Plummer et al (1997) *J. Biol. Chem.* 272, 24008-24015; and Oh & Waxman (1998) *NeuroReport* 9, 1267-1271). The neonatal VGSCs may act as inhibitors of VGSC activity, but this inhibition is most probably specific to the related adult VGSC. It is much less likely that, for example, neonatal SCN8A could inhibit the activity of VGSC proteins derived from VGSC genes other than SCN8A.

The larger molecules may be expressed from any suitable genetic construct as is described below and delivered to the patient. Typically, the genetic construct which expresses the antisense molecule comprises at least a portion of the said VGSC cDNA or gene operatively linked to a promoter which can express the antisense molecule in the cell, preferably breast cell, which is or may become cancerous.

Although the genetic construct can be DNA or RNA it is preferred if it is DNA.

Preferably, the genetic construct is adapted for delivery to a human cell.

Means and methods of introducing a genetic construct into a cell in an animal body are known in the art. For example, the constructs of the invention may be introduced into the tumour cells by any convenient method, for example methods involving retroviruses, so that the construct is inserted into the genome of the tumour cell. For example, in Kuriyama et al (1991) *Cell Struc. and Func.* 16, 503-510 purified retroviruses are administered. Retroviruses provide a potential means of selectively infecting cancer cells because they can only integrate into the genome of dividing cells; most normal cells surrounding cancers are in a quiescent, non-receptive stage of cell growth or, at least, are dividing much less rapidly than the tumour cells. Retroviral DNA constructs which encode said antisense agents may be made using methods well known in the art. To produce active retrovirus from such a construct it is usual to use an ecotropic psi2 packaging cell line grown in Dulbecco's modified Eagle's medium (DMEM) containing 10% foetal calf serum (FCS). Transfection of the cell line is conveniently by calcium phosphate co-precipitation, and stable transformants are selected by addition of G418 to a final concentration of 1 mg/ml (assuming the retroviral construct contains a $neo^R$ gene). Independent colonies are isolated and expanded and the culture supernatant removed, filtered through a 0.45 μm pore-size filter and stored at −70'. For the introduction of the retrovirus into the tumour cells, it is convenient to inject directly retroviral supernatant to which 10 μg/ml Polybrene has been added. For tumours exceeding 10 mm in diameter it is appropriate to inject between 0.1 ml and 1 ml of retroviral supernatant; preferably 0.5 ml.

Alternatively, as described in Culver et al (1992) *Science* 256, 1550-1552, cells which produce retroviruses are injected into the tumour. The retrovirus-producing cells so introduced are engineered to actively produce retroviral vector particles so that continuous productions of the vector occurred within the tumour mass in situ. Thus, proliferating tumour cells can be successfully transduced in vivo if mixed with retroviral vector-producing cells.

Targeted retroviruses are also available for use in the invention; for example, sequences conferring specific binding affinities may be engineered into preexisting viral env genes (see Miller & Vile (1995) *Faseb J.* 9, 190-199 for a review of this and other targeted vectors for gene therapy).

Other methods involve simple delivery of the construct into the cell for expression therein either for a limited time or, following integration into the genome, for a longer time. An example of the latter approach includes (preferably tumour-cell-targeted) liposomes (Nässander et al (1992) *Cancer Res.* 52, 646-653).

Immunoliposomes (antibody-directed liposomes) are especially useful in targeting to cancer cell types which overexpress a cell surface protein for which antibodies are available. For example, the immunoliposomes may be targeted by means of antibodies binding to a breast cancer cell antigen such as MUC-1, or the said VGSC (preferably in combination with other targeting means or methods), as discussed further below. For the preparation of immuno-liposomes MPB-PE (N-[4-(p-maleimidophenyl)butyryl]-phosphatidylethanolamine) is synthesised according to the method of Martin & Papahadjopoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with the DNA or other genetic construct of the invention for delivery to the target cells, for example, by forming the said liposomes in a solution of the DNA or other genetic construct, followed by sequential extrusion through polycarbonate membrane filters with 0.6 µm and 0.2 µm pore size under nitrogen pressures up to 0.8 MPa. After extrusion, entrapped DNA construct is separated from free DNA construct by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g, for 45 min. Immunoliposomes may be injected intraperitoneally or directly into the tumour.

Other methods of delivery include adenoviruses carrying external DNA via an antibody-polylysine bridge (see Curiel *Prog. Med. Virol.* 40, 1-18) and transferrin-polycation conjugates as carriers (Wagner et al (1990) *Proc. Natl. Acad. Sci. USA* 87, 3410-3414). In the first of these methods a polycation-antibody complex is formed with the DNA construct or other genetic construct of the invention, wherein the antibody is specific for either wild-type adenovirus or a variant adenovirus in which a new epitope has been introduced which binds the antibody. The polycation moiety binds the DNA via electrostatic interactions with the phosphate backbone. The adenovirus, because it contains unaltered fibre and penton proteins, is internalized into the cell and carries into the cell with it the DNA construct of the invention. It is preferred if the polycation is polylysine.

The DNA may also be delivered by adenovirus wherein it is present within the adenovirus particle, for example, as described below.

In the second of these methods, a high-efficiency nucleic acid delivery system that uses receptor-mediated endocytosis to carry DNA macromolecules into cells is employed. This is accomplished by conjugating the iron-transport protein transferrin to polycations that bind nucleic acids. Human transferrin, or the chicken homologue conalbumin, or combinations thereof is covalently linked to the small DNA-binding protein protamine or to polylysines of various sizes through a disulfide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs of the invention are supplied to the tumour cells, a high level of expression from the construct in the cells is expected.

High-efficiency receptor-mediated delivery of the DNA constructs or other genetic constructs of the invention using the endosome-disruption activity of defective or chemically inactivated adenovirus particles produced by the methods of Cotten et al (1992) *Proc. Natl. Acad. Sci. USA* 89, 6094-6098 may also be used. This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle.

This approach has the advantages that there is no need to use complex retroviral constructs; there is no permanent modification of the genome as occurs with retroviral infection; and the targeted expression system is coupled with a targeted delivery system, thus reducing toxicity to other cell types.

It may be desirable to locally perfuse a tumour with the suitable delivery vehicle comprising the genetic construct for a period of time; additionally or alternatively the delivery vehicle or genetic construct can be injected directly into accessible tumours.

It will be appreciated that "naked DNA" and DNA complexed with cationic and neutral lipids may also be useful in introducing the DNA of the invention into cells of the patient to be treated. Non-viral approaches to gene therapy are described in Ledley (1995) *Human Gene Therapy* 6, 1129-1144.

Alternative targeted delivery systems are also known such as the modified adenovirus system described in WO 94/10323 wherein, typically, the DNA is carried within the adenovirus, or adenovirus-like, particle. Michael et al (1995) *Gene Therapy* 2, 660-668 describes modification of adenovirus to add a cell-selective moiety into a fibre protein. Mutant adenoviruses which replicate selectively in p53-deficient human tumour cells, such as those described in Bischoff et al (1996) *Science* 274, 373-376 are also useful for delivering the genetic construct of the invention to a cell. Thus, it will be appreciated that a further aspect of the invention provides a virus or virus-like particle comprising a genetic construct of the invention. Other suitable viruses or virus-like particles include HSV, AAV, vaccinia and parvovirus.

In a further embodiment the agent which selectively prevents the function of the said VGSC is a ribozyme capable of cleaving targeted VGSC RNA or DNA. A gene expressing said ribozyme may be administered in substantially the same way and using substantially the same vehicles as for the antisense molecules.

Ribozymes which may be encoded in the genomes of the viruses or virus-like particles herein disclosed are described in Cech and Herschlag "Site-specific cleavage of single stranded DNA" U.S. Pat. No. 5,180,818; Altman et al "Cleavage of targeted RNA by RNAse P" U.S. Pat. No. 5,168,053, Cantin et al "Ribozyme cleavage of HIV-1 RNA" U.S. Pat. No. 5,149,796; Cech et al "RNA ribozyme restriction endoribonucleases and methods", U.S. Pat. No. 5,116,742; Been et al "RNA ribozyme polymerases, dephosphorylases, restriction endonucleases and methods", U.S. Pat. No. 5,093,246; and Been et al "RNA ribozyme polymerases, dephosphorylases, restriction endoribonucleases and methods; cleaves single-stranded RNA at specific site by transesterification", U.S. Pat. No. 4,987,071, all incorporated herein by reference.

It will be appreciated that it may be desirable that the antisense molecule or ribozyme is expressed from a breast cell-specific promoter element. Examples of breast cell-specific promoters include the promoter element for c-erbB2 or the oestrogen receptor.

The genetic constructs of the invention can be prepared using methods well known in the art.

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or E. coli DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487-491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

The present invention also relates to a host cell transformed with a genetic (preferably DNA construct) construct of the present invention. The host cell can be either prokaryotic or eukaryotic. Bacterial cells are preferred prokaryotic host cells and typically are a strain of E. coli such as, for example, the E. coli strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast and mammalian cells, preferably vertebrate cells such as those from a mouse, rat, monkey or human fibroblastic cell line. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5×PEB using 6250V per cm at 25 µFD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the molecule as defined in the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the molecule, for example a protein, in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

When the genetic construct is a plasmid DNA construct it can be purified. The DNA construct of the invention is purified from the host cell using well known methods.

For example, plasmid vector DNA can be prepared on a large scale from cleaved lysates by banding in a CsCl gradient according to the methods of Clewell & Helinski (1970) *Biochemistry* 9, 4428-4440 and Clewell (1972) *J. Bacteriol.* 110, 667-676. Plasmid DNA extracted in this way can be freed from CsCl by dialysis against sterile, pyrogen-free buffer through Visking tubing or by size-exclusion chromatography.

Alternatively, plasmid DNA may be purified from cleared lysates using ion-exchange chromatography, for example those supplied by Qiagen. Hydroxyapatite column chromatography may also be used.

A further aspect of the invention provides use of an agent which selectively prevents (including inhibits) the function of SCN5A (and optionally also SCN9A) voltage-gated $Na^+$ channel in the manufacture of a medicament for treating cancer, preferably breast cancer. A further aspect of the invention provides use of an agent which selectively prevents the function of a voltage-gated Na$^+$ channel, preferably SCN5A or SCN9A in the manufacture of a medicament for treating breast cancer (including treating a patient with or at risk of breast cancer).

A further aspect of the invention provides a method of treating a patient with or at risk of cancer (preferably breast cancer) wherein an agent which selectively prevents (including inhibits) the function of SCN5A (and optionally also SCN9A) voltage-gated Na$^+$ channel is administered to the patient. A further aspect of the invention provides a method of treating a patient with or at risk of cancer (preferably breast cancer) wherein an agent which selectively prevents the function of a voltage-gated Na$^+$ channel, preferably SCN5A or SCN9A is administered to the patient.

Agents known as anti-arrhythmic and local anaesthetic drugs may selectively prevent or inhibit the function of SCN5A voltage gated Na$^+$ channels, as well known to those skilled in the art. Antiarrhythmic drugs that have been shown to inhibit SCN5A VGSC activity include: naloxone, flecainide, cinnamophilin and acrophyllidine; local anasthetics include pilsicainide and lidocaine. However, they are not specific blockers of VGSCs, including SCN5A subtype. Such anti-arrhythmic or local anaesthetic drugs may be preferred agents for use in these aspects of the invention.

A still further aspect of the invention provides a genetic construct comprising a nucleic acid encoding a molecule capable of preventing the function of SCN5A (and optionally also SCN9A) voltage-gated Na$^+$ channel expressed in a cell.

A further aspect of the invention provides a genetic construct comprising a nucleic acid encoding a molecule capable of preventing the function of a voltage-gated Na$^+$ channel expressed in a cell, preferably SCN5A and/or SCN9A (most preferably SCN5A), wherein expression of said molecule by the genetic construct is via a breast-selective promoter, or wherein the genetic construct is adapted for selective delivery to a (human) breast cell.

As noted above, the genetic construct may be RNA or DNA. The molecule capable of preventing the function of the said VGSC is conveniently an antisense molecule or a ribozyme as disclosed above.

The genetic constructs are adapted for delivery to a human cell, in particular a cell which is cancerous or in which cancer may occur, and more particularly the genetic construct is adapted for delivery to a breast cell. The genetic constructs of this aspect of the invention include the viral and non-viral delivery systems described above.

Suitably, the molecule is capable of preventing the function of the said VGSC, for example SCN5A VGSC, such as a ribozyme or antisense molecule, is selectively expressed in a cancer cell. For example, expression of said molecule by the genetic construct may be via a cancer cell- or tissue-selective promoter which, in the case of breast cancer, may be the MUC-1 promoter or any other breast-selective promoter.

A further aspect of the invention provides the genetic constructs for use in medicine, preferably for use in treating cancer, still more preferably breast cancer. Thus, the genetic constructs are packaged and presented for use in medicine. A further aspect of the invention provides the use of the said genetic constructs for use in the manufacture of a medicament for the treatment of cancer, preferably breast cancer.

A further aspect of the invention provides a pharmaceutical composition comprising a genetic construct of the invention and a pharmaceutically acceptable carrier. The carriers must be "acceptable" in the sense of being compatible with the genetic construct of the invention and not deleterious to the recipients thereof. Typically, the carriers will be water or saline which will be sterile and pyrogen free.

For the avoidance of doubt, the genetic constructs of the invention specifically include virus or virus-like particles, but also include constructs suitable use with for non-viral delivery systems.

A further aspect of the invention provides a method of identifying a compound which selectively inhibits a SCN5A voltage-gated Na$^+$ channel, the method comprising (a) contacting a test compound with any one of the said voltage-gated Na$^+$ channels and determining whether said compound is inhibitory; (b) contacting the test compound with other voltage-gated Na$^+$ channels and determining whether said compound is inhibitory; and (c) selecting a compound which is substantially inhibitory in (a) but is not substantially inhibitory in (b). The compound may be useful in the treatment of cancer, preferably breast cancer.

Typically, a range of compounds, including pharmacological agents with known effects upon voltage-gated Na$^+$ channels, will be screened for their effectiveness in a number of assays. Suitable assay formats include electrophysiological recording from cells in long-term culture as cell-lines and short term culture of cells dissociated from biopsies (see, for example Grimes & Djamgoz (1998) *J. Cell Physiol.* 175, 50-58); electrophysiological recording from oocytes functionally expressing recombinant said VGSC following injection of cRNAs (see, for example, Fraser et al (1993) *In Electrophysiology*, A practical approach (D. Willis, ed) IRL Press); and in vitro (Boyden chamber) invasion assays (see, for example, Grimes et al (1995) *FEBS Lett* 369, 290-294; and Smith et al (1998) *FEBS Lett*. 423, 19-24).

The present invention also provides methods in which treatment is targeted to cancer cells by means of targeting to cells expressing SCN5A VGSC, or in which treatment is targeted to breast cancer cells by means of targeting to cells expressing a VGSC, preferably SCN5A or SCN9A, as noted above in relation to targeting of genetic constructs to such cells. It will be appreciated that targeting to cells expressing a said VGSC may preferably be performed in conjunction with another targeting means or method, for example local administration, in order to minimise adverse effects on any normal tissues that express the said VGSC. For example, cardiac tissue expresses SCN5A at high levels.

For example, anti-said VGSC antibodies (VGSC-Abs) conjugated with a dye substance may be applied to the cancerous tissue in vivo (eg Yasmuch et al (1993) "Antibody targeted photolysis" *Critical Review Revue Ther. Drug Carrier System* 10, 197-252; Pogrebniak et al (1993) "Targetted phototherapy with sensitizer-monoclonal antibody conjugate and light" *Surgical Onoclogy* 2, 31-42). The tissue is then irradiated locally with a wavelength of light/laser matching the absorption peak of the 'attached' dye.

Absorption of the light energy by the dye leads to local heating and cell death. In this way, only the labelled (ie metastatic) cells will be ablated. VGSC-Abs labelled with the following dyes may be used: fluorescein (Pelegrin et al (1991) "Antibody fluorescein conjugates for photoimmunodiagnosis of human colon-carcinoma in nude-mice" *Cancer* 67, 2529-2537); rhodamine (Haghighat et al (1992) "Laser-dyes for experimental phototherapy of human cancer—comparison of 3 rhodamines" *Laryngoscope* 102, 81-87); cyanins (Folli et al (1994) "Antibody-indocyanin conjugates for immunophotodetection of human squamous-cell carcinoma in nude-mice" *Cancer Research* 54, 2643-2649; Lipshutz et al (1994) "Evaluation of 4 new carbocyanine dyes for photodynamic therapy with lasers" *Laryngoscope* 104, 996-1002; Haddad et al (1998) "In vitro and in vivo effects of photodynamic therapy on murine malignant melanoma" *Annals of Surgical Oncology* 5, 241-247). This may be useful with oesophageal and lung cancer.

Thus, a further aspect of the invention provides a compound comprising a moiety which selectively binds SCN5A voltage-gated Na$^+$ channel protein and a further moiety.

By "a moiety which selectively binds SCN5A voltage-gated Na$^+$ channel protein" we mean any suitable such moiety which binds the said VGSC but does not substantially bind other molecules, for example other VGSCs, for example SCN9A. The compound comprising the binding moiety is one which preferably, in use, is able to localise to areas of cancerous cells (preferably breast cancerous cells), particularly metastatic cancer cells, but not localise substantially to other areas where there are no cancerous cells.

Preferably the binding moiety is able to bind to the said VGSC with high affinity. For example, the binding constant for the binding of the binding moiety to the said VGSC is preferably between $10^{-7}$ and $10^{-10}$ M. Typically the binding moiety is an anti-SNC5A antibody. Such antibodies and methods of preparing suitable antibodies are discussed above.

The further moiety may be any further moiety which confers on the compound a useful property with respect to the treatment or imaging or diagnosis of cancer. In particular, the further moiety is one which is useful in killing or imaging cancer cells, particularly metastatic cancer cells. Preferably, the further moiety is one which is able to kill the cancer cells to which the compound is targeted.

In a preferred embodiment of the invention the further moiety is directly or indirectly cytotoxic. In particular the further moiety is preferably directly or indirectly toxic to cancer cells, particularly metastatic cancer cells.

By "directly cytotoxic" we include the meaning that the moiety is one which on its own is cytotoxic. By "indirectly cytotoxic" we include the meaning that the moiety is one which, although is not itself cytotoxic, can induce cytotoxicity, for example by its action on a further molecule or by further action on it.

In one embodiment the cytotoxic moiety is a cytotoxic chemotherapeutic agent. Cytotoxic chemotherapeutic agents are well known in the art.

Cytotoxic chemotherapeutic agents, such as anticancer agents, include: alkylating agents including nitrogen mustards such as mechlorethamine (HN$_2$), cyclophosphamide, ifosfamide, melphalan (L-sarcolysin) and chlorambucil; ethylenimines and methylmelamines such as hexamethylmelamine, thiotepa; alkyl sulphonates such as busulfan; nitrosoureas such as carmustine (BCNU), lomustine (CCNU), semustine (methyl-CCNU) and streptozocin (streptozotocin); and triazenes such as decarbazine (DTIC; dimethyltriazenoimidazole-carboxamide); Antimetabolites including folic acid analogues such as methotrexate (amethopterin); pyrimidine analogues such as fluorouracil (5-fluorouracil; 5-FU), floxuridine (fluorodeoxyuridine; FUdR) and cytarabine (cytosine arabinoside); and purine analogues and related inhibitors such as mercaptopurine (6-mercaptopurine; 6-MP), thioguanine (6-thioguanine; TG) and pentostatin (2-deoxycoformycin). Natural Products including vinca alkaloids such as vinblastine (VLB) and vincristine; epipodophyllotoxins such as etoposide and teniposide; antibiotics such as dactinomycin (actinomycin D), daunorubicin (daunomycin; rubidomycin), doxorubicin, bleomycin, plicamycin (mithramycin) and mitomycin (mitomycin C); enzymes such as L-asparaginase; and biological response modifiers such as interferon alphenomes. Miscellaneous agents including platinum coordination complexes such as cisplatin (cis-DDP) and carboplatin; anthracenedione such as mitoxantrone and anthracycline; substituted urea such as hydroxyurea; methyl hydrazine derivative such as procarbazine (N-methylhydrazine, MIH); and adrenocortical suppressant such as mitotane (o,p-DDD) and aminoglutethimide; taxol and analogues/derivatives; and hormone agonists/antagonists such as flutamide and tamoxifen.

Various of these agents have previously been attached to antibodies and other target site-delivery agents, and so compounds of the invention comprising these agents may readily be made by the person skilled in the art. For example, carbodiimide conjugation (Bauminger & Wilchek (1980) *Methods Enzymol*. 70, 151-159; incorporated herein by reference) may be used to conjugate a variety of agents, including doxorubicin, to antibodies or peptides.

Carbodiimides comprise a group of compounds that have the general formula R—N═C═N—R', where R and R' can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups.

The water soluble carbodiimide, 1-ethyl-3-(3-dimethylaminopropyl)carbodiimide (EDC) is particularly useful for conjugating a functional moiety to a binding moiety and may be used to conjugate doxorubicin to tumor homing peptides. The conjugation of doxorubicin and a binding moiety requires the presence of an amino group, which is provided by doxorubicin, and a carboxyl group, which is provided by the binding moiety such as an antibody or peptide.

In addition to using carbodiimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger & Wilchek, supra, 1980).

Other methods for conjugating a functional moiety to a binding moiety also can be used. For example, sodium periodate oxidation followed by reductive alkylation of appropriate reactants can be used, as can glutaraldehyde crosslinking. However, it is recognised that, regardless of which method of producing a conjugate of the invention is selected, a determination must be made that the binding moiety maintains its targeting ability and that the functional moiety maintains its relevant function.

In a further embodiment of the invention, the cytotoxic moiety is a cytotoxic peptide or polypeptide moiety by which we include any moiety which leads to cell death. Cytotoxic peptide and polypeptide moieties are well known in the art and include, for example, ricin, abrin, Pseudomonas exotoxin, tissue factor and the like. Methods for linking them to targeting moieties such as antibodies are also known in the art. The use of ricin as a cytotoxic agent is described in Burrows & Thorpe (1993) *Proc. Natl. Acad. Sci. USA* 90, 8996-9000, incorporated herein by reference, and the use of tissue factor, which leads to localised blood clotting and infarction of a tumour, has been described by Ran et al (1998) *Cancer Res*. 58, 4646-4653 and Huang et al (1997) *Science* 275, 547-550. Tsai et al (1995) *Dis. Colon Rectum* 38, 1067-1074 describes the abrin A chain conjugated to a monoclonal antibody and is incorporated herein by reference. Other ribosome inactivating proteins are described as cytotoxic agents in WO 96/06641. Pseudomonas exotoxin may also be used as the cytotoxic polypeptide moiety (see, for example, Aiello et al (1995) *Proc. Natl. Acad. Sci. USA* 92, 10457-10461; incorporated herein by reference).

Certain cytokines, such as TNFα and IL-2, may also be useful as cytotoxic agents.

Certain radioactive atoms may also be cytotoxic if delivered in sufficient doses. Thus, the cytotoxic moiety may comprise a radioactive atom which, in use, delivers a sufficient quantity of radioactivity to the target site so as to be cytotoxic. Suitable radioactive atoms include phosphorus-32, iodine-125, iodine-131, indium-111, rhenium-186, rhenium-188 or yttrium-90, or any other isotope which emits enough energy to destroy neighbouring cells, organelles or nucleic acid. Preferably, the isotopes and density of radioactive atoms in the compound of the invention are such that a dose of more than 4000 cGy (preferably at least 6000, 8000 or 10000 cGy) is delivered to the target site and, preferably, to the cells at the target site and their organelles, particularly the nucleus.

The radioactive atom may be attached to the binding moiety in known ways. For example EDTA or another chelating agent may be attached to the binding moiety and used to attach $^{111}$In or $^{90}$Y. Tyrosine residues may be labelled with $^{125}$I or $^{131}$I.

The cytotoxic moiety may be a suitable indirectly cytotoxic polypeptide. In a particularly preferred embodiment, the indirectly cytotoxic polypeptide is a polypeptide which has enzymatic activity and can convert a relatively non-toxic prodrug into a cytotoxic drug. When the targeting moiety is an antibody this type of system is often referred to as ADEPT (Antibody-Directed Enzyme Prodrug Therapy). The system requires that the targeting moiety locates the enzymatic portion to the desired site in the body of the patient (ie the site expressing the said VGSC, such as metastatic cancer cells) and after allowing time for the enzyme to localise at the site, administering a prodrug which is a substrate for the enzyme, the end product of the catalysis being a cytotoxic compound. The object of the approach is to maximise the concentration of drug at the desired site and to minimise the concentration of drug in normal tissues (see Senter, P. D. et al (1988) "Antitumor effects of antibody-alkaline phosphatase conjugates in combination with etoposide phosphate" *Proc. Natl. Acad. Sci. USA* 85, 4842-4846; Bagshawe (1987) *Br. J. Cancer* 56, 531-2; and Bagshawe, K. D. et al (1988) "A cytotoxic agent can be generated selectively at cancer sites" *Br. J. Cancer.* 58, 700-703.)

Clearly, any said VGSC-binding moiety may be used in place of an anti-said VGSC antibody in this type of directed enzyme prodrug therapy system.

The enzyme and prodrug of the system using a said VGSC-targeted enzyme as described herein may be any of those previously proposed. The cytotoxic substance may be any existing anti-cancer drug such as an alkylating agent; an agent which intercalates in DNA; an agent which inhibits any key enzymes such as dihydrofolate reductase, thymidine synthetase, ribonucleotide reductase, nucleoside kinases or topoisomerase; or an agent which effects cell death by interacting with any other cellular constituent. Etoposide is an example of a topoisomerase inhibitor.

Reported prodrug systems include: a phenol mustard prodrug activated by an *E. coli* β-glucuronidase (Wang et al, 1992 and Roffler et al, 1991); a doxorubicin prodrug activated by a human β-glucuronidase (Bosslet et al, 1994); further doxorubicin prodrugs activated by coffee bean α-galactosidase (Azoulay et al, 1995); daunorubicin prodrugs, activated by coffee bean α-D-galactosidase (Gesson et al, 1994); a 5-fluorouridine prodrug activated by an *E. coli* β-D-galactosidase (Abraham et al, 1994); and methotrexate prodrugs (eg methotrexate-alanine) activated by carboxypeptidase A (Kuefner et al, 1990, Vitols et al, 1992 and Vitols et al, 1995). These and others are included in the following table.

| Enzyme | Prodrug |
|---|---|
| Carboxypeptidase G2 | Derivatives of L-glutamic acid and benzoic acid mustards, aniline mustards, phenol mustards and phenylenediamine mustards; fluorinated derivatives of these |
| Alkaline phosphatase | Etoposide phosphate Mitomycin phosphate |
| Beta-glucuronidase | p-Hydroxyaniline mustard-glucuronide Epirubicin-glucuronide |
| Penicillin-V-amidase | Adriamycin-N phenoxyacetyl |
| Penicillin-G-amidase | N-(4'-hydroxyphenyl acetyl) palytoxin Doxorubicin and melphalan |
| Beta-lactamase | Nitrogen mustard-cephalosporin p-phenylenediamine; doxorubicin derivatives; vinblastine derivative-cephalosporin, cephalosporin mustard; a taxol derivative |
| Beta-glucosidase | Cyanophenylmethyl-beta-D-glucopyranosiduronic acid |
| Nitroreductase | 5-(Azaridin-1-yl-)-2,4-dinitrobenzamide |
| Cytosine deaminase | 5-Fluorocytosine |
| Carboxypeptidase A | Methotrexate-alanine |

(This table is adapted from Bagshawe (1995) *Drug Dev. Res.* 34, 220-230, from which full references for these various systems may be obtained; the taxol derivative is described in Rodrigues, M. L. et al (1995) *Chemistry & Biology* 2, 223).

Suitable enzymes for forming part of the enzymatic portion of the invention include: exopeptidases, such as carboxypeptidases G, G1 and G2 (for glutamylated mustard prodrugs), carboxypeptidases A and B (for MTX-based prodrugs) and aminopeptidases (for 2-α-aminocyl MTC prodrugs); endopeptidases, such as eg thrombolysin (for thrombin prodrugs); hydrolases, such as phosphatases (eg alkaline phosphatase) or sulphatases (eg aryl sulphatases) (for phosphylated or sulphated prodrugs); amidases, such as penicillin amidases and arylacyl amidase; lactamases, such as β-lactamases; glycosidases, such as β-glucuronidase (for β-glucuronomide anthracyclines), α-galactosidase (for amygdalin) and β-galactosidase (for β-galactose anthracycline); deaminases, such as cytosine deaminase (for 5FC); kinases, such as urokinase and thymidine kinase (for gancyclovir); reductases, such as nitroreductase (for CB1954 and analogues), azoreductase (for azobenzene mustards) and DT-diaphorase (for CB1954); oxidases, such as glucose oxidase (for glucose), xanthine oxidase (for xanthine) and lactoperoxidase; DL-racemases, catalytic antibodies and cyclodextrins.

The prodrug is relatively non-toxic compared to the cytotoxic drug. Typically, it has less than 10% of the toxicity, preferably less than 1% of the toxicity as measured in a suitable in vitro cytotoxicity test.

It is likely that the moiety which is able to convert a prodrug to a cytotoxic drug will be active in isolation from the rest of the compound but it is necessary only for it to be active when (a) it is in combination with the rest of the compound and (b) the compound is attached to, adjacent to or internalised in target cells.

When each moiety of the compound is a polypeptide, the two portions may be linked together by any of the conventional ways of cross-linking polypeptides, such as those generally described in O'Sullivan et al (1979) *Anal. Biochem.* 100, 100-108. For example, the said VGSC binding moiety may be enriched with thiol groups and the further moiety reacted with a bifunctional agent capable of reacting with those thiol groups, for example the N-hydroxysuccinimide ester of iodoacetic acid (NHIA) or N-succinimidyl-3-(2-pyridyldithio)propionate (SPDP). Amide and thioether bonds, for example achieved with m-maleimidobenzoyl-N-hydroxysuccinimide ester, are generally more stable in vivo than disulphide bonds.

Alternatively, the compound may be produced as a fusion compound by recombinant DNA techniques whereby a length of DNA comprises respective regions encoding the two moieties of the compound of the invention either adjacent one another or separated by a region encoding a linker peptide which does not destroy the desired properties of the compound. Conceivably, the two portions of the compound may overlap wholly or partly.

The DNA is then expressed in a suitable host to produce a polypeptide comprising the compound of the invention.

The cytotoxic moiety may be a radiosensitizer. Radiosensitizers include fluoropyrimidines, thymidine analogues, hydroxyurea, gemcitabine, fludarabine, nicotinamide, halogenated pyrimidines, 3-aminobenzamide, 3-aminobenzodiamide, etanixadole, pimonidazole and misonidazole (see, for example, McGinn et al (1996) *J. Natl. Cancer Inst*. 88, 1193-11203; Shewach & Lawrence (1996) *Invest. New Drugs* 14, 257-263; Horsman (1995) *Acta Oncol*. 34, 571-587; Shenoy & Singh (1992) *Clin. Invest*. 10, 533-551; Mitchell et al (1989) *Int. J. Radiat. Biol*. 56, 827-836; Iliakis & Kurtzman (1989) *Int. J. Radiat. Oncol. Biol. Phys*. 16, 1235-1241; Brown (1989) *Int. J. Radiat. Oncol. Biol. Phys*. 16, 987-993; Brown (1985) *Cancer* 55, 2222-2228).

Also, delivery of genes into cells can radiosensitise them, for example delivery of the p53 gene or cyclin D (Lang et al (1998) *J. Neurosurg*. 89, 125-132; Coco Martin et al (1999) *Cancer Res*. 59, 1134-1140).

The further moiety may be one which becomes cytotoxic, or releases a cytotoxic moiety, upon irradiation. For example, the boron-10 isotope, when appropriately irradiated, releases a particles which are cytotoxic (see for example, U.S. Pat. No. 4,348,376 to Goldenberg; Primus et al (1996) *Bioconjug. Chem*. 7, 532-535).

Similarly, the cytotoxic moiety may be one which is useful in photodynamic therapy such as photofrin (see, for example, Dougherty et al (1998) *J. Natl. Cancer Inst*. 90, 889-905).

The further moiety may comprise a nucleic acid molecule which is directly or indirectly cytotoxic. For example, the nucleic acid molecule may be an antisense oligonucleotide which, upon localisation at the target site is able to enter cells and lead to their death. The oligonucleotide, therefore, may be one which prevents expression of an essential gene, or one which leads to a change in gene expression which causes apoptosis.

Examples of suitable oligonucleotides include those directed at bcl-2 (Ziegler et al (1997) *J. Natl. Cancer Inst*. 89, 1027-1036), and DNA polymerase a and topoisomerase IIα (Lee et al (1996) *Anticancer Res*. 16, 1805-1811.

Peptide nucleic acids may be useful in place of conventional nucleic acids (see Knudsen & Nielsen (1997) *Anticancer Drugs* 8, 113-118).

In a further embodiment, the binding moiety may be comprised in a delivery vehicle for delivering nucleic acid to the target, for example a nucleic acid as discussed in relation to earlier aspects of the invention. The delivery vehicle may be any suitable delivery vehicle. It may, for example, be a liposome containing nucleic acid, or it may be a virus or virus-like particle which is able to deliver nucleic acid. In these cases, the moiety which selectively binds to the said VGSC is typically present on the surface of the delivery vehicle. For example, the moiety which selectively binds to the said VGSC, such as a suitable antibody fragment, may be present in the outer surface of a liposome and the nucleic acid to be delivered may be present in the interior of the liposome. As another example, a viral vector, such as a retroviral or adenoviral vector, is engineered so that the moiety which selectively binds to the said VGSC is attached to or located in the surface of the viral particle thus enabling the viral particle to be targeted to the desired site. Targeted delivery systems are also known, such as the modified adenovinis system discussed above.

Immunoliposomes (antibody-directed liposomes) may be used in which the moiety which selectively binds to the said VGSC is an antibody. The preparation of immunoliposomes is described above.

The nucleic acid delivered to the target site may be any suitable DNA which leads, directly or indirectly, to cytotoxicity. For example, the nucleic acid may encode a ribozyme which is cytotoxic to the cell, or it may encode an enzyme which is able to convert a substantially non-toxic prodrug into a cytotoxic drug (this latter system is sometime called GDEPT: Gene Directed Enzyme Prodrug Therapy).

Ribozymes which may be encoded in the nucleic acid to be delivered to the target are described in references cited above. Suitable targets for ribozymes include transcription factors such as c-fos and c-myc, and bcl-2. Durai et al (1997) *Anticancer Res*. 17, 3307-3312 describes a hammerhead ribozyme against bcl-2.

EP 0 415 731 describes the GDEPT system. Similar considerations concerning the choice of enzyme and prodrug apply to the GDEPT system as to the ADEPT system described above.

The nucleic acid delivered to the target site may encode a directly cytotoxic polypeptide.

In a further embodiment of the invention, the further moiety comprised in the compound of the invention is a readily detectable moiety.

By a "readily detectable moiety" we include the meaning that the moiety is one which, when located at the target site following administration of the compound of the invention into a patient, may be detected, typically non-invasively from outside the body and the site of the target located. Thus, the compounds of this embodiment of the invention are useful in imaging and diagnosis.

Typically, the readily detectable moiety is or comprises a radioactive atom which is useful in imaging. Suitable radioactive atoms include technetium-99m or iodine-123 for scinitgraphic studies. Other readily detectable moieties include, for example, spin labels for magnetic resonance imaging (MRI) such as iodine-123 again, iodine-131, indium-111, fluorine-19, carbon-13, nitrogen-15, oxygen-17, gadolinium, manganese or iron. Clearly, the compound of the invention must have sufficient of the appropriate atomic isotopes in order for the molecule to be readily detectable.

The radio- or other labels may be incorporated in the compound of the invention in known ways. For example, if the binding moiety is a polypeptide it may be biosynthesized or may be synthesized by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker er al (1978) *Biochem. Biophys. Res. Comm*. 80, 49-57) can be used to incorporate iodine-123. Reference ("Monoclonal Antibodies in Immunoscintigraphy", J-F Chatal, CRC Press, 1989) describes other methods in detail.

In a further preferred embodiment of the invention the further moiety is able to bind selectively to a directly or indirectly cytotoxic moiety or to a readily detectable moiety. Thus, in this embodiment, the further moiety may be any moiety which binds to a further compound or component which is cytotoxic or readily detectable.

The further moiety may, therefore be an antibody which selectively binds to the further compound or component, or it may be some other binding moiety such as streptavidin or biotin or the like. The following examples illustrate the types of molecules that are included in the invention; other such molecules are readily apparent from the teachings herein.

The further moiety may be or comprise a bispecific antibody wherein one binding site comprises the moiety which selectively binds to the said VGSC and the second binding site comprises a moiety which binds to, for example, an enzyme which is able to convert a substantially non-toxic prodrug to a cytotoxic drug.

The compound may be an antibody which selectively binds to the said VGSC, to which is bound biotin. Avidin or streptavidin which has been labelled with a readily detectable label may be used in conjunction with the biotin labelled antibody in a two-phase imaging system wherein the biotin labelled antibody is first localised to the target site in the patient, and then the labelled avidin or streptavidin is administered to the patient. Bispecific antibodies and biotin/streptavidin (avidin) systems are reviewed by Rosebrough (1996) *Q J Nucl. Med.* 40, 234-251.

In a preferred embodiment of the invention, the moiety which selectively binds to the said VGSC and the further moiety are polypeptides which are fused.

A further aspect of the invention comprises a nucleic acid molecule encoding a compound of the preceding aspect of the invention.

A further aspect of the invention provides a compound of the invention for use in medicine. Typically, the compound is packaged and presented as a medicament or as an imaging agent or as a diagnostic agent for use in a patient.

A still further aspect of the invention provides a pharmaceutical composition comprising a compound according to the invention and a pharmaceutically acceptable carrier.

Typically the pharmaceutical compositions or formulations of the invention are for parenteral administration, more particularly for intravenous administration.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

A still further aspect of the invention provides the use of a compound of the invention in the manufacture of a medicament for the treatment and/or diagnosis of a human patient with or at risk of cancer, preferably breast cancer.

A still further aspect of the invention comprises a method of treating cancer (preferably breast cancer) the method comprising administering to the human patient an effective amount of a compound of the invention wherein the further moiety of the compound is one which either directly or indirectly is of therapeutic benefit to the patient.

A still further aspect of the invention comprises a method of imaging cancer, preferably breast cancer, (which may be useful in determining the susceptibility of a human patient to cancer, or of diagnosing cancer in a human patient, or of predicting the relative prospects of a particular outcome of a cancer) in a human patient, comprising administering to the patient an effective amount of a compound of the invention wherein the further moiety of the compound is one which comprises a readily detectable moiety.

A still further aspect of the invention provides the use of a compound comprising a moiety which selectively binds a voltage-gated $Na^+$ channel protein, preferably SCN5A or SCN9A, most preferably SCN5A, and a further moiety (as defined above) in the manufacture of a medicament for the treatment and/or diagnosis of a human patient with or at risk of breast cancer.

A still further aspect of the invention comprises a method of treating breast cancer, the method comprising administering to the human patient an effective amount of a compound comprising a moiety which selectively binds a voltage-gated $Na^+$ channel protein, preferably SCN5A or SCN9A, most preferably SCN5A, and a further moiety (as defined above) wherein the further moiety of the compound is one which either directly or indirectly is of therapeutic benefit to the patient.

A still further aspect of the invention comprises a method of imaging breast cancer in a human patient, comprising administering to the patient an effective amount of a compound comprising a moiety which selectively binds a voltage-gated $Na^+$ channel protein, preferably SCN5A or SCN9A, most preferably SCN5A, and a further moiety (as defined above) wherein the further moiety of the compound is one which comprises a readily detectable moiety.

It will readily be appreciated that, depending on the particular compound used in treatment, imaging or diagnosis, the timing of administration may vary and the number of other components used in therapeutic systems disclosed herein may vary.

For example, in the case where the compound (for example compound of the invention) comprises a readily detectable moiety or a directly cytotoxic moiety, it may be that only the compound, in a suitable formulation, is administered to the patient. Of course, other agents such as immunosuppressive agents and the like may be administered.

In respect of compounds which are detectably labelled, imaging takes place once the compound has localised at the target site.

However, if the compound is one which requires a further component in order to be useful for treatment, imaging or diagnosis, the compound of the invention may be administered and allowed to localise at the target site, and then the further component administered at a suitable time thereafter.

For example, in respect of the ADEPT and ADEPT-like systems above, the binding moiety-enzyme moiety compound is administered and localises to the target site. Once this is done, the prodrug is administered.

Similarly, for example, in respect of the compounds wherein the further moiety comprised in the compound is one which binds a further component, the compound may be administered first and allowed to localise at the target site, and subsequently the further component is administered.

Thus, in one embodiment a biotin-labelled anti-SNC5A antibody (for example) is administered to the patient and, after a suitable period of time, detectably labelled streptavidin is administered. Once the streptavidin has localised to the sites where the antibody has localised (ie the target sites) imaging takes place.

It is believed that the compounds of the invention wherein the further moiety is a readily detectable moiety may be useful in determining the metastatic state of cancer cells. This may be an important factor influencing the nature and outcome of future therapy.

A further aspect of the invention provides a kit of parts (or a therapeutic system) comprising (1) a compound of the invention wherein the further moiety is a cytotoxic moiety which is able to convert a relatively non-toxic prodrug into a cytotoxic drug and (2) a relatively non-toxic prodrug. The kit of parts may comprise any of the compounds of the invention and appropriate prodrugs as herein described.

A still further aspect of the invention provides a kit of parts (or a therapeutic system) comprising (1) a compound of the invention wherein the further moiety is able to bind selectively to a directly or indirectly cytotoxic moiety or to a readily detectable moiety and (2) any one of a directly or indirectly cytotoxic moiety or a readily detectable moiety to which the further moiety of the compound is able to bind.

For example, a kit of parts may contain an anti-SNC5A antibody labelled with biotin and streptavidin labelled with a readily detectable label as defined above.

The invention will now be described by reference to the following, non-limiting Example and Figures.

FIG. 1. Voltage-gated membrane currents recorded in (A) MDA-MB-231 cells and (B) MCF-7 cells (B). The currents were generated by pulsing the membrane potential from a holding voltage of −100 mV, in 10 mV steps, to +60 mV for 40 ms (A) and 200 ms (B), respectively. Voltage pulses (indicated by the arrow-heads) were applied with a repeat interval of 20 s. Only every second current trace generated is displayed. (C) A typical current-voltage (I-V) relationship generated in MDA-MB-231 cells by pulsing the membrane potential from a holding voltage of −100 mV to test potentials between −70 to +70 mV in 5 mV increments. Voltage pulses were applied with a repeat interval of 20 s.

Figure 2:
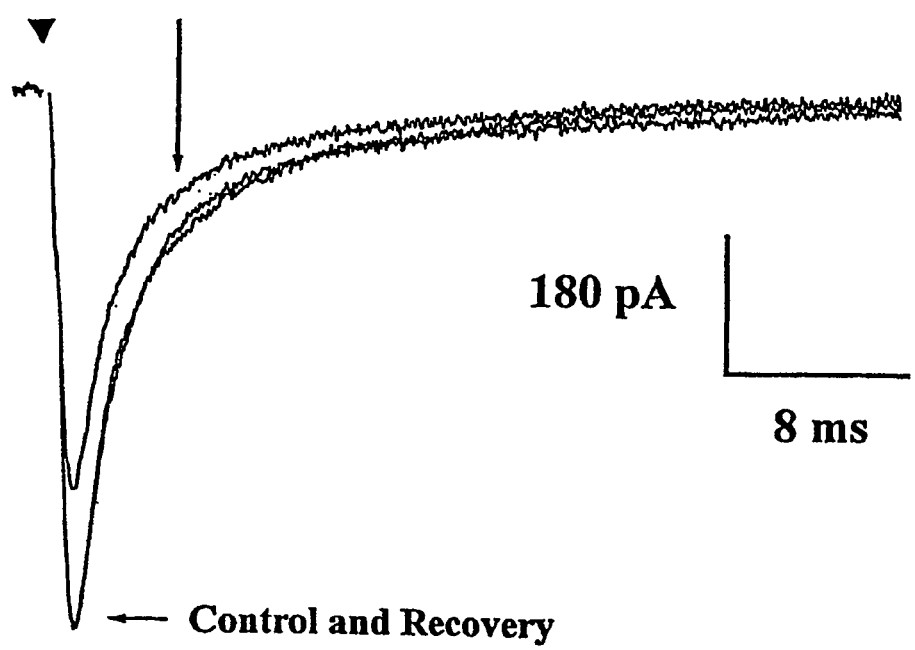
Figure 2:
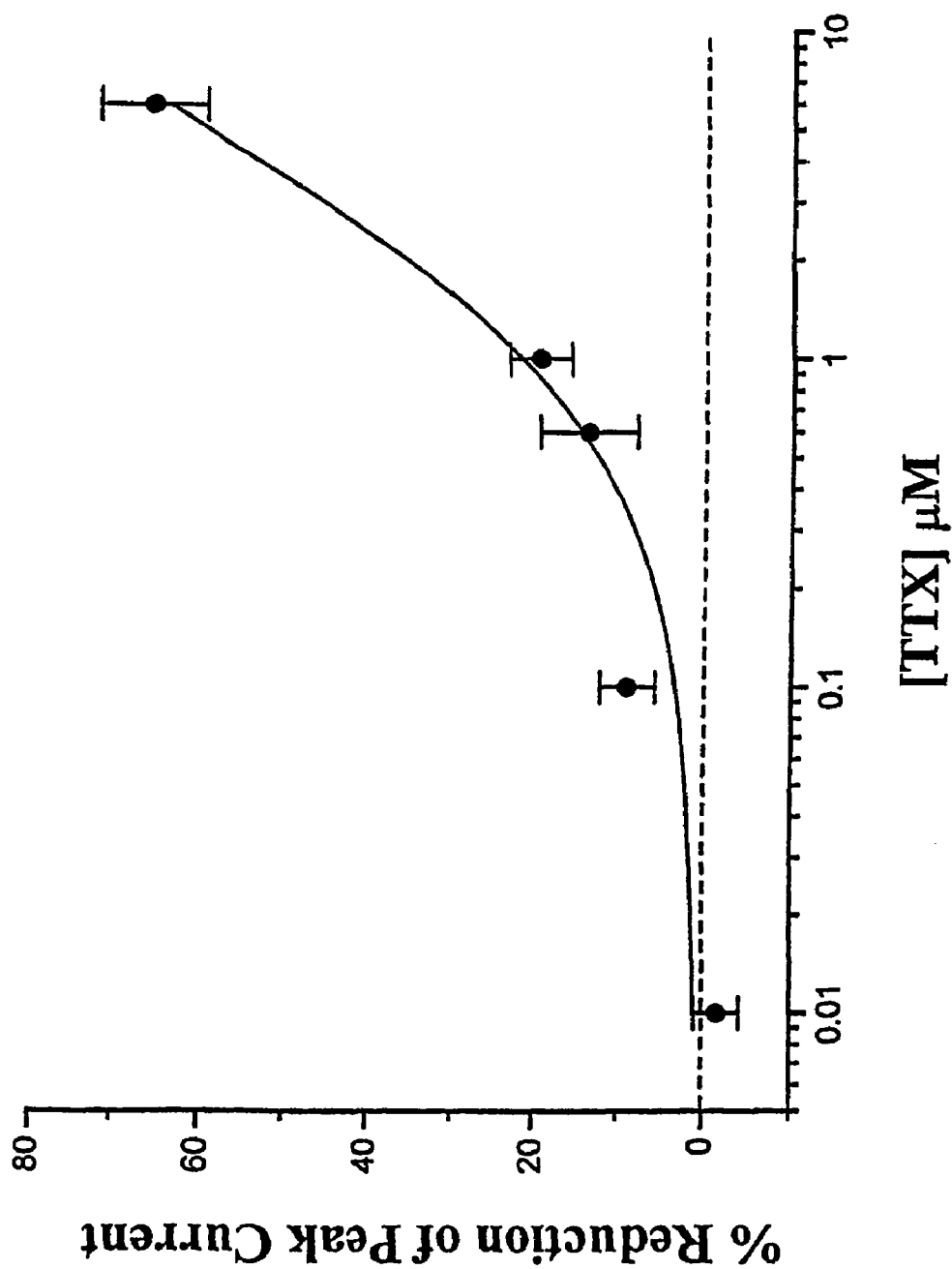

FIG. 2. Suppression of the inward current in MDA-MB-231 cells by tetrodotoxin (TTX). (A) A typical recording showing the effect of 1 μM TTX; the suppression effect, which was partial, was fully reversible. The currents were generated by pulsing the membrane potential from a holding voltage of −mV to −10 mV for 40 ms. Voltage pulses (indicated by the arrow-head) were applied with a repeat interval of 20 s. The effect of TTX shown resulted from the fourth pulse following drug application. (B) TTX dose-response curve for MDA-MB-231 cells. Cells were depolarised from −100 mV to −10 mV for 40 ms with a repeat interval of 20 s. The percentage reduction of the peak current at the fourth pulse following TTX application, was plotted as a function of drug concentration. Each point represents the mean of >5 different cells; error bars denote standard errors. Dotted line denotes 0% reduction.

Figure 3:
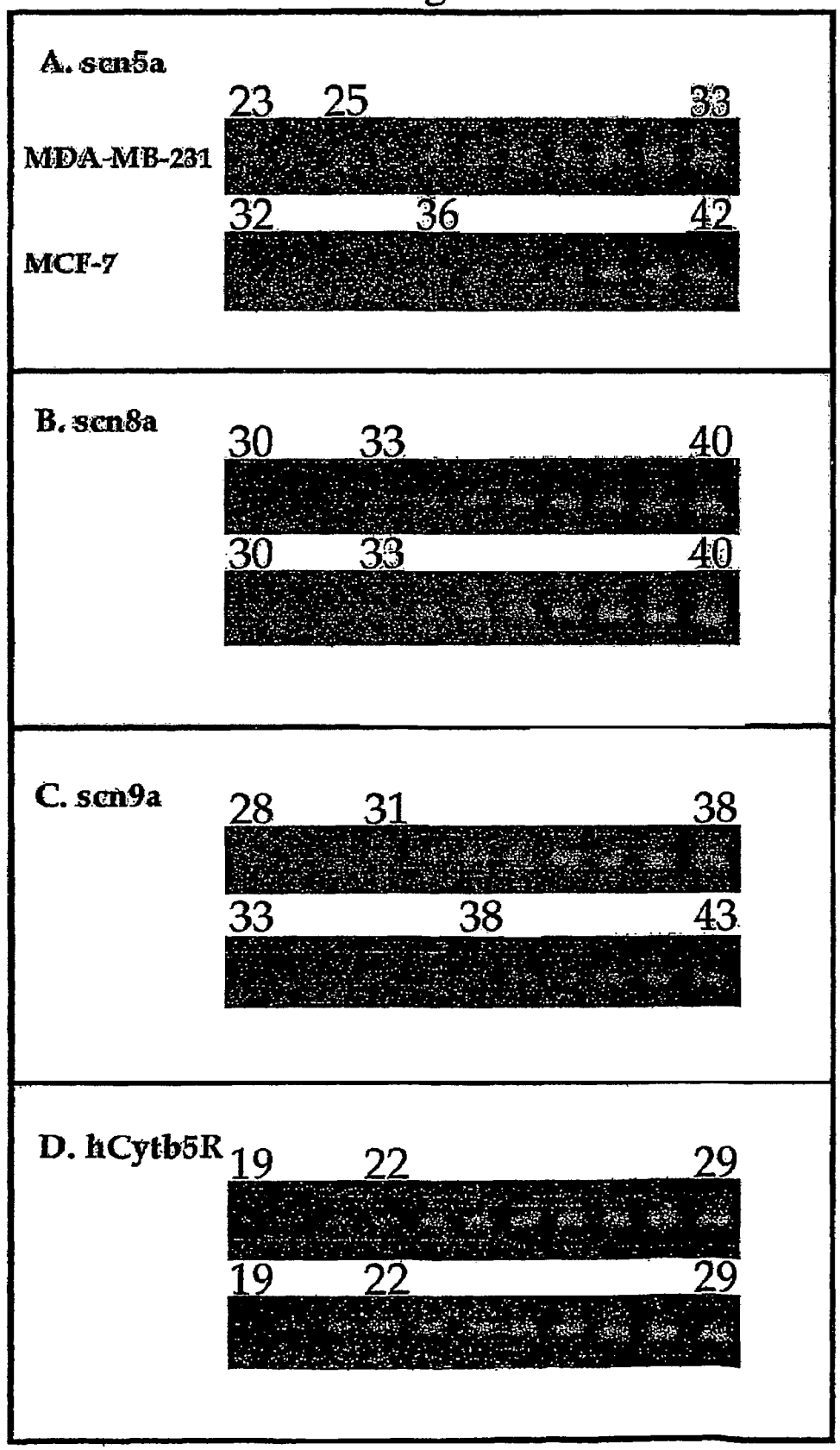

FIG. 3. SQT-PCR electrophoresis results for scn5a (A), scn8a (B), scn9a (C) and hCytb5R (D). Representative PCR cycle numbers for given bands are indicated above the gels. In each panel, the top image was derived from MDA-MB-231 cell extracts; the bottom image, from MCF-7 extracts, as indicated in (A).

Figure 4:
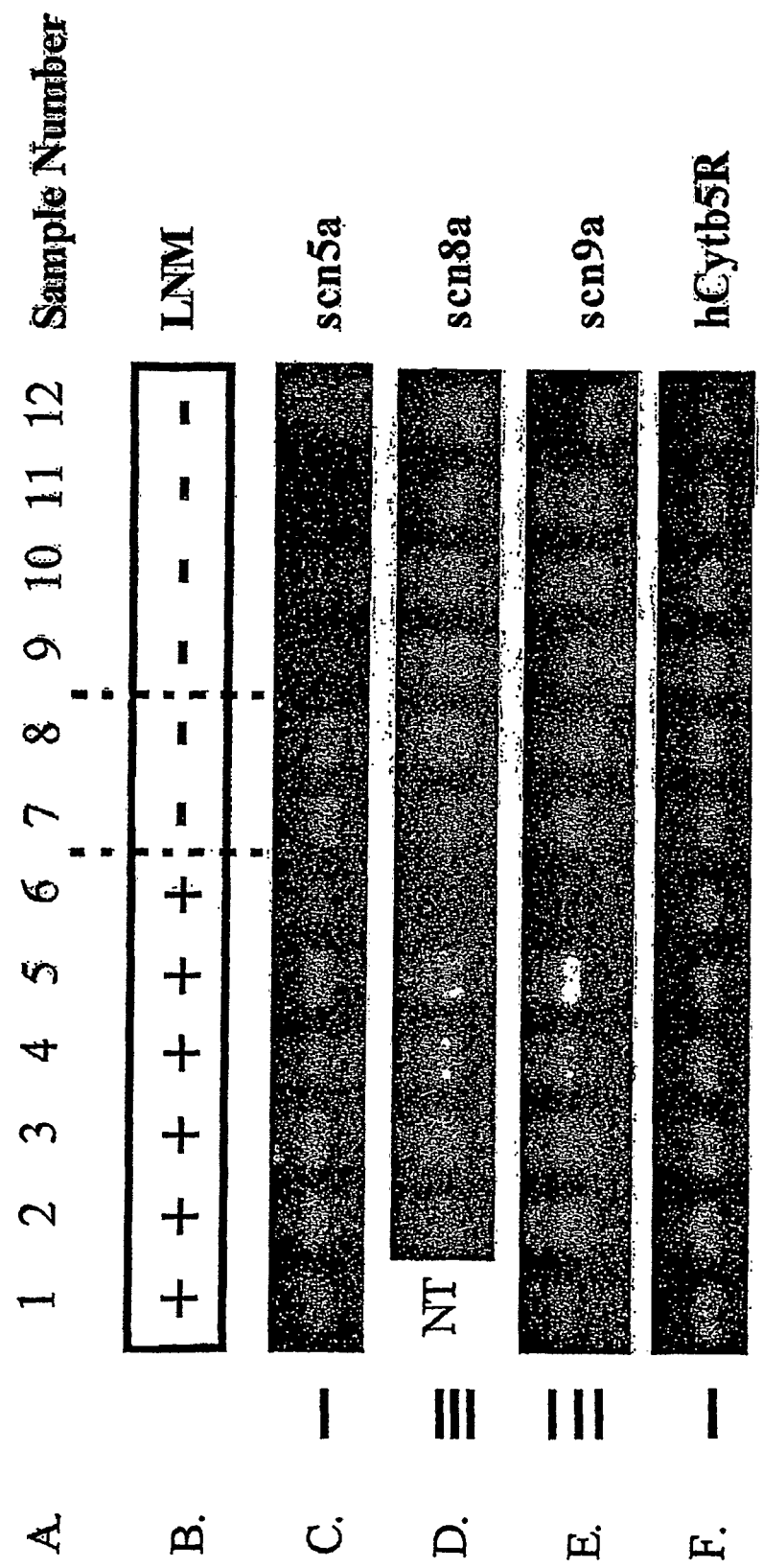

FIG. 4. Electrophoresis results of scn5a (C), scn8a (D), scn9a (E) and hCytb5R (F) RT-PCRs performed on breast cancer tissue samples. Sample numbers and associated evident lymph node metastasis (LNM) are indicated above the gel images (A and B). Multiple bands corresponding to the evident splice form products (previously described in reference [21]) are shown to the left. PCRs were performed for 55, 40, 40 and 30 cycles for scn5A, scn8a, scn9a and hCytb5R tests, respectively, except for samples 5 (scn8a and scn9a, 50 cycles each) and 6 (hCytb5R, 40 cycles). (+) indicates evident LNM, (−) indicates that LNM was not clinically evident. NT=not tested.

Figure 5:
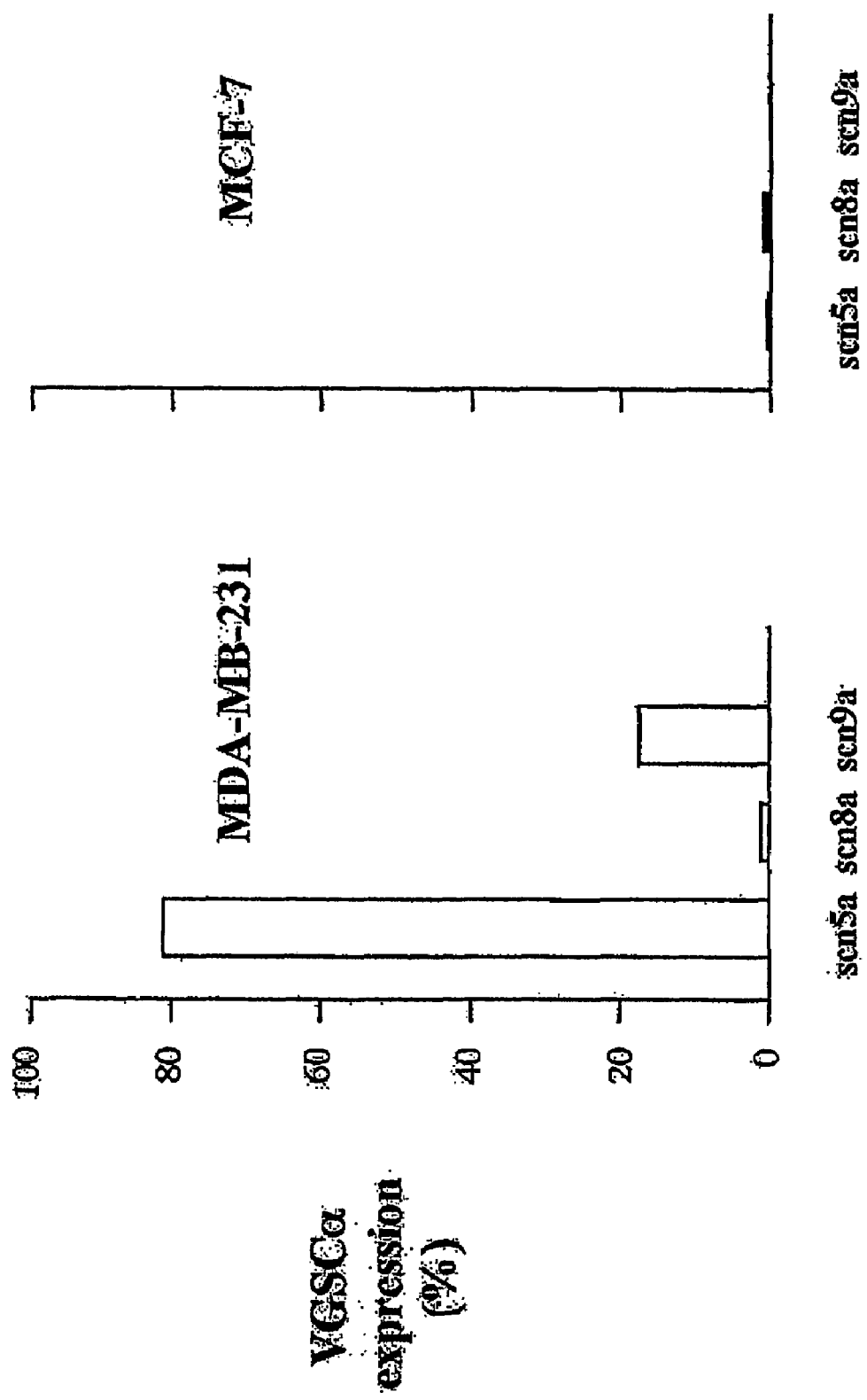

FIG. 5. Proposed relative (%) expression levels of the three VGSCαs found to occur in the strongly (white bars) and weakly (black bars) metastatic cell lines. In each case, the vertical axis denotes the approximate level of expression with respect to total levels of expression of these three VGSCαs in the strongly metastatic MDA-MB-231 cells. Relative expression levels were estimated from degenerate screens and SQT-PCR data, taken together.

EXAMPLE 1

Upregulation of Voltage-Gated Na$^+$ Channel Expression and Metastatic Potential in Human Breast Cancer: Correlative Studies on Cell Lines and Biopsy Tissues Voltage-gated Na$^+$ channel (VGSC) expression in human breast cancer cell lines and breast cancer tissues was studied by electrophysiological and reverse-transcription polymerase chain reaction (RT-PCR) methods in a correlative approach. Whole-cell patch-clamp recordings revealed depolarisation-activated Na$^+$ currents in 29% of the strongly metastatic MDA-MB-231 cell line, but never in the weakly metastatic MCF-7 cells. These currents were largely tetrodotoxin (TTX)-resistant. The expression of three VGSC α subunit (VGSCα) genes, SCN5A, SCN8A and SCN9A was determined in both cell lines. Two of these genes (SCN5A and SCN9A) were found to be more highly expressed in the MDA-MB-231 cells, with semi-quantitative RT-PCRs indicating the relative levels of expression as: scn5a>>scn9a>scn8a. The predominant increase in the expression of scn5a (~1800-fold), also termed h1 or SkM2, which indeed yields TTX-resistant VGSCs, was largely responsible for the greater level of VGSCα expression in the strongly metastatic cells. RT-PCRs performed on breast cancer tissues in a double-blind test showed a strong correlation between the detection of SCN5A gene products and clinically assessed lymph node metastasis. Thus, all biopsies with evident lymph node metastases expressed scn5a; the reverse situation was also mainly true. We conclude that VGSC upregulation occurs as an integral part of the metastatic process in breast cancer, as in prostate cancer, and could serve as a novel marker of the metastatic phenotype.

BACKGROUND

Breast cancer is the third most common cancer world wide and the most common cancer of women, affecting 1 in 8 in the western world (1,2). In the USA, breast cancer is the second leading cause of female cancer mortality accounting for about 10% of all cancer deaths (3). In breast cancer, as in other cancers, metastasis is the main cause of death in most patients. To date, several breast cancer metastasis-associated genes have been identified (for review, see reference 2). However, indirect measures of metastatic progression, including assessment of intratumoral vascular invasion, presence or absence of lymph node involvement and size of the primary carcinoma remain the most widely used methods for the assessment of breast cancer progression. Electro-diagnosis has also been practised, although its cellular/molecular basis remains unknown (4).

We have shown previously that the functional expression of a voltage-gated Na$^+$ channel (VGSC) can distinguish strongly and weakly metastatic human and rat prostatic cancer cells (5,6) and that VGSC activity contributes to cellular behaviours integral to metastasis, including cellular process extension (7), lateral motility (8), transverse invasion (5,6,9) and secretory membrane activity (10). Carcinomas of the breast and prostate have some similar features, including hormone-sensitivity, a pronounced tropism for metastasis to bone and tendency for co-occurrence in families (11).

Voltage-gated Na$^+$ channels (VGSCs)[1] are composed of a large (≈240 kD), four-transmembrane domain α-subunit (VGSCα) and several different auxiliary β-subunits (VGSCβs) (Catterall, W. A. (1986) Ann. Rev. Biochem. 55, 953-

985). Expression of the VGSCα alone is sufficient for functional channel formation (Goldin, A. L et al (1986). Proc. Natl. Acad. Sci USA 83, 7503-7507). The VGSCβ(s) serve a number of supporting roles such as facilitating functional channel availability (Isom, L. L., et al (1995) Cell 83, 433-442), modulating channel kinetics (Isom, L. L., et al (1992) Science 256, 839-842, Cannon, S. C., et al (1993) Pflugers Arch. 423, 155-157) and perhaps even altering pharmacological characteristics (Bonhaus, D. W., et al (1996) Neuropharmacol. 35, 605-613) (see also (15)).

VGSCαs constitute a family of at least twelve different genes in higher vertebrates (Plummer, N. W. and Meisler, M. H. (1998) Genomics 57, 323-331; 17), denoted SCN1A to SCN11A; their products have been cloned from a variety of excitable cell types. Their specific expressions are under dynamic, spatio-temporal control. At least two subfamilies of VGSCα genes have been described based on sequence data: $Na_v1$ and $Na_v2$ (George, A. L., et al (1992) Proc. Natl. Acad. Sci. USA 89, 4893-4897). Although not yet experimentally determined, it is generally held that these subfamilies represent VGSCαs with markedly different electro-physiological properties (Akopian, A. N., et al (1997) FEBS Letts. 400, 183-187). In fact the lack of conservation of landmark VGSCα sequences in $Na_v2$ VGSCαs implies that they may not even be voltage-gated or $Na^+$ selective (Akopian, A. N., et al (1997) FEBS Letts. 400, 183-187, Schlief, T., et al (1996) Eur. Biophys. J. 25, 75-91). The existence of a third subfamily, $Na_v3$, has recently been proposed with the cloning of a cDNA (NaN/SNS2) from rat dorsal root ganglion (DRG) cells. Although NaN/SNS2 shares less than 50% sequence homology with other VGSCαs, its deduced amino acid sequence possesses all the characteristic sequences of $Na_v1$ VGSCαs (Dib-Hajj, S. D, et al (1998) Proc. Natl. Acad. Sci. USA 95, 8963-8968).

By utilizing RT-PCR and in situ hybridization methods, several studies have documented the simultaneous expression of multiple VGSCαs within diverse cell types (Black, J. A., et al (1994) Mol. Brain Res. 23, 235-245; Dib-Hajj, S. D., et al (1996) FEBS Letts. 384, 78-82; Fjell, J., et al (1999) Mol. Brain Res. 67, 267-282). Particular VGSCαs have been found to be expressed at different levels, with expression under dynamic control (e.g. during development or injury). For example, mRNAs for at least eight different VGSCαs were found in adult rat DRG cells, with a wide range of expression levels: RB1, Na6, NaN/SNS2 and SCL-11 mRNAs were expressed at very high levels, PN1 and SNS/PN3 at intermediate levels, and RB2 and RB3 at very low levels (Dib-Hajj, S. D, et al (1998) Proc. Natl. Acad. Sci. USA 95, 8963-8968; Black, J. A., et al (1996) Molec. Brain Res. 43, 117-131; Sangameswaren, L., et al (1997) J. Biol. Chem. 272, 14805-14809). Following axonal injury SNS and NaN/SNS2 mRNAs were dramatically down-regulated, whilst expression of RB1, RB2 and RB3 was up-regulated (Dib-Hajj, S., et al (1996) Proc. Natl. Acad. Sci. USA 93, 14950-14954; Dib-Hajj, S. D., et al (1998) J. Neurophysiology 79, 2668-2676).

VGSCα genes can occur as a number of alternatively spliced isoforms, expression of which is also under dynamic control. Alternative splicing of exons coding for the third segment (S3) of the first transmembrane domain (D1) has been found to be developmentally regulated for SCN2A and SCN3A (19, 20), yielding "neonatal" and "adult" forms. These code for proteins which differ by only one amino acid, positioned at the extreme extracellular end of S3. The effect of this change on VGSCα function is presently unclear. Similar alternatively spliced exons exist at the corresponding position in SCN8A and SCN9A (Belcher, S. M et al (1995) Proc. Natl. Acad. Sci. USA 92, 11034-11038; Plummer, N. W., et al (1998) Genomics 54, 287-296) but not in SCN4A, SCN5A, SCN10A and SCN11A (George, A. L., et al (1993) Genomics 15, 598-606; Wang, D. W., et al (1996) Biophys. J. 70, 238-245; Souslova, V. A., et al (1997) Genomics 41, 201-209; Dib-Hajj, S. D., et al (1999) Genomics 59, 309-318). To date, no evidence of such alternative splicing has been found for SCN1A or SCN7A. Alternative splicing also occurs in other regions of the VGSCα, particularly inter-domain (ID) 1-2 and D3.

The strict regulation of multiple VGSCα gene and splice product expression within the available VGSCα mRNA pool, among different tissue types and during development or following injury (e.g. Dib-Hajj, S., et al (1996) Proc. Natl. Acad. Sci. USA 93, 14950-14954; Dib-Hajj, S. D., et al (1998) J. Neurophysiology 79, 2668-2676; Kallen, R. G., et al (1990) Neuron 4, 233-242) would suggest that different VGSCα gene products and their isoforms are likely to have significantly different functional roles, which, at present, are largely unknown.

The functional roles of VGSCs are best understood in the central nervous system where VGSC activity controls not only basic impulse generation and conduction but also directional and patterned growth, including target-specific axonal migration and regional synaptic connectivity (Catalano, S. M. and Shatz, C. J. (1998) Science 281, 559-562; Penn, A. A., et al (1998) Science 279, 2108-2112; Shatz, C. J. (1990) Neuron 5, 745-756). VGSCs have also been implicated in several hereditary diseases of excitable tissues (Plummer, N. W. and Meisler, M. H. (1998) Genomics 57, 323-331; Zhou, J. and Hoffman, E. P. (1994) J. Biol. Chem. 269, 18563-18571), and in more complicated pathological disorders, including chronic pain syndromes (Tanaka, M., et al (1998) NeuroReport 9, 967-972), epilepsy (Bartolomei, F., et al (1997) J. Neurocytol. 26, 667-678), ischaemic stroke (Skaper, S. D., et al (1998) FASEB J. 12, 725-731) and Alzheimer's disease (Kanazirska, M., et al (1997) Biochem. Biophys. Res. Comm. 232, 84-87). There is increasing evidence that VGSC expression is also associated with strong metastatic potential in rat (MAT-LyLu) and human (PC-3) models of prostate cancer (Grimes, J. A., et al (1995) FEBS Letts. 369, 290-294; Laniado, M., et al (1997) Am. J. Pathol. 150, 1213-1221; Smith, P., et al (1998) FEBS Letts 423, 19-24). Indeed, expression of functional VGSCs may have a direct, positive influence upon the metastatic process. Accordingly, blockage of VGS currents in these strongly metastatic cell lines, by application of tetrodotoxin (TTX), significantly (~30%) reduced the cells' invasive potential. Electro-physiological and pharmacological properties of the current in the rat were consistent with the channels being neuronal, TTX-sensitive ($Na_v1$) type (Grimes, J. A. and Djamgoz, M. B. A. (1998) J. Cell. Physiol. 175, 50-58). SCN4A gene expression was found in both strongly and weakly metastatic cell lines of human and rat (Diss, J. K. J., et al (1998) FEBS Letts 427, 5-10). However, the pharmacological properties of the VGS currents in the rat MAT-LyLu cells were not consistent with those reported for this VGSCα. This could result from (1) the numerous differences determined in the MAT-LyLu/AT-2 rSkM1 primary sequence; (2) differences in post-translational mechanisms (eg association with auxiliary subunits, level of glycosylation/phosphorylation of the channel) in these cells; or (3) the presence of other VGSCαs in the MAT-LyLu cells that produce the recorded VGS currents.

The present study aimed to determine (i) whether mRNA and functional protein expression of VGSCs differed between strongly and weakly metastatic breast cancer cells; (ii) which member(s) of the VGSCα family was responsible for the voltage-gated $Na^+$ (VGS) currents detected; and (iii) whether the VGSCα expression pattern found in in vitro models would also be reflected in human breast cancer biopsy tissues. These aspects were studied using electrophysiological and reverse-transcription polymerase chain reaction (RT-PCR) based techniques. Initially, two robust breast cancer cell lines of contrasting metastatic aggressiveness were adopted: the strongly metastatic MDA-MB-231 cells and the weakly metastatic MCF-7 cells (18,19). The mRNA(s) responsible for the functional VGSC α-subunit expression was determined. Finally, VGSC mRNA expression was also investigated in frozen biopsy tissues of different clinical grade to test whether VGSCα occurrence could also be correlated with cancer progression in vivo.

Materials and Methods

Cell culture. MDA-MB-231 and MCF-7 cells were grown and maintained in Dulbecco's modified Eagle's medium (Life Technologies Ltd, Paisley, UK) supplemented with 4 mM L-glutamine and 10% foetal bovine serum. Cells were seeded into 100 mm Falcon tissue culture dishes (Becton Dickinson Ltd, Plymouth, UK) and grown in an incubator at 37° C., 100% humidity and 5% $CO_2$.

Electrophysiology. Patch pipettes (of normal resistances between 5-15 MΩ) were filled with a solution containing (in mM) NaCl 5, KCl 145, $MgCl_2$ 2, $CaCl_2$ 1, HEPES 10 and EGTA 11, adjusted to pH 7.4 with 1 M KOH. Whole-cell membrane currents were recorded from cells that appeared 'isolated' in culture using an Axopatch 200B (Axon Instruments) amplifier. Analogue signals were filtered at 5 KHz using a low-pass Bessel filter. Signals were sampled at 5 KHz and digitised using a Digidata (1200) interface. Data acquisition and analysis of whole-cell currents were performed using pClamp (Axon Instruments) software. Holding potentials of −90 mV or −100 mV were used to study $K^+$ and $Na^+$ currents, respectively, unless stated otherwise. Resting potentials were measured immediately following attainment of the 'whole-cell' recording configuration. Experiments on both MDA-MB-231 and MCF-7 cells were performed on three separate dishes which had been plated for between 1-3 days.

Two basic command voltage protocols were used to study the electrophysiological and pharmacological properties of the Na+ and $K^+$ currents, as follows:

1. Current-voltage (1-V) protocol. This protocol was used to study the voltage-dependence of $Na^+$ and $K^+$ channel activation. Cells were pulsed to depolarising test potentials between −70 and +60 mV, in 5 mV steps. The test pulse duration was 40 ms ($Na^+$ currents) or 200 ms ($K^+$ currents); the interpulse period was 20 s.
2. Repeat single-pulse protocol. This was used to monitor the effects of drugs on current amplitude. Test pulses were to −10 mV ($Na^+$ currents) or +60 mV ($K^+$ currents). The test pulse duration was 40 ms ($Na^+$ currents) or 200 ms ($K^+$ currents); the interpulse duration was 20 s and there were 5 repeat pulses.

Pharmacology. Tetrodotoxin (TTX), purchased from Alomone Labs Ltd (Jerusalem, Israel), was made as a stock solution (×1000) in the external bath solution, frozen at −20° C., defrosted and diluted as required. Briefly, TTX was back-loaded into a glass capillary (with a tip size of ˜5 μm). The glass capillary was then connected to a pneumatic picopump (PV 800, WP Instruments), mounted on a microdrive (Lang-Electronik, Huttenberg, Germany) and manoeuvred to within ˜10 μm of the cell under investigation.

The effect of TTX on the inward current (1) has been presented as the percentage block of current (B) in comparison to the control values, calculated as follows:

$$B(\%)=[(I_{after}-I_{before})/I_{before}] \times 100$$

VGSCα degenerate primer screens. Total cellular RNA was isolated from two batches of each of the cell lines by the acid guanidium thiocyanate-phenol-chloroform method (20) or as described below. Briefly, cells were homogenized in a solution ("A"), using an IKA homogeniser, such that 1 ml of solution was used per 0.1 g of tissue. Solution A contained 4 M guanidinium thiocyanate, 25 mM $Na^+$ citrate (pH 7.0), 0.5% sarcosyl and 0.72% (v/v) β-mercaptoethanol. The following were then added and shaken vigorously for 10 seconds: 2 M $Na^+$ acetate, pH 4.0 (10% volume of solution A), phenol (equal volume of solution A) and chloroform (20% volume of solution A). Centrifugation was performed at 10,000×g for 20 mins at 4° C. The supernatant was taken and precipitated with isopropanol. Then, the samples were centrifuged as before and the pellet was resuspended in about 30% of the initial volume of solution A. A second isopropanol precipitate was performed, the pellet was washed with 75% ethanol, and resuspended in sterile distilled water.

Screens were then performed on each of the four extracts, as described previously (21 and GB 0021617.6, supra), using VGSCα degenerate PCR primers, YJ1 and YJ2C (Table 1A).

Twenty five clones with "inserts" were selected by gel electrophoresis for each of the RNA extracts. A subset of the twenty five clones with inserts, derived from each cell line, were then sequenced using the Amersham Thermo Sequenase fluorescent cycle sequencing kit and the Vistra DNA 725 automated sequencer. Sequences were identified by searching the GenBank DNA database using BLAST 2.0.8 (22). Oligonucleotide primers specific for scn5a and scn9a VGSCαs, identified by the sequencing, were subsequently designed (Table 1A). These worked in conjunction with the Universal vector primers and permitted rapid PCR screening of all other clones without the need for sequencing. PCRs using these primers were initially tested on sequenced clones to confirm that they yielded only specific products. Rapid screening PCR reactions were then performed as in (21) and GB 0021617.6, supra. Products were analysed by gel electrophoresis on 0.8% agarose gels. Minipreps that did not test positive for these VGSCαtypes were sequenced to determine identity.

TABLE 1

PCR primers used in (A) degenerate VGSCα primer screening, (B) specific PCRs and (C) SQT-PCRs (numbering according to GenBank). Primer annealing positions are indicated in parentheses.

A. Degenerate VGSCα Primer Screening

YJ1: -5' GCGAAGCTT(C/T)TGG(C/T)TIATITT(C/T)I(A/C/G/T)IAT(A/T/C)AT GGG 3'
(SEQ ID NO 7)

YJ2C: -5' ATAGGATCCAICCI(A/C/G/T)I(A/G)AAIGC(A/C/G/T)AC(C/T)TG 3' (40° C.)
(SEQ ID NO 8)

Scn5a-P1: -5' TACAATTCTCCGGTCAAGTT 3' (4312-4331; 56° C.)
(SEQ ID NO 9)

TABLE 1-continued

PCR primers used in (A) degenerate VGSCα primer screening,
(B) specific PCRs and (C) SQT-PCRs (numbering according to GenBank).
Primer annealing positions are indicated in parentheses.

```
Scn9a-P1:  -5' ATGTTAGTCAAAATGTGCGA 3' (4139-4158; 54° C.)
(SEQ ID NO 10)
```

B. Specific PCR Tests

```
Scn5a-P2:  -5' CATCCTCACCAACTGCGTGT 3' (570-589)
(SEQ ID NO 11)

Scn5a-P3:  -5' CACTGAGGTAAAGGTCCAGG 3' (1059-1078; 58° C.)
(SEQ ID NO 12)

Scn8a-P1:  -5' AGACCATCCGCACCATCCTG 3' (3855-3874)
(SEQ ID NO 13)

Scn8a-P2:  -5' TGTCAAAGTTGATCTTCACG 3' (4351-4370; 60° C.)
(SEQ ID NO 14)

Scn9a-P2:  -5' TATGACCATGAATAACCCGC 3' (474-493)
(SEQ ID NO 15)

Scn9a-P3:  -5' TCAGGTTTCCCATGAACAGC 3' (843-862; 59° C.)
(SEQ ID NO 16)

hCytb5R-P1: -5' TATACACCCATCTCCAGCGA 3' (299-318)
(SEQ ID NO 17)

hCytb5R-P2: -5' CATCTCCTCATTCACGAAGC 3' (771-790; 60° C.)
(SEQ ID NO 18)
```

C. SQT-PCRs

```
Scn5a-P4:  -5' CTGCTGGTCTTCTTGCTTGT 3' (2896-2915)
(SEQ ID NO 19)

Scn5a-P5:  -5' GCTGTTCTCCTCATCCTCTT 3' (3329-3348; 60° C.)
(SEQ ID NO 20)

Scn8a-P3:  -5' AACCCTATTCCGAGTCATCC 3' (3827-3846)
(SEQ ID NO 21)

Scn8a-P4:  -5' TGCACTTTCCTCTGTGGCTA 3' (4325-4344; 60° C.)
(SEQ ID NO 22)

Scn9a-P4:  -5' AAGGAAGACAAAGGGAAAGA 3' (5941-5960)
(SEQ ID NO 23)

Scn9a-P5:  -5' TCCTGTGAAAAGATGACAAG 3' (6289-6308; 56° C.)
(SEQ ID NO 24)
```

VGSCα-specific PCR tests. These were performed, as in (21) and GB 0021617.6 in order to ensure that the VGSCαs found in the degenerate primer screens were truly expressed in the respective cell lines (and not produced from contaminating genomic DNA).

Briefly, DNA was removed from the extracts by digestion with DNase 1 and 5 μg of the total RNA was used as the template for single-stranded cDNA (sscDNA) synthesis (Superscript II, GIBCO BRL). sscDNA synthesis was primed with a random hexamer mix (R6) in a final volume of 20 μl. VGSCα cDNA was then amplified from the R6-sscDNA pool by PCR (Taq DNA polymerase, Amersham Pharmacia) using degenerate PCR primers (YJ1 and YJ2C) used previously to amplify both $Na_v1$ and $Na_v2$ VGSCαs from adult rat retinal pigment epithelial cells (Dawes, H., et al (1995) Vis. Neurosci. 12, 1001-1005), and novel VGSCαs from a protochordate ascidian (Okamura, Y., et al (1994) Neuron 13, 937-948). PCR reactions were performed on 4 μl of the R6-sscDNA template, using 200 μM of each dNTP, 1 unit of Taq, 1×Taq buffer and 1 μM of each primer, in a final volume of 20 μl. Amplification was via: (i) initial denaturation at 94° C. for 5 min; (ii) addition of 1 U enzyme; (iii) 33-35 cycles of denaturation at 94° C. for 1 min, annealing at 40° C. for 1 min, and elongation at 72° C. for 1 min; and (iv) elongation at 72° C. for 10 min. For this and all PCRs performed, reactions with no sscDNA added were also carried out to control for cross-contamination from other DNA sources.

PCR products were analysed by electrophoresis and gel purified prior to ligation into the pGEM-T vector (pGEM-T Easy Vector System, Promega). These were then used to transform E. coli (pMosBlue, Amersham). Plasmid DNA was recovered from bacterial cultures using a modified version of the Vistra Labstation 625 miniprep procedure (Vistra DNA Systems, Amersham).

Reactions designed to amplify specific VGSCαs were performed on both strongly and weakly metastatic cell line extracts, irrespective of whether these subunits had previously been found in degenerate screens. The primer sequences and reaction annealing temperatures used are shown in Table 1B. Evident products were cloned and sequenced, and a consensus sequence for each VGSCα in each cell line then produced (using at least three clones).

Semi-quantitative PCR (SQT-PCR). SQT-PCRs based on kinetic observation of reactions were performed similarly to (21) and GB 0021617.6.

DNased RNA extracts were used to produce sets of R6-sscDNAs for each extract. 2.4 µl of these k6-sscDNAs was used as the template for VGSCα-specific PCRs (performed as above), in a final volume of 60 µl. To allow direct comparison of results obtained from strongly and weakly metastatic cell lines, all comparable R6-sscDNA and PCR reactions were performed simultaneously. 'Blanks', with no template added, were used as controls. PCRs were performed using different 20-mer primers for each of the three VGSCαs which did not amplify multiple VGSCα products derived from different splice variants (unlike the specific PCRs above). The primers and annealing temperatures of the PCRs used are shown in Table 1C. scn8a and scn9a VGSCα products did not span conserved intron sites so control PCR reactions were performed for these SQT-PCRs in which the sscDNA template was replaced by an aliquot from a reverse transcription reaction which had no reverse transcriptase added. All products were cloned and sequenced, as above, to ensure that only VGSCα-specific products were amplified.

A kinetic observation approach (45; Hoof et al (1991) *Anal. Biochem.* 196, 161-169; Wiesner et al (1992) *Biochem. Biophys. Res. Comm.* 183, 553-559) was adopted such that an aliquot of 5 µl from the 60 µl reaction was taken at the end of each amplification cycle, for eleven cycles, while reactions were held at 72° C. The amplification cycle at which aliquots were first taken differed depending on the VGSCα studied. These aliquots were then electrophoresed (0.8% agarose gels) with DNA markers of known concentration. Gels were post-stained for 15 minutes (TBE buffer containing 0.8 µg/ml ethidium bromide), and digitally imaged (GDS 7500 Advanced Gel Documentation System, Ultra-Violet Products). Total product mass (nanograms) in each aliquot was determined by image analysis (1D Image Analysis Software, Kodak Digital Science). Two characteristic stages in each PCR reaction were quantified:

(1) Threshold PCR cycle number ($CN_t$) at which a given PCR product could just be detected by the image analysis software (default settings).

(2) PCR cycle number at which the exponential phase of the reaction finished ($CN_e$).

Accumulation of reaction product with increasing PCR cycle number follows a sigmoid curve (Kohler, T. (1995). *Quantitation of mRNA by Polymerase Chain Reaction*, pp 3-14, eds. Kohler, T., Lassner, D., Rost, A.-K., Thamm, B., Pustowoit, B. and Remke, H. (Springer, Heidelberg)). However, the two extremes of this curve were unknown or undetermined for the SQT-PCR data (i.e. the initial mass of cDNA at zero cycles was unknown, and the final product mass at the end of the PCR undetermined). Thus, a sigmoid curve could not be fitted to the data. Instead a third-order polynomial equation, which also has only one possible point of inflexion (here corresponding to the end of the exponential phase of the PCR), was used to approximate a sigmoid curve. Curve-fitting was performed using STATISTICA (SoftStat Inc.), and the second derivative then calculated, to give $CN_e$. This procedure could be performed successfully, with the calculated values of $CN_e$ falling within the data points obtained experimentally (FIG. 1). Data are presented as means and standard errors for each cell line (three repeats on two extracts for each VGSCα). The values of $CN_t$ and $CN_e$ were used directly to compare the levels of expression of each VGSCα in the strongly and weakly metastatic cell lines.

Mean CNt values were calculated for each of the VGSCαs present in MDA-MB-231 and MCF-7 cell extracts using the results of SQT-PCRs on both cell batches (except for scn9a, amplified from only one of the two MCF-7 cell line batches, and scn5A, which was apparently expressed too lowly in one MCF-7 batch for CNe to be calculated). Assuming that the PCR reactions performed on strongly and weakly metastatic cell RNA extracts had similar efficiencies, differences in the calculated CNt and CNe values would reflect real differences in expression levels.

NADH-cytochrome b5 reductase ($Cytb_5R$), which is expressed at very similar levels in normal, cancerous and strongly metastatic cells derived from numerous tissue types (20; Fitzsimmons, S. A., et al (1996) J. Natl. Cancer Inst. 88, 259-269; Marin, A., et al (1997) Br. J. Cancer 76, 923-929), was present in both rat and human degenerate primer screens as a major constituent of the non-specific products found (the "non-VGSCα" clones). Consequently, this was used as a control amplicon in SQT-PCRs, ie to control for the effects of variations in quality and quantity of the initial RNA, efficiency of the reverse-transcription and amplification between samples (primers are shown in Table 1B). $Cytb_5R$ 20-mer primers amplified nucleotides 385-809 and 299-790 of rat and human homologues, respectively (annealing temperature, 60° C. for both).

PCR tests on breast biopsy tissue. 0.1-0.5 g pieces of frozen tissue were chopped into small pieces using a sterile scalpel and forceps and placed in a cold, glass homogenizer. Total cellular RNA was then isolated as described above. RNA quality was preliminarily assessed by gel electrophoresis and quantity determined by spectrophotometric analysis.

RNA extracts were then used as the template for sscDNA synthesis, performed as above. The possible expression of scn5A, scn8a and scn9a RNAs in the biopsy samples was tested by PCR, using the same primers as for the specific PCRs (Table 1B). hCytb5R specific PCR tests were also carried out to further control for the quality of the extracted RNA; samples which did not yield evident hCytb5R products were rejected. PCRs were performed, using 2.5 µl of the synthesised sscDNA, 0.2 millimolar dNTPs, 1 micomolar of each specific primer and 1 unit of Taq, under the following conditions: 94° C. for 5 min; 1 U enzyme added; 94° C. for 1 min; 59-62° C. for 1 min (depending on the primer pair); 72° C. 1 min; final incubation at 72° C. for 10 min with the main section repeated 30-60 times (depending on the primer pair). PCR reactions with no template added were also performed to control for cross-contamination from other DNA sources. 5 µl aliquots of the final reaction were analysed by gel electrophoresis on 0.8% agarose gels.

PCR tests were carried out on each of at least two cDNA templates (except for sample 1, from which only 5 µg of RNA was obtained), manufactured independently from the same RNA extract, thus controlling for possible variability in cDNA manufacture and PCR efficiency.

Data analysis. All quantitative data were determined to be normally distributed and are presented in the text as means±standard errors. Statistical significance was determined with Student's t test or $\chi^2$ test, as appropriate.

GenBank sequence nucleotide numbers. Nucleotide numbering was according to accession numbers M77235, AB027567, X82835, Y09501 for scn5a, scn8a, scn9a and hCytb5R, respectively.

Results

Electrophysiological studies. The average resting potential of MDA-MB-231 cells was −18.9±2.1 mV (n=27; range −12 to −61 mV) which was significantly more depolarised than the value of −38.9±2.5 mV (n=26; range −8 to −51 mV) for the MCF-7 cells (p<0.001). The membrane capacitance of the MDA-MB-231 cells was 28.5±2.7 pF (n=35; range 14.7 to 76.6 pF) which was significantly smaller than the value of 36.9±2.8 pF (n=38; range 13.5 to 90.0 pF) for the MCF-7 cells (p<0.05).

29% of the MDA-MB-231 cells tested (n=16/56) expressed an inward current of up to 600 pA in amplitude (FIG. 1A), which corresponded to a current density of 5.6±0.5 pA/pF (n=16). The inward currents activated at 41.3±2.4 mV (n=4), peaked at −6.3 2.4 mV (n=4; FIG. 1C) and were abolished in $Na^+$-free medium (not shown; n=2), consistent with them being VGS currents. In contrast, none of the MCF-7 cells tested (n=72) showed an inward current (FIG. 1B).

The VGS current was suppressed partially by micromolar TTX (FIG. 2A). The effect of the toxin was concentration dependent in the range 100 nM-6 μM (FIG. 2B). However, even at the highest concentration used (6 μM), only 64.7±6.1% of the current was blocked by TTX (n=5). There was a small (9±3%) reduction in peak current with 100 nM TTX, which was significant (p<0.05), indicating that a minor, TTX-sensitive (TTX-S) component was also present (FIG. 2B).

Voltage-gated outward currents were also recorded. 100% of the MCF-7 cells tested (n=72) expressed large outward currents of up to 7 nA in amplitude (FIG. 1B), which corresponded to a current density of 27.4±4.9 pA/pF (n=33). These outward currents activated at −9.2±1.9 mV (n=12) and showed a peak amplitude of 1081.1±264.7 pA at +90 mV (n=12). The current was reduced to 34.3+5.4 pA (n=15; p<0.01), i.e. by 97%, by substituting $Cs^+$ for $K^+$ in the internal pipette solution. In comparison, MDA-MB-231 cells showed much smaller outward currents of up to 150 pA (n=35; FIG. 1B), which corresponded to a current density of only 2.6±0.4 pA/pF (n=13; p<0.01 cf. comparable currents recorded in the MCF-7 cells).

VGSCα mRNA expression in the cell lines. The results of the degenerate-primer screens for the different cell line RNA extracts are shown in Table 2. Two VGSCαs were identified in the screens on the strongly metastatic cell line: products of SCN5A and SCN9A VGSCα genes. In contrast, scn8a was the only VGSCα found in the degenerate screens of the weakly metastatic MCF-7 cells. It has previously been shown that for Nav1 VGSCαs, the proportion of clones in degenerate primer screens representing each VGSCα type reflects the actual proportion of that subunit within the cellular VGSCα mRNA pool (21). Thus, in the strongly metastatic cells, screen results indicated that scn5a (56.0±4.0%) was expressed at a much greater level than scn9a (12.0±4.0%) and scn8a (0%) (Table 2).

TABLE 2

Summary of the VGCSα degenerate primer screen results. Results are shown as percentage of clones tested (n = 25 in each case). Each screen is the result of two extracts from each cell line. Errors indicate standard errors.

| VGSCα | MDA-MB-231 | MCF-7 |
|---|---|---|
| Scn5a | 56.0 ± 4.0 | 0 |
| Scn8a | 0 | 2.0 ± 2.0 |
| Scn9a | 12.0 ± 4.0 | 0 |
| Non - VGSCα | 32.0 ± 0 | 98.0 ± 2.0 |

Primer-specific PCRs yielded products for scn5, scn8a and scn9a (as well as for hCytb5R) in both cell lines, indicating that all of these mRNAs were expressed in both MDA-MB-231 and MCF-7 cells. However, scn5a and scn9a required markedly less amplification (CNt) to yield detectable products and reach CNe in SQT-PCRs on MDA-MB-231 vs. MCF-7 cell extracts, indicating an overall greater level of expression in the strongly metastatic cells (FIGS. 3A and 3C). Importantly, the most striking, consistent difference was seen for SCN5A: CNt=24.75±0.48 vs. 37.50±1.56; CNe=28.36±0.46 vs. 38.54±0.14, for MDA-MB-231s vs. MCF-7 cells, respectively (FIG. 3A). Assuming an 80% PCR efficiency (21), this would indicate $^-$1800-fold difference in expression levels between the two cell lines.

Scn9a was more readily amplified in the strongly metastatic (CNt=30.75±0.63; CNe=34.44±0.65) than the weakly metastatic cells (CNt=42.5±4.5; CNe=46.0±3.2), but this TTX-S VGSCα was not as prominent as scn5a in degenerate screens, indicating a lower level of expression. In contrast, hCytb5R 'control' and scn8a SQT-PCRs showed very similar levels of expression in both MDA-MB-231 and MCF-7 cells (FIGS. 3B and 3D): CNt=20.25±0.25 vs. 22.0±0.56, CNe=23.96±1.00 vs. 25.16±0.34, for hCytb5R; CNt=33.25±0.25 vs. 32.75±0.63, CNe=36.85±0.32 vs. 35.61±0.49, for scn8a. Importantly, hCytb5R was the major constituent of the 'non-VGSCα' clones found in the degenerate screens, representing almost all of the non-VGSCα clones (equivalent to 28.0±0% of all clones) in the MDA-MB-231 cells and 54.0±6.0% of all the clones in the MCF-7 cell line screen. The increased incidence of this non-VGSCα clone in the degenerate screens of the MCF-7 cells is consistent with a lower VGSCα target to noise ratio in these cells compared to their strongly metastatic counterpart, also evident from the SQT-PCR data.

The MDA-MB-231/MCF-7 VGSCα sequences obtained have been submitted to GenBank.

VGSCα mRNA expression in breast biopsy tissue. RNA was extracted successfully, with positive hCytb5R tests obtained, from 12 samples. Generally, PCR results of the VGSCα and hCytb5R control tests were readily repeatable across different synthesised cDNA batches. The results obtained are summarised in Table 3. All three VGSCα genes found to be expressed in the cell lines were detected in the biopsy samples, confirming the conservation in vivo of the VGSCα expression profile of the in vitro models. Several SCN8A and SCN9A products (corresponding to different splice forms of these genes; (21)) were amplified from all samples (FIGS. 4D and E), as was the hCytb5R control (FIG. 4F), except in sample 6. It is likely that the RNA extracted from this sample was significantly more degraded than the other samples, as evidenced by the greater number of PCR cycles required to amplify the hCytb5R control product (40 not 30 cycles). There was, however, no evident correlation between scn8a or scn9a expression and lymph node metastasis (LNM). In contrast, expression of scn5a was strictly sample-dependent (FIGS. 4A and B). All evident products of these tests were cloned and sequenced, and it was verified that these products were truly derived from SCN5A. Scn5a is VGSCα sequences obtained from these samples have been submitted to GenBank.

Accession numbers of submitted sequences are as follows:
Accession#: AJ310882
Description: *Homo sapiens* partial mRNA for voltage-gated sodium channel
Nav1.7 (SCN9A gene) cell line MDA-MB-231
Accession#: AJ310883
Description: Homo sapiens partial mRNA for Nav1.7 voltage-gated-sodium
channel (SCN9A gene) cell line MCF-7
Accession#: AJ310884

Description: *Homo sapiens* mRNA for Nav1.6 voltage-gated-sodium (SCN8A gene) Nav1.6, D3 neonatal splice variant, cell lines MDA-MB-231
Accession#: AJ310885

Description: *Homo sapiens* partial mRNA for voltage-gated sodium channel Nav1.6 (SCN8A gene), D3 neonatal splice variant, cell line MCF-1
Accession#: AJ310886

Description: *Homo sapiens* partial mRNA for voltage gated sodium channel Nav1.5 (SCN5A gene), D1 neonatal splice variant, cell line MDA-MB-231
Accession#: AJ310887

Description: *Homo sapiens* partial mRNA for voltage-gated sodium channel Nav1.5 (SCN5A gene) D1 neonatal splice variant, cell line MCF-7
Accession#: AJ310888

Description: *Homo sapiens* partial mRNA for voltage gated sodium channel Nav1.5 (SCN5A gene), D1 neonatal splice variant, biopsy sample 2
Accession#: AJ310889

Description: *Homo sapiens* partial mRNA for voltage-gated sodium channel Nav1.5 (SCN5A gene), D1 neonatal splice variant, biopsy sample 3
Accession#: AJ310890

Description: *Homo sapiens* partial mRNA for voltage-gated sodium channel Nav1.5 (SCN5A gene) D1 adult splice variant, biopsy sample 1
Accession#: AJ310891

Description: *Homo sapiens* partial mRNA for voltage gated sodium channel Nav1.5 (SCN5A gene), D1 adult splice variant, biopsy sample 7
Accession#: AJ310892

Description: *Homo sapiens* partial mRNA for voltage-gated sodium channel Nav1.5 (SCN5A gene), biopsy sample 6
Accession#: AJ310893

Description: *Homo sapiens* partial mRNA for voltage gated sodium channel Nav1.5 (SCN5A gene), D1:S3 exon-skipped splice variant, biopsy sample 8
Accession#: AJ310894

Description: *Homo sapiens* partial mRNA for voltage-gated sodium channel Nav1.5 (SCN5A gene), D1 neonatal splice variant, biopsy sample 4
Accession#: AJ310895

Description: *Homo sapiens* partial mRNA for Nav1.5 (scn5a/h1) voltage-gated sodium channel (SCN5A gene), D1 neonatal splice variant, biopsy sample 5
Accession#: AJ310896

Description: *Homo sapiens* partial mRNA for voltage-gated sodium channel Nav1.5 (SCN5A gene) (SCN5A gene), cell line MDA-MB-231
Accession#: AJ310897

Description: *Homo sapiens* partial mRNA for voltage-gated sodium channel Nav1.7 (SCN9A gene)(SCN9A gene), cell line MDA-MB-231
Accession#: AJ310898

Description: *Homo sapiens* partial mRNA for voltage-gated sodium channel Nav1.6 (SCN8A gene), cell line MCF-7
Accession#: AJ310899

Description: *Homo sapiens* partial mRNA for NADH-cytochrome b5 reductase (B5R gene) cell line MDA-MB-231
Accession#: AJ310900

Description: *Homo sapiens* partial mRNA for NADH-cytochrome b5 reductase (B5R gene) cell line MCF-7

Sequences have also been submitted for the following:
scn5a MDA-MB-231 SQT-PCR sequence
scn5a MCF-7 SQT-PCR sequence
scn9a MDA-MB-231 SQT-PCR sequence (3UTR)
scn9a MCF-7 SQT-PCR sequence (3UTR)

Some specific points regarding the SEQUENCE data:

SCN5A—Three nucleotide differences from the published sequence (GenBank M77235) in the sequence obtained outside the D1 neonatal exon: 689/690 (CT to GC) differences would substitute an alanine for a glycine residue at amino acid position 180 (all numbering according to M77235). All other voltage-gated sodium channel alpha subunit genes have a glycine at this residue, and thus it is most probable that the published sequence (M77235) contains sequence errors at this location. 992 (T to C) difference would not change the amino acid sequence and may represent a natural, silent-polymorphism in the SCN5A gene.

SCN8A—No nucleotide differences from our previously published sequences [SCN8A in prostate cancer cell lines] (GenBank AJ276141 and AJ276142).

SCN9A—No nucleotide differences from the published sequence (GenBank X82835).

The SCN5A D1 neonatal exon—this could be clinically important. This is the first report of the existence of an apparent alternative splice form of scna5a at this location. The SCN5A gene structure has been investigated previously (Wang et al., 1996), using scn5a cDNA sequences to probe a human genomic library but alternative exons for D1S3 were not found, presumably because the hybridizing cDNAs were of the known adult rather than the neonatal form. The scn5a neonatal form differs from the previously published adult form (Gellens et al., 1992; GenBank M77235) at 31 of the 92 nucleotides in this conserved exon. These 31 nucleotide differences in the neonatal SCN5A form result in 7 amino acid substitutions, many more than observed for the other VGSC alpha subunit genes studied thus far.

To date, alternative splicing of neonatal and adult exons has been found in D1S3 in four other VGSC alpha genes: SCN2A, SCN3A, SCN8A and SCN9A. In each of these instances the alternative exons have 19-21 nucleotide differences, which result in 1-2 amino acid substitutions. One amino acid substitution at residue seven of this exon is consistent across all of these genes: the substitution of an aspartate residue in the adult form to a neutral amino acid in the neonatal form. Alternative splicing in scn5a was not completely consistent with D1S3 splicing previously described for other VGSC alphas in two main ways:

(1) In the scn5a neonatal form, the aspartate residue in the adult form was not substituted for a non-charged amino acid, but a positively charged lysine residue.

(2) The 31 nucleotide differences in the neonatal scn5a result in 7 amino acid substitutions, many more than the 1-2 amino acid substitutions observed for the other VGSC alpha genes with alternative splicing at D1S3, previously studied.

TABLE 3

Summary of results of specific RT-PCR tests on breast cancer biopsy samples. (+) indicates that a specific product was obtained; (−) indicates that no specific product was amplified; NT that the test was not performed; ND that the grade of the tumour was not determined. PCR tests were performed for up to 55, 50 and 50 cycles for scn5a, scn8a and scn9a, respectively. hCytb5R tests were performed for 30 cycles except for sample 6, for which 40 cycles were used (denoted by *). Clinically assessment lymph node metastasis (LNM) and tumour grade are also shown for each case. For LNM (+), the values in parentheses indicate the number of lymph nodes which were determined as positive/number of nodes examined.

| Sample | Clinical Grade | hCytb5R | scn8a | scn9a | Scn5a | LNM |
|---|---|---|---|---|---|---|
| 1 | 2 | + | NT | + | + | +(4/4) |
| 2 | 3 | + | + | + | + | +(3/7) |
| 3 | 2 | + | + | + | + | +(3/7) |
| 4 | 2 | + | + | + | + | +(8/12) |
| 5 | ND | + | + | + | + | +(8/13) |
| 6 | 2 | +(*) | − | − | + | +(9/14) |
| 7 | 1 | + | + | + | + | −(0/22) |
| 8 | 2 | + | + | + | + | −(0/13) |
| 9 | 2 | + | + | + | − | −(0/15) |
| 10 | 3 | + | + | + | − | −(0/10) |
| 11 | 1 | + | + | + | − | −(0/15) |
| 12 | 3 | + | + | + | − | −(0/9) |

A 'double-blind' test associating scn5a expression with LNM revealed that these two characteristics were directly correlated in 10 out of the 12 (83%) cases examined, giving combinations of scn5a$^+$/LNM$^+$ (n=6) and scn5a$^-$/LNM$^-$ (n=4) ($\chi^2$=6.0; df=1; 0.02>p>0.01; Table 3). One of the two exceptions where the sample was scn5a+but apparently LNM$^-$ (sample 7) was interesting in that the patient subsequently relapsed, developing distant metastases within three years of the preliminary diagnosis. Whether relapse also occurred for the patient who provided the other exceptional case (sample 8) could not be determined.

Discussion

The present study shows (i) that strongly, but not weakly metastatic breast cancer cells displayed VGS currents, almost entirely composed of a TTX-resistant (ITX-R) component; (ii) that a particular TTX-R VGSCα gene, SCN5A, was predominantly expressed in strongly metastatic cells, but expressed at only very low levels in weakly metastatic cells; and (iii) that scn5a expression in biopsy samples correlated strongly with clinically assessed lymph node metastasis. Furthermore, the high-level VGSC expression was accompanied inversely by much reduced outward currents in the cell lines, and a relatively depolarised resting potential. Taken together, these characteristics would render metastatic cell membranes potentially 'excitable', consistent with their hyperactive behaviour.

Scn5a expression is associated with breast cancer metastasis. The electrophysiological and RT-PCR results demonstrated consistently that SCN5A gene products (also termed h1 or SkM2) were predominantly expressed in the strongly metastatic cell line (FIG. 5) and were associated with breast cancer metastasis in vivo. We have shown previously for human and/or rat prostate cancer cells that VGSC activity contributes to cellular behaviours integral to metastasis, including cellular process extension (7), lateral migration (8), transverse invasion (5,6,9) and secretory membrane activity (10). Subsequently, scn9a was identified as the 'culprit'

VGSCα (21). In the present study, the correlation of scn5a expression with increased cellular metastatic potential in vitro, and lymph node metastasis in vivo, would strongly indicate a significant role for scn5a activity in the metastatic behaviour of breast cancer cells.

Although the present study is the first to associate scn5a with cellular metastatic potential, others have previously reported expression of this VGSCα in cancer cell lines. Scn5a mRNA and functional protein expression have been shown to occur in B104 neuroblastoma cells (25) and RT4 peripheral neurotumour cancer cell lines (26,27). At present, it is not clear why strongly metastatic cells from carcinomas derived from different tissues should specifically upregulate the expression of different VGSCαs. Also, it is not known if, amongst the various VGSCαs, only scn5a would be capable of potentiating metastasis in breast carcinoma. If so, then it may be that this ability results from characteristics peculiar only to this VGSCα. Such possible, characteristic features of scn5a include the following: (i) Possession of C-terminal PDZ domains (28,29), potentially enabling particular interaction with the cytoskeleton; (ii) extremely low level of protein glycosylation (5% of the total protein mass, compared to up to 40% protein mass in other VGSCαs; (30)); (iii) highly promiscuous ion selectivity in given conditions, allowing $Ca^{2+}$ entry (31); (iv) very slow activation and inactivation kinetics (28,32); and (v) regulation of expression by steroid hormones (33).

Another notable characteristic of scn5a is that its expression appears to be under very tight spatio-temporal control and highly dynamic regulation. SCN5A gene products are classically expressed at very high levels in cardiac and neonatal/denervated skeletal muscle (29,34). However, Scn5a mRNA has also been detected in non-excitable, cultured spinal cord astrocytes (35) but not in a variety of cell types which express almost all other VGSCαs, like dorsal root ganglion neurones (26,36,37). Furthermore, in skeletal muscle particularly, significant changes in expression levels can occur over a period of only days after birth (34) and in response to denervation (38).

Conservation of breast cancer VGSCα expression in biopsy tissue. The profile of VGSCα expression in weakly and strongly metastatic breast cancer cells that we have obtained from the two cell lines (FIG. 5) is consistent with the results of the PCRs performed on the biopsy tissues. All three VGSCαs found in the cell lines were found to be expressed in the tissue samples and the expression of the predominant scn5a type was correlated strongly with the surgically characterised metastases.

Although relative expression levels of scn5a, scn8a and scn9a cannot directly be determined from the PCR tests, the apparent ease of amplification of the different VGSCαs from the biopsy tissues is consistent with the biopsy samples consisting almost entirely of a mass of essentially non-metastatic primary tumour cells with only a very small number of strongly metastatic cancer cells present in malignant tumours (e.g. 39,40). Thus, scn8a and scn9a (which are expressed at greater levels than Scn5a in weakly metastatic cells) could be detected in biopsy tissue using a lower number of PCR cycles, compared with scn5a, even from samples displaying evident lymph node metastasis.

The PCRs performed on the biopsy tissues did not yield reliable quantitative information concerning expression levels of the various VGSCαs, mainly due to the large variability in the quality of extracted RNA from one sample to another, as monitored by the control RNA. Scn5a expression was apparently so low in weakly metastatic cells that it could not be detected in non-malignant biopsy tissues. However, the expression, being greatly upregulated in the strongly metastatic cells within the biopsies, became readily detectable by PCR.

Multiplicity of VGSCα expression in breast cancer cell lines. The expression of multiple VGSCα genes was determined in both breast cancer cell lines and is consistent with the relative VGSCα expression profiles illustrated in FIG. 5. In brief, the level of scn8a was similar for both cell lines but very low, whilst expression of scn5a and scn9a were significantly greater for the MDA-MB-231 cell line. In particular, scn5a expression accounted for >80% of the VGSCαs in these cells. A D1 neonatal splice form of SCN5A may be of clinical importance, as discussed above. Multiplicity of VGSCα expression has also been found in rat and human prostate cancer cell lines of differing metastatic potential (21). The pharmacological data (TTX blockage) indicated that the VGS currents detected in the MDA-MB-231 cells were mainly TTX-R ($IC_{50}$>1 µM). This is consistent with the determined mRNA expression profile of these cells in which the TTX-R scn5a VGSCα is the predominant channel. The scn9a VGSCα expressed, but at much lower levels (FIG. 5), would yield TTX-S currents which could contribute to the TTX sensitivity observed at lower (100 nM) concentrations. Possible consequences of multiple VGSCα expression have been discussed previously (21). Interestingly, the full-length scn8a products detected in both strongly and weakly metastatic breast cancer cells were the neonatal splice form as determined by the product size (Diss, J. K. J., unpublished observation). This form of scn8a codes for a highly truncated VGSCα protein, and has been found to be preferentially expressed in neonatal and non-excitable adult tissues (41). Neonatal scn8a is thought not to be capable of creating functional VGSCs, instead acting as a "fail-safe" mechanism, preventing the functional expression of leakily expressed, non-truncated scn8a VGSCαs. The detection of neonatal scn8a mRNA in biopsy samples (as determined by the product size; FIG. 4D) indicates that this mechanism is also present in vivo.

VGSC expression in breast and prostate cancer: Comparative aspects. Many aspects of the findings of this study are similar to those determined using similar techniques in rat and human prostate cancer cell lines of differing metastatic potential (5,6,21): (i) the strongly metastatic cells had relatively depolarised resting potentials (6). (ii) VGS currents were detected in a sub-population of strongly metastatic cells (54% MAT-LyLu, 10% PC-3, 29% MDA-MB-231) and never detected in corresponding weakly metastatic cells (AT-2, LNCaP, MCF-7); (iii) VGSCα mRNA was detected in cells of both strong and weak metastatic potential, but with greater expression in strongly metastatic cells; (iv) multiple VGSCα expression was determined in all cells; (v) all cells expressed scn8a, mainly in the non-functional, neonatal form (21); and (vi) the predominant VGSCα (scn9a in prostate cancer cells; scn5a in breast cancer cells) was expressed more than 1000-fold more in strongly vs. weakly metastatic cells.

That we should find a similar mechanism potentially involved in metastasis of both breast and prostate cancer is not completely surprising in view of their similarities in tumour biology (e.g. hormone-responsiveness and propensity for bone metastasis) but does strongly encourage future work to investigate VGSC activity and metastasis in other cancer types. VGSCα expression has been determined in developing small cell carcinoma of the lung (42) and gliomas (43,44). Thus, functional VGSC expression may be part of a general mechanism for cancer progression and metastasis.

On the other hand, it is unclear why a specific, but different VGSCα should be associated with metastasis in breast and prostate cancers. Whilst not intending to be bound by theory, it is possible that all VGSCαs may have the capability of potentiating the metastatic cascade, or only specific types (including scn5a and scn9a). All VGSCαs that are capable of potentiating metastasis may affect the same basic cellular process(es) within the cascade, for example cellular process extension, lateral migration, secretion or transverse invasion. The specific association of a particular VGSCα with metastasis in a given cancer type may result from tissue- (or cancer-) specific transcriptional regulation/control mechanisms, for example androgens in prostate cancer or oestrogen in breast cancer. Alternatively, this specific association may result from different VGSCα(s) affecting different cellular processes which may be more or less important for successful metastasis from different primary tumour sites.

Clinical implications. Prior to the present invention, only indirect indicators as to the likelihood of metastatic potential were available, since, although it is possible to detect micrometastases in a proportion of patients with breast cancer, many patients who do not have micrometastases at presentation eventually develop overt metastatic disease during follow-up (45). Consequently, clinicians, therefore, require a more accurate method for predicting the likelihood of development of metastatic disease, and the presence of VGSCs could act as an independent prognostic parameter in a multivariant approach to this problem. Of perhaps greater significance in the future is the potential implications of inhibiting VGSC activity. The scn5a VGSCα is already the specific target of numerous anti-arrhythmic and anti-convulsant drugs, since dysfunction of scn5a in cardiac tissue is intricately linked to several forms of heart disease and arrhythmia (46). Interestingly, the breast cancer drug tamoxifen has been found also to protect the heart (47) although it is not known if this involves VGSC modulation (48). The present work, which identifies scn5a as the potential 'culprit' VGSCα in breast cancer metastasis, therefore, indicates that scn5a-specific drugs may be inhibitors of the metastatic cascade.

Sequence information The question of whether there is any difference in the sequences of the 'wild type' and the 'breast cancer culprit' SCN5A gene is an important one. In general, there are two major reasons that suggest that differences in sequence are less important than differences in level of expression: (a) The sequence data that we have obtained so far shows identity (note however that our data represent at the most only some 17% and often less than 10% of the whole sequence) and (b) the expression levels are >1000-fold different between the strongly vs the weakly metastatic cells. Taken together, we think that it is the level of expression (and whatever is responsible for it) rather than sequence difference(s) that is important. Of course, there may be some sequence differences that are important for cancer. To test that would require complete sequencing of the gene which is not a trivial exercise. There are examples of quite subtle nucleotide changes in VGSC genes giving rise to profound changes in function, leading to a pathological condition [see J. Physiol. (2000) 529:533-539, for a recent example].

REFERENCES

1. Parkin, D. M., Pisani, P. and Ferlay, J. Estimates of the worldwide incidence of 25 major cancers in 1990. Int. J. Cancer, 80: 827-841, 1999.
2. Schwirzke, M., Schiemann, S., Gnirke, A. and Weidle, U. New genes potentially involved in breast cancer metastasis. Anticancer Res., 19: 1801-1814, 1999.

3. Wingo, P. A., Ries, L. A., Rosenberg, H. M., Miller, D. S. and Edwards, B. K. Cancer incidence and mortality, 1973-1995—A report card for the US. Cancer, 82: 1197-1207, 1998.
4. Cuzick, J., Holland, R., Barth, V., Davies, R., Faupel, M., Fentiman, I., Frischbier, H. J., LaMarque, J. L., Merson, M., Sacchini, V., Vanel, D. and Veronesi, U. Electropotential measurements as a new diagnostic modality for breast cancer. The Lancet, 352: 359-363, 1998.
5. Grimes, J. A., Fraser, S. P., Stephens, G. J., Downing, J. E. G., Laniado, M. E., Foster, C. S., Abel, P. D. and Djamgoz, M. B. A. Differential expression of voltage-gated $Na^+$ currents in two prostatic tumour cell lines: contribution to invasiveness in vitro FEBS Letts., 369: 290-294, 1995.
6. Laniado, M., Lalani, E. N., Fraser, S. P., Grimes, J. A., Bhangal, G., Djamgoz, M. B. A. and Abel, P. D. Expression and functional analysis of voltage-activated $Na^+$ channels in human prostate cancer cell lines and their contribution to invasiveness in vitro. Am. J. Pathol., 150: 1213-1221, 1997.
7. Fraser, S. P., Ding, Y., Liu, A., Foster, C. S. and Djamgoz, M. B. A. Tetrodotoxin suppresses morphological enhancement of the metastatic MAT-LyLu rat prostate cancer cell line. Cell Tissue Res., 295: 505-512, 1999.
8. Fraser, S. P., Salvador, V. and Djamgoz, M. B. A. Voltage-gated $Na^+$ channel activity contributes to rodent prostate cancer migration in vitro. J. Physiol., 513P: 131P, 1998.
9. Smith, P., Rhodes, N. P., Shortland, A. P., Fraser, S. P., Djamgoz, M. B. A., Ke, Y. and Foster, C. S. Sodium channel protein expression enhances the invasiveness of rat and human prostate cancer cells. FEBS Letts., 423: 19-24, 1998.
10. Mycielska, M., Fraser, S. P., Szatkowski, M. and Djamgoz, M. B. A. Endocytic membrane activity in rat prostate cancer cell lines: potentiation by functional voltage-gated sodium channels. J. Physiol., (In the press).
11. Rodriguez, C., Calle, E. E., Tatham, L. M., Wingo, P. A., Miracle-McMahill, H. L., Thun, M. J. and Heath, C. W. Family history of breast cancer as a predictor for fatal prostate cancer. Epidemiology, 9: 525-529, 1998.
12. Catterall, W. A. From ionic currents to molecular mechanisms: the structure and function of voltage-gated sodium channels. Neuron, 26: 13-25, 2000.
13. Goldin, A. L., Snutch, T., Lubbert, H., Dowsett, A., Marshall, J., Auld, V., Downey, W., Fritz, L. C., Lester, H. A., Dunn, R., Catterall, W. A. and Davidson, N. Messenger-RNA coding for only the alpha-subunit of the rat-brain Na-channel is sufficient for expression of functional channels in Xenopus-oocytes. Proc. Natl. Acad. Sci. USA, 83: 7503-7507, 1986.
14. Isom, L. L., De Jongh, K. S., Patton, D. E., Reber, B. F. X., Offord, J., Charbonneau, H., Walsh, K., Goldin, A. L. and Catterall, W. A. Primary structure and functional expression of the beta-1-subunit of the rat-brain sodium-channel. Science, 256: 839-842, 1992.
15. Morgan, K., Stevens, E. B., Shah, B., Cox, P. J., Dixon, A. K., Lee, K., Pinnock, R. D., Hughes, J., Richardson, P. J., Mizuguchi, K. and Jackson, A. P. 3: An additional auxiliary subunit of the voltage-sensitive sodium channel that modulates channel gating with distinct kinetics. Proc. Natl. Acad. Sci. USA., 97: 2308-2313, 2000.
16. Plummer, N. W. and Meisler, M. H. Exon organization, coding sequence, physical mapping, and polymorphic intragenic markers for the human neuronal sodium channel gene SCN8A. Genomics, 57: 323-331, 1998.
17. Jeong, S. Y., Goto, J., Hashida, H., Suzuki, T., Ogata, K., Masuda, N., Hirai, M., Isahara, K., Uchiyama, Y. and Kanazawa, I. Identification of a novel human voltage-gated sodium channel alpha subunit gene, SCN12A. Biochem. Biophys. Res. Commun., 267: 262-270, 2000.
18. Soule, H. D., Vasguez, J., Long, A., Albert, S. and Brennan, M. A human cell line from a pleural effusion derived from a breast carcinoma. J. Natl. Cancer Inst., 51: 1409-1416, 1973.
19. Zhang, R. D., Fidler, I. J. and Price, J. E. Relative malignant potential of human breast-carcinoma cell-lines established from pleural effusions and a brain metastasis. Invasion Metastasis, 11: 204-215, 1991.
20. Chomczynski, P. and Sacchi, N. Single-step method of RNA isolation by acid guanidinium thiocyanate-phenol-chloroform extraction. Ann. Biochem., 162: 156-159, 1987.
21. Diss, J. K. J., Archer, S. N., Hirano, J., Fraser, S. P. and Djamgoz, M. B. A. Predominant expression of the SCN9A voltage-gated $Na^+$ channel a-subunit gene in strongly metastatic cell lines of both rat and human prostate cancer: Semi-quantitative PCR analyses. Prostate (In press).
22. Altschul, S. F., Madden, T. L., Schaffer, A. A., Zhang, J., Zhang, Z., Miller, W. and Lipman, D. J. Gapped BLAST and PSI-BLAST: a new generation of protein database search programs. Nucleic Acids Res., 25: 3389-3402, 1997.
23. Fitzsimmons, S. A., Workman, P., Grever, M., Paull, K., Camalier, R. and Lewis, A. D. Reductase enzyme expression across the National Cancer Institute Tumor cell line panel: correlation with sensitivity to mitomycin C and EO9. J. Natl. Cancer Inst., 88: 259-269, 1996.
24. Marin, A., Lopez de Cerain, A., Hamilton, E., Lewis, A. D., Martinez-Penuela, J. M., Idoate, M. A. and Bello, J. DT-diaphorase and cytochrome B5 reductase in human lung and breast tumours. Br. J. Cancer, 76: 923-929, 1997.
25. Gu, X. Q., Dib-Hajj, S. D., Rizzo, M. and Waxman, S. G. TTX-sensitive and -resistant $Na^+$ currents, and mRNA for the TTX-resistant rH1 channel, are expressed in B104 neuroblastoma cells. J. Neurophysiol., 77: 236-246, 1997.
26. Donahue, L. M., Schaller, K. and Sueoka, N. Segregation of $Na^+$-channel gene-expression during neuronal glial branching of a rat PNS-derived stem-cell line, RT4-AC. Devel. Biol., 147: 415-424, 1991.
27. Zeng, D. W., Kyle, J. W., Martin, R. L., Ambler, K. S. and Hanck, D. A. Cardiac sodium channels expressed in a peripheral neurotumor-derived cell line, RT4-B8. Am. J. Physiol., 39: C1522-C1531, 1996.
28. Gellens, M. E., George, A. L., Chen, L. Q., Chahine, M., Horn, R., Barchi, R. C. and Kallen, R. G. Primary structure and functional expression of the human cardiac tetrodotoxin-insensitive voltage-dependent sodium-channel. Proc. Natl. Acad. Sci. USA., 89: 554-558, 1992.
29. Rogart, R. B., Cribbs, L. L., Muglia, L. K., Kephart, D. D. and Kaiser, M. W. Molecular-cloning of a putative tetrodotoxin-resistant rat-heart $Na^+$ channel isoform. Proc. Natl. Acad. Sci. USA., 86: 8170-8174, 1989.
30. Cohen, S. A. and Levitt, L. K. Partial characterization of the rH1 sodium-channel protein from rat-heart using subtype-specific antibodies. Circulation Res., 73: 735-742, 1993.
31. Santana, L. F., Gomez, A. M. and Lederer, W. J. $Ca^{2+}$ flux through promiscuous cardiac $Na^+$ channels: Slip-mode conductance. Science, 279: 1027-1033, 1998.
32. White, M. M., Chen, L. Q., Kleinfield, R., Kallen, R. G. and Barchi, R. L. Skm2, a $Na^+$ channel cDNA clone from denervated skeletal-muscle, encodes a tetrodotoxin-insensitive $Na^+$ channel. Mol. Pharmacol., 39: 604-608, 1991.

33. Rich, M. M., Kraner, S. D. and Barchi, R. L. Altered gene expression in steroid-treated denervated muscle. Neurobiol. Dis., 6: 515-522, 1999.
34. Kallen R. G., Sheng Z. H., Yang J., Chen L. Q., Rogart R. B. and Barchi R. L. Primary structure and expression of a sodium-channel characteristic of denervated and immature rat skeletal-muscle. Neuron 4: 233-242, 1990.
35. Black, J. A., Dib-Hajj, S. D., Cohen, S., Hinson, A. W. and Waxman, S. G. Glial cells have heart: rH1 Na+ channel mRNA and protein in spinal cord astrocytes. Glia 23: 200-208, 1998.
36. Black, J. A., Dib-Hajj, S. D., McNabola, K., Jeste, S., Rizzo, M. A., Kocsis, J. D. and Waxman, S. G. Spinal sensory neurons express multiple sodium channel alpha-subunit mRNAs. Mol. Brain Res., 43: 117-131, 1996.
37. Dib-Hajj, S. D., Tyrell, L., Black, J. A. and Waxman, S. G. NaN, a novel voltage-gated Na channel, is expressed preferentially in peripheral sensory neurons and down-regulated after axotomy. Proc. Natl. Acad. Sci. USA., 95: 8963-8968, 1998.
38. Yang, J. S. J., Sladky, J. T., Kallen, R. G. and Barchi, R. L. TTX-sensitive and TTX-insensitive sodium-channel messenger-RNA transcripts are independently regulated in adult skeletal-muscle after denervation. Neuron, 7: 421-427, 1991.
39. Fidler, I. J. Tumor heterogeneity and the biology of cancer invasion and metastasis. Cancer Res., 38: 2651-2660, 1978.
40. Fidler, I. J. and Hart, I. R. Biological diversity in metastatic neoplasms: origins ands implications. Science, 217: 998-1003, 1982.
41. Plummer, N. W., McBurney, M. W. and Meisler, M. H. Alternative splicing of the sodium channel SCN8A predicts a truncated two-domain protein in fetal brain and non-neuronal cells. J. Biol. Chem., 272: 24008-24015, 1997.
42. Blandino, J. K. W., Viglione, M. P., Bradley, W. A., Oie, H. K., Kim, Y. I. Voltage-dependent sodium-channels in human small-cell lung-cancer cells—Role in action-potentials and inhibition by Lambert-Eaton syndrome IgG. J. Membr. Biol., 143: 153-163, 1995.
43. Patt, S., Wlasak, R. and Kraft, R. Influence of voltage-activated sodium channels on growth and motility of human neuroblastoma cells in vitro. Brain Pathol., 10: 738, 2000.
44. Patt, S., Labrakakis, C., Bernstein, M., Weydt, P., Cervos-Navarro, J., Nisch, G., Kettenmann, H. Neuron-like physiological properties of cells from human oligodendroglial tumors. Neurosci., 71: 601-611, 1996.
45. Mansi, J. L., Gogas, H., Bliss, J. M., Gazet, J. C., Berger, U. and Coombes, R. C. Outcome of primary-breast-cancer patients with micrometastases: a long-term follow-up study. The Lancet, 354: 197-202, 1999.
46. Jongsma, H. J. Sudden cardiac death: A matter of faulty ion channels? Curr. Biol., 8: R568-R571, 1998.
47. Hardy, S. P., deFelipe, C., Valverde, M. A. Inhibition of voltage-gated cationic channels in rat embryonic hypothalamic neurones and C1300 neuroblastoma cells by triphenylethylene antooestrogens. FEBS Lett 434: 236-240, 1998.
48. Cushman, M., Costantino, J. P., Tracy, R. P., Song, K., Buckley, L., Roberts, J. D., D. N. Tamoxifen and cardiac risk factors in healthy women: suggestion of an anti-inflammatory effect. Thromb Vasc Biol 21: 255-261, 2001.

EXAMPLE 2

Design of Antisense Oligonucleotides for Suppressing VGSC Expression in Human Prostate Cancer 1. Alignment of all currently known VGSC types to identify potential sites for VGSC Subtype-specific antisense oligonucleotide design.

```
Cons           agtgagtgtgaaagtcttatggagagcaacaaaactg---tccgatggaaa
               (SEQ ID NO 47)

hNav2.1        agtcggtgtgaaagccttctgt---ttaacgaatcca---tgctatgggaa
               (SEQ ID NO 48)

hNe-Na         tccgaatgttttgcccttatgaATGTTAGTCAAAATG---TGCGAtggaaa
               (SEQ ID NO 49)

Human brain 1  actgattgcctaaaactaatagaaagaaatgagactg---ctcgatggaaa
               (SEQ ID NO 50)

Human brain 2  agtgagtgcaAAGCTCTCATTGAGAGCAATcaaactg---ccaggtggaaa
               (SEQ ID NO 51)

Human brain 3  agtgactgtc--aggctcttggcaagcaa-------g---ctcggtggaaa
               (SEQ ID NO 52)

Na6 (human)    actgaatgtgaaaagcttatggaggggAACAATACAGAGATCAGATGgaag
               (SEQ ID NO 53)

hSkM1          aacaagtctgagtgcgagagCCTCATGCACACAGGCCAGGtccgctggctc
               (SEQ ID NO 54)

Human heart 1  aacaagagccagtgtgagtccttgaacttgaccggagaattgtactggacc
               (SEQ ID NO 55)

PN3/SNS (rat)  aacaagtccgagtgtcacaatcaaaacagcaccggccacttcttctgggtc
               (SEQ ID NO 56)
```

HNeNa is derived from SCN9A and Na6 from SCN8A.
In the above alignment the human VGSC equivalent has been used where possible. The alignment has been optimised by the introduction of sequence gaps indicated by a dash although gaps are not actually present in the real sequence or any oligonucleotide design. The most commonly occurring nucleotides are indicated in the consensus line (Cons). Potential sites for the design of 20mer antisense oligonucleotides are in bold case and underlined in four human VGSC types. The most unconserved region of the fragment produced by the degenerate screen has been used to produce this line-up.

It would also be possible to design 20mer antisense oligos in the ¾ cytoplasmic linker (where VGSC sequence is highly conserved across all types) that are individually capable of 'silencing' simultaneously a number of VGSC types. For example, below the same 20 nucleotide sections of the ¾ linker from three VGSC types are shown aligned. In this section, the hNe-Na and the human brain 2 sequences are identical and the hSkMl sequence differs at only two nucleotide positions. Therefore, in this region it is possible to design two antisense oligonucleotides that will knock-out at least three of the channels (possibly four when the Na6 (human) sequence has been confirmed for this region).

```
hNe-Na          TTATGACAGAAGAACAGAAG
                (SEQ ID NO 57)

Human brain 2   TTATGACAGAAGAACAGAAG
                (SEQ ID NO 58)

hSkM1           TTATGACgGAgGAACAGAAG
                (SEQ ID NO 59)
```

The invention claimed is:

1. A method of determining the susceptibility of a human breast cancer patient to, metastasis or diagnosis of breast cancer in a human patient at risk of or suspected of having breast cancer comprising the steps of:
(a) obtaining a tissue sample containing nucleic acid and/or protein from the patient; and
(b) determining whether the sample contains voltage gated $Na^+$ channel SCN5A nucleic acid and/or protein, wherein the presence of an elevated amount of voltage-gated $Na^+$ channel SCN5A nucleic acid and/or protein relative to non-cancerous or non-metastatic breast cells is indicative of the susceptibility of a human breast cancer patient to metastasis or diagnosis of breast cancer in a human patient.

2. A method according to claim 1 wherein the cancer is metastatic.

3. A method according to either of claims 1 or 2 wherein the sample contains nucleic acid and the level of said voltage gated $Na^+$ channel SCN5a nucleic acid is measured by contacting the said nucleic acid with a nucleic acid which hybridizes selectively to said voltage-gated $Na^+$ channel SCN5a nucleic acid.

4. A method according to claim 3 wherein the nucleic acid which hybridizes as said is detectably labeled.

5. A method according to claim 3 wherein the nucleic acid which selectively hybridizes as said is suitable for use in a nucleic acid amplification reaction.

6. A method according to either of claims 1 or 2 wherein the sample contains protein and the level of said voltage gated $Na^+$ channel SCN5a protein is measured.

7. A method according to claim 6 wherein the level of said protein is measured by contacting the protein with an antibody or antigen binding antibody fragment which selectively binds to the said voltage-gated $Na^+$ channel SCN5a protein.

8. A method according to claim 7 wherein the antibody or antigen-binding antibody fragment comprises a detectable label.

9. A method according to claim 1 wherein the sample is a breast tissue sample selected from the group consisting of tissue in which cancer is suspected, tissue in which cancer may be found, tissue in which cancer has been found or one which contains cells from said tissue.

* * * * *

SEQUENCE LISTING

```
<160> NUMBER OF SEQ ID NOS: 59

<210> SEQ ID NO 1
<211> LENGTH: 6371
<212> TYPE: DNA
<213> ORGANISM: Homo sapiens

<400> SEQUENCE: 1
ctcttatgtg aggagctgaa gaggaattaa aatatacagg atgaaaagat ggcaatgttg      60
cctcccccag gacctcagag ctttgtccat ttcacaaaac agtctcttgc cctcattgaa     120
caacgcattg ctgaaagaaa atcaaaggaa cccaaagaag aaaagaaaga tgatgatgaa     180
gaagccccaa agccaagcag tgacttggaa gctggcaaac aactgcccct catctatggg     240
gacattcctc ccggcatggt gtcagagccc tggaggact tggaccccta ctatgcagac     300
aaaaagactt tcatagtatt gaacaaaggg aaaacaatct tccgtttcaa tgccacacct     360
gctttatata tgctttctcc tttcagtcct ctaagaagaa tatctattaa gatttttagta    420 cactccttat tcagcatgct catcatgtgc actattctga caaactgcat atttatgacc     480
atgaataacc cgccggactg gaccaaaaat gtcgagtaca cttttactgg aatatatact     540
tttgaatcac ttgtaaaaat ccttgcaaga ggcttctgtg taggagaatt cactttttctt    600 cgtgacccgt ggaactggct ggattttgtc gtcattgttt ttgcgtattt aacagaattt     660
gtaaacctag gcaatgtttc agctcttcga actttcagag tattgagagc tttgaaaact     720
atttctgtaa tcccaggcct gaagacaatt gtagggcttt gatccagtc agtgaagaag      780 ctttctgatg tcatgatcct gactgtgttc tgtctgagtg tgtttgcact aattggacta     840
cagctgttca tgggaaacct gaagcataaa tgttttcgaa attcacttga aaataatgaa     900
acattagaaa gcataatgaa taccctagag agtgaagaag acttagaaa atattttat      960 tacttggaag gatccaaaga tgctctcctt tgtggtttca gcacagattc aggtcagtgt    1020 ccagagggggt acacctgtgt gaaaattggc agaaaccctg attatggcta cacgagcttt    1080
gacactttca gctgggcctt cttagccttg tttaggctaa tgacccaaga ttactgggaa    1140
aacctttacc aacagacgct gcgtgctgct ggcaaaacct acatgatctt ctttgtcgta    1200 gtgatttcc tgggctcctt ttatctaata aacttgatcc tggctgtggt tgccatggca    1260
tatgaagaac agaaccaggc aaacattgaa gaagctaaac agaaagaatt agaatttcaa    1320
cagatgttag accgtcttaa aaagagcaa gaagaagctg aggcaattgc agcggcagcg    1380
gctgaatata caagtattag gagaagcaga attatgggcc tctcagagag ttcttctgaa    1440
```

```
acatccaaac tgagctctaa aagtgctaaa gaaagaagaa acagaagaaa gaaaaagaat    1500
caaaagaagc tctccagtgg agaggaaaag ggagatgctg agaaattgtc gaaatcagaa    1560
tcagaggaca gcatcagaag aaaaagtttc caccttggtg tcgaagggca taggcgagca    1620
catgaaaaga ggttgtctac ccccaatcag tcaccactca gcattcgtgg ctccttgttt    1680
tctgcaaggc gaagcagcag aacaagtctt tttagtttca aaggcagagg aagagatata    1740
ggatctgaga ctgaatttgc cgatgatgag cacagcattt ttggagacaa tgagagcaga    1800
aggggctcac tgtttgtgcc ccacagaccc caggagcgac gcagcagtaa catcagccaa    1860
gccagtaggt ccccaccaat gctgccggtg aacgggaaaa tgcacagtgc tgtggactgc    1920
aacggtgtgg tctccctggt tgatggacgc tcagccctca tgctcccaa tggacagctt    1980 ctgccagagg gcacgaccaa tcaaatacac aagaaaaggc gttgtagttc ctatctcctt    2040
tcagaggata tgctgaatga tcccaacctc agacagagag caatgagtag agcaagcata    2100
ttaacaaaca ctgtggaaga acttgaagag tccagacaaa aatgtccacc ttggtggtac    2160
agatttgcac acaaattctt gatctggaat tgctctccat attggataaa attcaaaaag    2220
tgtatctatt ttattgtaat ggatcctttt gtagatcttg caattaccat ttgcatagtt    2280
ttaaacacat tatttatggc tatggaacac cacccaatga ctgaggaatt caaaaatgta    2340
cttgctatag gaaatttggt cttactgga atctttgcag ctgaaatggt attaaaactg    2400
attgccatgg atccatatga gtatttccaa gtaggctgga atattttga cagccttatt    2460 gtgactttaa gtttagtgga gctctttcta gcagatgtgg aaggattgtc agttctgcga    2520
tcattcagac tgctccgagt cttcaagttg gcaaaatcct ggccaacatt gaacatgctg    2580
attaagatca ttggtaactc agtaggggct ctaggtaacc tcaccttagt gttggccatc    2640
atcgtcttca tttttgctgt ggtcggcatg cagctctttg gtaagagcta caaagaatgt    2700
gtctgcaaga tcaatgatga ctgtacgctc ccacggtggc acatgaacga cttcttccac    2760
tccttcctga ttgtgttccg cgtgctgtgt ggagagtgga tagagaccat gtgggactgt    2820
atggaggtcg ctggtcaagc tatgtgcctt attgtttaca tgatggtcat ggtcattgga    2880
aacctggtgg tcctaaacct atttctggcc ttattattga gctcatttag ttcagacaat    2940
cttacagcaa ttgaagaaga ccctgatgca acaacctcc agattgcagt gactagaatt    3000
aaaaagggaa taaattatgt gaaacaaacc ttacgtgaat ttattctaaa agcattttcc    3060
aaaaagccaa agatttccag ggagataaga caagcagaag atctgaatac taagaaggaa    3120 aactatatttt ctaaccatac acttgctgaa atgagcaaag gtcacaattt cctcaaggaa    3180
aaagataaaa tcagtggttt tggaagcagc gtggacaaac acttgatgga agacagtgat    3240
ggtcaatcat ttattcacaa tcccagcctc acagtgacag tgccaattgc acctggggaa    3300
tccgatttgg aaaatatgaa tgctgaggaa cttagcagtg attcggatag tgaatacagc    3360
aaagtgagat taaaccggtc aagctcctca gagtgcagca cagttgataa cccttttgcct    3420 ggagaaggag aagaagcaga ggctgaacct atgaattccg atgagccaga ggcctgtttc    3480
acagatggtt gtgtacggag gttctcatgc tgccaagtta acatagagtc agggaaagga    3540
aaaatctggt ggaacatcag gaaaacctgc tacaagattt tgaacacag ttggtttgaa    3600 agcttcattg tcctcatgat cctgctcagc agtggtgccc tggcttttga agatatttat    3660
attgaaagga aaaagaccat taagattatc ctggagtatg cagacaagat cttcacttac    3720
atcttcattc tggaaatgct tctaaaatgg atagcatatg gttataaaac atatttcacc    3780
```

```
aatgcctggt gttggctgga tttcctaatt gttgatgttt ctttggttac tttagtggca   3840
aacactcttg gctactcaga tcttggcccc attaaatccc ttcggacact gagagcttta   3900
agacctctaa gagccttatc tagatttgaa ggaatgaggg tcgttgtgaa tgcactcata   3960
ggagcaattc cttccatcat gaatgtgcta cttgtgtgtc ttatattctg gctgatattc   4020
agcatcatgg gagtaaattt gtttgctggc aagttctatg agtgtattaa caccacagat   4080
gggtcacggt ttcctgcaag tcaagttcca atcgttccg aatgttttgc ccttatgaat   4140
gttagtcaaa atgtgcgatg gaaaaacctg aaagtgaact ttgataatgt cggacttggt   4200
tacctatctc tgcttcaagt tgcaactttt aagggatgga cgattattat gtatgcagca   4260
gtggattctg ttaatgtaga caagcagccc aaatatgaat atagcctcta catgtatatt   4320
tattttgtcg tctttatcat ctttgggtca ttcttcactt tgaacttgtt cattggtgtc   4380
atcatagata atttcaacca acagaaaaag aagcttggag gtcaagacat ctttatgaca   4440
gaagaacaga gaaatacta taatgcaatg aaaaagctgg ggtccaagaa gccacaaaag   4500
ccaattcctc gaccagggaa caaaatccaa ggatgtatat ttgacctagt gacaaatcaa   4560
gcctttgata ttagtatcat ggttcttatc tgtctcaaca tggtaaccat gatggtagaa   4620
aaggagggtc aaagtcaaca tatgactgaa gttttatatt ggataaatgt ggtttttata   4680 atcctttca ctggagaatg tgtgctaaaa ctgatctccc tcagacacta ctacttcact   4740
gtaggatgga atatttttga ttttgtggtt gtgattatct ccattgtagg tatgtttcta   4800
gctgatttga ttgaaacgta ttttgtgtcc cctaccctgt tccgagtgat ccgtcttgcc   4860
aggattggcc gaatcctacg tctagtcaaa ggagcaaagg ggatccgcac gctgctcttt   4920
gctttgatga tgtcccttcc tgcgttgttt aacatcggcc tcctgctctt cctggtcatg   4980
ttcatctacg ccatctttgg aatgtccaac tttgcctatg ttaaaaagga agatggaatt   5040
aatgacatgt tcaattttga gacctttggc aacagtatga tttgcctgtt ccaaattaca   5100
acctctgctg gctgggatgg attgctagca cctattctta acagtaagcc acccgactgt   5160
gacccaaaaa aagttcatcc tggaagttca gttgaaggag actgtggtaa cccatctgtt   5220
ggaatattct actttgttag ttatatcatc atatccttcc tggttgtggt gaacatgtac   5280
attgcagtca tactgagaaa ttttagtgtt gccactgaag aaagtactga acctctgagt   5340
gaggatgact ttgagatgtt ctatgaggtt tgggagaagt ttgatcccga tgcgacccag   5400
tttatagagt tctctaaact ctctgatttt gcagctgccc tggatcctcc tcttctcata   5460 gcaaaccca acaaagtcca gctcattgcc atggatctgc ccatggttag tggtgaccgg   5520
atccattgtc ttgacatctt atttgctttt acaaagcgtg ttttgggtga gagtggggag   5580
atggattctc ttcgttcaca gatggaagaa aggttcatgt ctgcaaatcc ttccaaagtg   5640
tcctatgaac ccatcacaac cacactaaaa cggaaacaag aggatgtgtc tgctactgtc   5700
attcagcgtg cttatagacg ttaccgctta aggcaaaatg tcaaaaatat atcaagtata   5760
tacataaaag atggagacag agatgatgat ttactcaata aaaaagatat ggcttttgat   5820
aatgttaatg agaactcaag tccagaaaaa acagatgcca cttcatccac cacctctcca   5880
ccttcatatg atagtgtaac aaagccagac aaagagaaat atgaacaaga cagaacagaa   5940
aaggaagaca aagggaaaga cagcaaggaa agcaaaaaat agagcttcat ttttgatata   6000
ttgtttacag cctgtgaaag tgatttattt gtgttaataa aactcttttg aggaagtcta   6060
tgccaaaatc ctttttatca aaatattctc gaaggcagtg cagtcactaa ctctgatttc   6120
ctaagaaagg tgggcagcat tagcagatgg ttattttgc actgatgatt ctttaagaat   6180
```

```
cgtaagagaa ctctgtagga attattgatt atagcataca aaagtgattg attcagtttt      6240
ttggttttta ataaatcaga agaccatgta gaaaactttt acatctgcct tgtcatcttt      6300
tcacaggatt gtaattagtc ttgtttccca tgtaaataaa caacacacgc atacagaaaa      6360
aaaaaaaaaa a                                                          6371
```

<210> SEQ ID NO 2
<211> LENGTH: 1977
<212> TYPE: PRT
<213> ORGANISM: Homo sapiens

<400> SEQUENCE: 2

```
Met Ala Met Leu Pro Pro Gly Pro Gln Ser Phe Val His Phe Thr
1               5                   10                  15

Lys Gln Ser Leu Ala Leu Ile Glu Gln Arg Ile Ala Glu Arg Lys Ser
            20                  25                  30

Lys Glu Pro Lys Glu Glu Lys Lys Asp Asp Asp Glu Ala Pro Lys
        35                  40                  45

Pro Ser Ser Asp Leu Glu Ala Gly Lys Gln Leu Pro Phe Ile Tyr Gly
50                  55                  60

Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335
```

```
Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
            355                 360                 365

Gln Thr Leu Arg Ala Ala Gly Lys Thr Tyr Met Ile Phe Phe Val Val
            370                 375             380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
                420                 425                 430

Glu Gln Glu Glu Ala Glu Ala Ile Ala Ala Ala Ala Ala Glu Tyr Thr
            435                 440                 445

Ser Ile Arg Arg Ser Arg Ile Met Gly Leu Ser Glu Ser Ser Ser Glu
            450                 455                 460

Thr Ser Lys Leu Ser Ser Lys Ser Ala Lys Glu Arg Arg Asn Arg Arg
465                 470                 475                 480

Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
            515                 520                 525

Leu Ser Thr Pro Asn Gln Ser Pro Leu Ser Ile Arg Gly Ser Leu Phe
            530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
            595                 600                 605

Pro Pro Met Leu Pro Val Asn Gly Lys Met His Ser Ala Val Asp Cys
            610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
            675                 680                 685

Val Glu Glu Leu Glu Glu Ser Arg Gln Lys Cys Pro Pro Trp Trp Tyr
            690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750
```

-continued

```
Glu His His Pro Met Thr Glu Phe Lys Asn Val Leu Ala Ile Gly
        755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
        835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu Lys Ala Phe Ser Lys Lys Pro Lys
        995                 1000                1005

Ile Ser Arg Glu Ile Arg Gln Ala Glu Asp Leu Asn Thr Lys Lys
    1010                1015                1020

Glu Asn Tyr Ile Ser Asn His Thr Leu Ala Glu Met Ser Lys Gly
    1025                1030                1035

His Asn Phe Leu Lys Glu Lys Asp Lys Ile Ser Gly Phe Gly Ser
    1040                1045                1050

Ser Val Asp Lys His Leu Met Glu Asp Ser Asp Gly Gln Ser Phe
    1055                1060                1065

Ile His Asn Pro Ser Leu Thr Val Thr Val Pro Ile Ala Pro Gly
    1070                1075                1080

Glu Ser Asp Leu Glu Asn Met Asn Ala Glu Glu Leu Ser Ser Asp
    1085                1090                1095

Ser Asp Ser Glu Tyr Ser Lys Val Arg Leu Asn Arg Ser Ser Ser
    1100                1105                1110

Ser Glu Cys Ser Thr Val Asp Asn Pro Leu Pro Gly Glu Gly Glu
    1115                1120                1125

Glu Ala Glu Ala Glu Pro Met Asn Ser Asp Glu Pro Glu Ala Cys
    1130                1135                1140

Phe Thr Asp Gly Cys Val Arg Phe Ser Cys Cys Gln Val Asn
    1145                1150                1155

Ile Glu Ser Gly Lys Gly Lys Ile Trp Trp Asn Ile Arg Lys Thr
```

```
                1160                1165                1170
Cys Tyr Lys Ile Val Glu His Ser Trp Phe Glu Ser Phe Ile Val
    1175                1180                1185

Leu Met Ile Leu Leu Ser Ser Gly Ala Leu Ala Phe Glu Asp Ile
    1190                1195                1200

Tyr Ile Glu Arg Lys Lys Thr Ile Lys Ile Ile Leu Glu Tyr Ala
    1205                1210                1215

Asp Lys Ile Phe Thr Tyr Ile Phe Ile Leu Glu Met Leu Leu Lys
    1220                1225                1230

Trp Ile Ala Tyr Gly Tyr Lys Thr Tyr Phe Thr Asn Ala Trp Cys
    1235                1240                1245

Trp Leu Asp Phe Leu Ile Val Asp Val Ser Leu Val Thr Leu Val
    1250                1255                1260

Ala Asn Thr Leu Gly Tyr Ser Asp Leu Gly Pro Ile Lys Ser Leu
    1265                1270                1275

Arg Thr Leu Arg Ala Leu Arg Pro Leu Arg Ala Leu Ser Arg Phe
    1280                1285                1290

Glu Gly Met Arg Val Val Asn Ala Leu Ile Gly Ala Ile Pro
    1295                1300                1305

Ser Ile Met Asn Val Leu Leu Val Cys Leu Ile Phe Trp Leu Ile
    1310                1315                1320

Phe Ser Ile Met Gly Val Asn Leu Phe Ala Gly Lys Phe Tyr Glu
    1325                1330                1335

Cys Ile Asn Thr Thr Asp Gly Ser Arg Phe Pro Ala Ser Gln Val
    1340                1345                1350

Pro Asn Arg Ser Glu Cys Phe Ala Leu Met Asn Val Ser Gln Asn
    1355                1360                1365

Val Arg Trp Lys Asn Leu Lys Val Asn Phe Asp Asn Val Gly Leu
    1370                1375                1380

Gly Tyr Leu Ser Leu Leu Gln Val Ala Thr Phe Lys Gly Trp Thr
    1385                1390                1395

Ile Ile Met Tyr Ala Ala Val Asp Ser Val Asn Val Asp Lys Gln
    1400                1405                1410

Pro Lys Tyr Glu Tyr Ser Leu Tyr Met Tyr Ile Tyr Phe Val Val
    1415                1420                1425

Phe Ile Ile Phe Gly Ser Phe Phe Thr Leu Asn Leu Phe Ile Gly
    1430                1435                1440

Val Ile Ile Asp Asn Phe Asn Gln Gln Lys Lys Lys Leu Gly Gly
    1445                1450                1455

Gln Asp Ile Phe Met Thr Glu Glu Gln Lys Lys Tyr Tyr Asn Ala
    1460                1465                1470

Met Lys Lys Leu Gly Ser Lys Lys Pro Gln Lys Pro Ile Pro Arg
    1475                1480                1485

Pro Gly Asn Lys Ile Gln Gly Cys Ile Phe Asp Leu Val Thr Asn
    1490                1495                1500

Gln Ala Phe Asp Ile Ser Ile Met Val Leu Ile Cys Leu Asn Met
    1505                1510                1515

Val Thr Met Met Val Glu Lys Glu Gly Gln Ser Gln His Met Thr
    1520                1525                1530

Glu Val Leu Tyr Trp Ile Asn Val Val Phe Ile Ile Leu Phe Thr
    1535                1540                1545

Gly Glu Cys Val Leu Lys Leu Ile Ser Leu Arg His Tyr Tyr Phe
    1550                1555                1560
```

-continued

```
Thr Val Gly Trp Asn Ile Phe Asp Phe Val Val Ile Ile Ser
    1565                1570                1575

Ile Val Gly Met Phe Leu Ala Asp Leu Ile Glu Thr Tyr Phe Val
    1580                1585                1590

Ser Pro Thr Leu Phe Arg Val Ile Arg Leu Ala Arg Ile Gly Arg
    1595                1600                1605

Ile Leu Arg Leu Val Lys Gly Ala Lys Gly Ile Arg Thr Leu Leu
    1610                1615                1620

Phe Ala Leu Met Met Ser Leu Pro Ala Leu Phe Asn Ile Gly Leu
    1625                1630                1635

Leu Leu Phe Leu Val Met Phe Ile Tyr Ala Ile Phe Gly Met Ser
    1640                1645                1650

Asn Phe Ala Tyr Val Lys Lys Glu Asp Gly Ile Asn Asp Met Phe
    1655                1660                1665

Asn Phe Glu Thr Phe Gly Asn Ser Met Ile Cys Leu Phe Gln Ile
    1670                1675                1680

Thr Thr Ser Ala Gly Trp Asp Gly Leu Leu Ala Pro Ile Leu Asn
    1685                1690                1695

Ser Lys Pro Pro Asp Cys Asp Pro Lys Lys Val His Pro Gly Ser
    1700                1705                1710

Ser Val Glu Gly Asp Cys Gly Asn Pro Ser Val Gly Ile Phe Tyr
    1715                1720                1725

Phe Val Ser Tyr Ile Ile Ile Ser Phe Leu Val Val Val Asn Met
    1730                1735                1740

Tyr Ile Ala Val Ile Leu Glu Asn Phe Ser Val Ala Thr Glu Glu
    1745                1750                1755

Ser Thr Glu Pro Leu Ser Glu Asp Asp Phe Glu Met Phe Tyr Glu
    1760                1765                1770

Val Trp Glu Lys Phe Asp Pro Asp Ala Thr Gln Phe Ile Glu Phe
    1775                1780                1785

Ser Lys Leu Ser Asp Phe Ala Ala Ala Leu Asp Pro Pro Leu Leu
    1790                1795                1800

Ile Ala Lys Pro Asn Lys Val Gln Leu Ile Ala Met Asp Leu Pro
    1805                1810                1815

Met Val Ser Gly Asp Arg Ile His Cys Leu Asp Ile Leu Phe Ala
    1820                1825                1830

Phe Thr Lys Arg Val Leu Gly Glu Ser Gly Glu Met Asp Ser Leu
    1835                1840                1845

Arg Ser Gln Met Glu Glu Arg Phe Met Ser Ala Asn Pro Ser Lys
    1850                1855                1860

Val Ser Tyr Glu Pro Ile Thr Thr Thr Leu Lys Arg Lys Gln Glu
    1865                1870                1875

Asp Val Ser Ala Thr Val Ile Gln Arg Ala Tyr Arg Arg Tyr Arg
    1880                1885                1890

Leu Arg Gln Asn Val Lys Asn Ile Ser Ser Ile Tyr Ile Lys Asp
    1895                1900                1905

Gly Asp Arg Asp Asp Asp Leu Leu Asn Lys Lys Asp Met Ala Phe
    1910                1915                1920

Asp Asn Val Asn Glu Asn Ser Ser Pro Glu Lys Thr Asp Ala Thr
    1925                1930                1935

Ser Ser Thr Thr Ser Pro Pro Ser Tyr Asp Ser Val Thr Lys Pro
    1940                1945                1950
```

-continued

```
Asp Lys Glu Lys Tyr Glu Gln Asp Arg Thr Glu Lys Glu Asp Lys
    1955                1960                1965

Gly Lys Asp Ser Lys Glu Ser Lys Lys
    1970                1975

<210> SEQ ID NO 3
<211> LENGTH: 8491
<212> TYPE: DNA
<213> ORGANISM: Homo sapiens
<220> FEATURE:
<221> NAME/KEY: misc_feature
<222> LOCATION: (7027)..(7027)
<223> OTHER INFORMATION: Unknown sequence
<220> FEATURE:
<221> NAME/KEY: misc_feature
<222> LOCATION: (7234)..(7234)
<223> OTHER INFORMATION: Unknown sequence
<220> FEATURE:
<221> NAME/KEY: misc_feature
<222> LOCATION: (7294)..(7294)
<223> OTHER INFORMATION: Unknown sequence
<220> FEATURE:
<221> NAME/KEY: misc_feature
<222> LOCATION: (7308)..(7308)
<223> OTHER INFORMATION: Unknown sequence
<220> FEATURE:
<221> NAME/KEY: misc_feature
<222> LOCATION: (7309)..(7309)
<223> OTHER INFORMATION: Unknown sequence
<220> FEATURE:
<221> NAME/KEY: misc_feature
<222> LOCATION: (7485)..(7485)
<223> OTHER INFORMATION: Unknown sequence
<220> FEATURE:
<221> NAME/KEY: misc_feature
<222> LOCATION: (7486)..(7486)
<223> OTHER INFORMATION: Unknown sequence
<220> FEATURE:
<221> NAME/KEY: misc_feature
<222> LOCATION: (7546)..(7546)
<223> OTHER INFORMATION: Unknown sequence
<220> FEATURE:
<221> NAME/KEY: misc_feature
<222> LOCATION: (7726)..(7726)
<223> OTHER INFORMATION: Unknown sequence
<220> FEATURE:
<221> NAME/KEY: misc_feature
<222> LOCATION: (7727)..(7727)
<223> OTHER INFORMATION: Unknown sequence
<220> FEATURE:
<221> NAME/KEY: misc_feature
<222> LOCATION: (7727)..(7727)
<223> OTHER INFORMATION: Unknown sequence
<220> FEATURE:
<221> NAME/KEY: misc_feature
<222> LOCATION: (7741)..(7741)
<223> OTHER INFORMATION: Unknown sequence
<220> FEATURE:
<221> NAME/KEY: misc_feature
<222> LOCATION: (7746)..(7746)
<223> OTHER INFORMATION: Unknown sequence
<220> FEATURE:
<221> NAME/KEY: misc_feature
<222> LOCATION: (7749)..(7749)
<223> OTHER INFORMATION: Unknown sequence
<220> FEATURE:
<221> NAME/KEY: misc_feature
<222> LOCATION: (7750)..(7750)
<223> OTHER INFORMATION: Unknown sequence
<220> FEATURE:
<221> NAME/KEY: misc_feature
<222> LOCATION: (7751)..(7751)
<223> OTHER INFORMATION: Unknown sequence
<220> FEATURE:
<221> NAME/KEY: misc_feature
<222> LOCATION: (7759)..(7759)
<223> OTHER INFORMATION: Unknown sequence
```

```
<220> FEATURE:
<221> NAME/KEY: misc_feature
<222> LOCATION: (7761)..(7761)
<223> OTHER INFORMATION: Unknown sequence
<220> FEATURE:
<221> NAME/KEY: misc_feature
<222> LOCATION: (7762)..(7762)
<223> OTHER INFORMATION: Unknown sequence
<220> FEATURE:
<221> NAME/KEY: misc_feature
<222> LOCATION: (7763)..(7763)
<223> OTHER INFORMATION: Unknown sequence
<220> FEATURE:
<221> NAME/KEY: misc_feature
<222> LOCATION: (7764)..(7764)
<223> OTHER INFORMATION: Unknown sequence
<220> FEATURE:
<221> NAME/KEY: misc_feature
<222> LOCATION: (7765)..(7765)
<223> OTHER INFORMATION: Unknown sequence
<220> FEATURE:
<221> NAME/KEY: misc_feature
<222> LOCATION: (7769)..(7769)
<223> OTHER INFORMATION: Unknown sequence
<220> FEATURE:
<221> NAME/KEY: misc_feature
<222> LOCATION: (7770)..(7770)
<223> OTHER INFORMATION: Unknown sequence
<220> FEATURE:
<221> NAME/KEY: misc_feature
<222> LOCATION: (7793)..(7793)
<223> OTHER INFORMATION: Unknown sequence
<220> FEATURE:
<221> NAME/KEY: misc_feature
<222> LOCATION: (7814)..(7814)
<223> OTHER INFORMATION: Unknown sequence
<220> FEATURE:
<221> NAME/KEY: misc_feature
<222> LOCATION: (7829)..(7829)
<223> OTHER INFORMATION: Unknown sequence
<220> FEATURE:
<221> NAME/KEY: misc_feature
<222> LOCATION: (7830)..(7830)
<223> OTHER INFORMATION: Unknown sequence
<220> FEATURE:
<221> NAME/KEY: misc_feature
<222> LOCATION: (7882)..(7882)
<223> OTHER INFORMATION: Unknown sequence
<220> FEATURE:
<221> NAME/KEY: misc_feature
<222> LOCATION: (7998)..(7998)
<223> OTHER INFORMATION: Unknown sequence
<220> FEATURE:
<221> NAME/KEY: misc_feature
<222> LOCATION: (7871)..(7871)
<223> OTHER INFORMATION: Unknown sequence
<220> FEATURE:
<221> NAME/KEY: misc_feature
<222> LOCATION: (8042)..(8042)
<223> OTHER INFORMATION: Unknown sequence
<220> FEATURE:
<221> NAME/KEY: misc_feature
<222> LOCATION: (8075)..(8075)
<223> OTHER INFORMATION: Unknown sequence
<220> FEATURE:
<221> NAME/KEY: misc_feature
<222> LOCATION: (8109)..(8109)
<223> OTHER INFORMATION: Unknown sequence
<220> FEATURE:
<221> NAME/KEY: misc_feature
<222> LOCATION: (8113)..(8113)
<223> OTHER INFORMATION: Unknown sequence
<220> FEATURE:
<221> NAME/KEY: misc_feature
<222> LOCATION: (8145)..(8145)
<223> OTHER INFORMATION: Unknown sequence
<220> FEATURE:
<221> NAME/KEY: misc_feature
<222> LOCATION: (8167)..(8167)
```

```
<223> OTHER INFORMATION: Unknown sequence
<220> FEATURE:
<221> NAME/KEY: misc_feature
<222> LOCATION: (8216)..(8216)
<223> OTHER INFORMATION: Unknown sequence
<220> FEATURE:
<221> NAME/KEY: misc_feature
<222> LOCATION: (8235)..(8235)
<223> OTHER INFORMATION: Unknown sequence
<220> FEATURE:
<221> NAME/KEY: misc_feature
<222> LOCATION: (8289)..(8289)
<223> OTHER INFORMATION: Unknown sequence
<220> FEATURE:
<221> NAME/KEY: misc_feature
<222> LOCATION: (8290)..(8290)
<223> OTHER INFORMATION: Unknown sequence
<220> FEATURE:
<221> NAME/KEY: misc_feature
<222> LOCATION: (8291)..(8291)
<223> OTHER INFORMATION: Unknown sequence
<220> FEATURE:
<221> NAME/KEY: misc_feature
<222> LOCATION: (8350)..(8350)
<223> OTHER INFORMATION: Unknown sequence
<220> FEATURE:
<221> NAME/KEY: misc_feature
<222> LOCATION: (8444)..(8444)
<223> OTHER INFORMATION: Unknown sequence
<220> FEATURE:
<221> NAME/KEY: misc_feature
<222> LOCATION: (8445)..(8445)
<223> OTHER INFORMATION: Unknown sequence
<220> FEATURE:
<221> NAME/KEY: misc_feature
<222> LOCATION: (8464)..(8464)
<223> OTHER INFORMATION: Unknown sequence
<220> FEATURE:
<221> NAME/KEY: misc_feature
<222> LOCATION: (8465)..(8465)
<223> OTHER INFORMATION: Unknown sequence
<220> FEATURE:
<221> NAME/KEY: misc_feature
<222> LOCATION: (8466)..(8466)
<223> OTHER INFORMATION: Unknown sequence
<220> FEATURE:
<221> NAME/KEY: misc_feature
<222> LOCATION: (8467)..(8467)
<223> OTHER INFORMATION: Unknown sequence

<400> SEQUENCE: 3
```

| | | | | | |
|---|---|---|---|---|---|
| gccgctgagc | ctgcgcccag | tgccccgagc | cccgcgccga | gccgagtccg | cgccaagcag | 60 |
| cagccgccca | ccccggggcc | cggccggggg | accagcagct | tccccacagg | caacgtgagg | 120 |
| agagcctgtg | cccagaagca | ggatgagaag | atggcaaact | tcctattacc | tcggggcacc | 180 |
| agcagcttcc | gcaggttcac | acgggagtcc | ctggcagcca | tcgagaagcg | catggcggag | 240 |
| aagcaagccc | gcggctcaac | caccttgcag | gagagccgag | aggggctgcc | cgaggaggag | 300 |
| gctccccggc | cccagctgga | cctgcaggcc | tccaaaaagc | tgccagatct | ctatggcaat | 360 |
| ccaccccaag | agctcatcgg | agagcccctg | gaggacctgg | accccttcta | tagcacccaa | 420 |
| aagactttca | tcgtactgaa | taaaggcaag | accatcttcc | ggttcagtgc | caccaacgcc | 480 |
| ttgtatgtcc | tcagtcccct | tccacccagtt | cggagagcgg | ctgtgaagat | tctggttcac | 540 |
| tcgctcttca | acatgctcat | catgtgcacc | atcctcacca | actgcgtgtt | catggcccag | 600 |
| cacgaccctc | cacctggac | caagtatgtc | gagtacacct | tcaccgccat | ttacaccttt | 660 |
| gagtctctgg | tcaagattct | ggctcgagct | ttctgcctgc | acgcgttcac | tttccttcgg | 720 |
| gacccatgga | actggctgga | ctttagtgtg | attatcatgg | catacacaac | tgaatttgtg | 780 |
| gacctgggca | atgtctcagc | cttacgcacc | ttccgagtcc | tccgggccct | gaaaactata | 840 |

-continued

```
tcagtcattt cagggctgaa gaccatcgtg ggggccctga tccagtctgt gaagaagctg       900
gctgatgtga tggtcctcac agtcttctgc ctcagcgtct ttgccctcat cggcctgcag       960
ctcttcatgg caacctaag gcacaagtgt gtgcgcaact tcacagcgct caacggcacc      1020
aacggctccg tggaggccga cggcttggtc tgggaatccc tggacctta cctcagtgat      1080
ccagaaaatt acctgctcaa gaacggcacc tctgatgtgt tactgtgtgg aacagctct       1140
gacgctggga catgtccgga gggctaccgg tgcctaaagg caggcgagaa ccccgaccac      1200
ggctacacca gcttcgattc cttttgcctgg gcctttcttg cactcttccg cctgatgacg      1260
caggactgct gggagcgcct ctatcagcag accctcaggt ccgcagggaa gatctacatg      1320
atcttcttca tgcttgtcat cttcctgggg tccttctacc tggtgaacct gatcctggcc      1380
gtggtcgcaa tggcctatga ggagcaaaac caagccacca tcgctgagac cgaggagaag      1440
gaaaagcgct tccaggaggc catggaaatg ctcaagaaag aacacgaggc cctcaccatc      1500
agggggtgtgg ataccgtgtc ccgtagctcc ttggagatgt ccccttttggc cccagtaaac      1560
agccatgaga gaagaagcaa gaggagaaaa cggatgtctt caggaactga ggagtgtggg      1620
gaggacaggc tccccaagtc tgactcagaa gatggtccca gagcaatgaa tcatctcagc      1680
ctcacccgtg gcctcagcag gacttctatg aagccacgtt ccagccgcgg gagcattttc      1740
acctttcgca ggcgagacct gggttctgaa gcagattttg cagatgatga aaacagcaca      1800
gcgcgggaga gcgagagcca ccacacatca ctgctggtgc cctggcccct gcgccggacc      1860
agtgcccagg acagcccag tcccggaacc tcggctcctg gccacgccct ccatggcaaa      1920
aagaacagca ctgtggactg caatggggtg gtctcattac tggggcagg cgacccagag      1980
gccacatccc caggaagcca cctcctccgc cctgtgatgc tagagcaccc gccagacacg      2040
accacgccat cggaggagcc aggcggcccc cagatgctga cctcccaggc tccgtgtgta      2100
gatggcttcg aggagccagg agcacggcag cgggccctca gcgcagtcag cgtcctcaca      2160
agcgcactgg aagagttaga ggagtctcgc cacaagtgtc caccatgctg gaaccgtctc      2220
gcccagcgct acctgatctg ggagtgctgc ccgctgtgga tgtccatcaa gcagggagtg      2280
aagttggtgg tcatggaccc gtttactgac ctcaccatca ctatgtgcat cgtactcaac      2340
acactcttca tggcgctgga gcactacaac atgacaagtg aattcgagga gatgctgcag      2400
gtcggaaacc tggtcttcac agggattttc acagcagaga tgaccttcaa gatcattgcc      2460
ctcgacccct actactactt ccaacagggc tggaacatct tcgacagcat catcgtcatc      2520
cttagcctca tggagctggg cctgtcccgc atgagcaact tgtcggtgct gcgctccttc      2580
cgcctgctgc gggtcttcaa gctggccaaa tcatggccca ccctgaacac actcatcaag      2640
atcatcggga actcagtggg ggcactgggg aacctgacac tggtgctagc catcatcgtg      2700
ttcatctttg ctgtggtggg catgcagctc tttggcaaga actactcgga gctgagggac      2760
agcgactcag gcctgctgcc tcgctggcac atgatggact tctttcatgc cttcctaatc      2820
atcttccgca tcctctgtgg agagtggatc gagaccatgt gggactgcat ggaggtgtcg      2880
gggcagtcat tatgcctgct ggtcttcttg cttgttatgg tcattggcaa ccttgtggtc      2940
ctgaatctct tcctggcctt gctgctcagc tccttcagtg cagacaacct cacagcccct      3000
gatgaggaca gagagatgaa caacctccag ctggcccctgg cccgcatcca gaggggcctg      3060
cgctttgtca gcggaccac ctgggattc tgctgtggtc tcctgcggca ccggcctcag      3120
aagcccgcag cccttgccgc ccagggccag ctgcccagct gcattgccac cccctactcc      3180
```

```
ccgccacccc cagagacgga gaaggtgcct cccacccgca aggaaacaca gtttgaggaa    3240
ggcgagcaac caggccaggg cacccccggg gatccagagc ccgtgtgtgt gcccatcgct    3300
gtggccgagt cagacacaga tgaccaagaa gaggatgagg agaacagcct gggcacggag    3360
gaggagtcca gcaagcagca ggaatcccag cctgtgtccg gctggccagg aggccctccg    3420
gattccagga cctggagcca ggtgtcagcg actgcctcct ctgaggccga ggccagtgca    3480
tctcaggccg actggcggca gcagtggaaa gcggaacccc aggccccagg gtgcggtgag    3540
accccagagg acagttgctc cgagggcagc acagcagaca tgaccaacac cgctgagctc    3600
ctggagcaga tccctgacct cggccaggat gtcaaggacc cagaggactg cttcactgaa    3660
ggctgtgtcc ggcgctgtcc ctgctgtgcg gtggacacca cacaggcccc agggaaggtc    3720
tggtggcggt tgcgcaagac ctgctaccac atcgtggagc acagctggtt cgagacattc    3780
atcatcttca tgatcctact cagcagtgga gcgctggcct tcgaggacat ctacctagag    3840
gagcggaaga ccatcaaggt tctgcttgag tatgccgaca agatgttcac atatgtcttc    3900
gtgctggaga tgctgctcaa gtgggtggcc tacggcttca agaagtactt caccaatgcc    3960
tggtgctggc tcgacttcct catcgtagac gtctctctgg tcagcctggt ggccaacacc    4020
ctgggctttg ccgagatggg ccccatcaag tcactgcgga cgctgcgtgc actccgtcct    4080
ctgagagctc tgtcacgatt tgagggcatg agggtggtgg tcaatgccct ggtgggcgcc    4140
atcccgtcca tcatgaacgt cctcctcgtc tgcctcatct tctggctcat cttcagcatc    4200
atgggcgtga acctctttgc ggggaagttt ggggaggtgc atcaaccagac agagggagac    4260 ttgcctttga actacaccat cgtgaacaac aagagccagt gtgagtcctt gaacttgacc    4320
ggagaattgt actggaccaa ggtgaaagtc aactttgaca cgtggggggc cgggtacctg    4380
gcccttctgc aggtggcaac atttaaaggc tggatggaca ttatgtatgc agctgtggac    4440
tccagggggt atgaagagca gcctcagtgg gaatacaacc tctacatgta catctatttt    4500
gtcattttca tcatctttgg gtcttctctc accctgaacc tctttattgg tgtcatcatt    4560
gacaacttca accaacagaa gaaaaagtta gggggccagg acatcttcat gacagaggag    4620
cagaagaagt actacaatgc catgaagaag ctgggctcca agaagcccca gaagcccatc    4680
ccacggcccc tgaacaagta ccagggcttc atattcgaca ttgtgaccaa gcaggccttt    4740
gacgtcacca tcatgttttct gatctgcttg aatatggtga ccatgatggt ggagacagat    4800
gaccaaagtc ctgagaaaat caacatcttg gccaagatca acctgctctt tgtggccatc    4860
ttcacaggcg agtgtattgt caagctggct gccctgcgcc actactactt caccaacagc    4920
tggaatatct tcgacttcgt ggttgtcatc ctctccatcg tgggcactgt gctctcggac    4980
atcatccaga agtacttctt ctcccccgacg ctcttccgag tcatccgcct ggcccgaata    5040
ggccgcatcc tcagactgat ccgaggggcc aagggggatcc gcacgctgct ctttgccctc    5100
atgatgtccc tgcctgccct cttcaacatc gggctgctgc tcttcctcgt catgttcatc    5160
tactccatct ttggcatggc caacttcgct tatgtcaagt gggaggctgg catcgacgac    5220
atgttcaact tccagacctt cgccaacagc atgctgtgcc tcttccagat cacccacgtcg    5280 gccggctggg atggcctcct cagccccatc ctcaacactg gccgccccta ctgcgacccc    5340
actctgccca cagcaatgg ctctcggggg gactgcggga gccagccgt gggcatcctc    5400 ttcttcacca cctacatcat catctccttc ctcatcgtgg tcaacatgta cattgccatc    5460 atcctgaga acttcagcgt ggccacggag gagagcaccg agccctgag tgaggacgac    5520 ttcgatatgt tctatgagat ctgggagaaa tttgacccag aggccactca gtttattgag    5580
```

```
tattcggtcc tgtctgactt tgccgacgcc ctgtctgagc cactccgtat cgccaagccc    5640
aaccagataa gcctcatcaa catggacctg cccatggtga gtggggaccg catccattgc    5700
atggacattc tctttgcctt caccaaaagg gtcctggggg agtctgggga gatggacgcc    5760
ctgaagatcc agatggagga gaagttcatg gcagccaacc catccaagat ctcctacgag    5820
cccatcacca ccacactccg cgcaagcac aagaggtgt cggccatggt tatccagaga    5880
gccttccgca ggcacctgct gcaacgctct ttgaagcatg cctccttcct cttccgtcag    5940
caggcgggca gcggcctctc cgaagaggat gcccctgagc gagagggcct catcgcctac    6000
gtgatgagtg agaacttctc ccgacccctt ggcccaccct ccagctcctc catctcctcc    6060
acttccttcc caccctccta tgacagtgtc actagagcca ccagcgataa cctccaggtg    6120
cgggggtctg actacagcca cagtgaagat ctcgccgact tccccccttc tccggacagg    6180
gaccgtgagt ccatcgtgtg agcctcggcc tggctggcca ggacacactg aaaagcagcc    6240 ttttcacca tggcaaacct aaatgcagtc agtcacaaac cagcctgggg ccttcctggc    6300
tttgggagta agaaatgggc ctcggccccg cggatcaacc aggcagagtt ctgtggcgcc    6360
gcgtggacag ccggagcagt tggcctgtgc ttggaggcct cagatagacc tgtgacctgg    6420
tctggtcagg caatgcccct gcggctctgg aaagcaactt catcccagct gctgaggcga    6480
aatataaaac tgagactgta tatgttgtga atgggctttc ataaatttat tatatttgat    6540 attttttac ttgagcaaag aactaaggat ttttccatgg acatgggcag caattcacgc    6600
tgtctcttct taaccctgaa caagagtgtc tatggagcag ccggaagtct gttctcaaag    6660
cagaagtgga atccagtgtg gctcccacag gtcttcactg cccagggggtc gaatggggtc    6720 ccctccccac ttgacctgag atgctgggag ggctgaaccc ccactcacac aagcacacac    6780
acacacagtc ctcacacacg gaggccagac acaggccgtg ggacccaggc tcccagccta    6840
agggagacag gccttttccct gccggccccc caaggatggg gttcttgtcc acggggctca    6900
ctctggcccc ctattgtctc ccaaggtccc attttccccc ttgtgttttc acgcaggtca    6960
tattgtcagt cctacaaaaa taaaaggctt ccagaggaga gtggcctggg gtcccagggc    7020
tgggccntag gcactgatag ttgccttttc ttcccctcct gtaagagtat taacaaaacc    7080
aaaggacaca agggtgcaag ccccattcac ggcctggcat gcagcttgtc cttgctcctg    7140
gaacctggca ggccctgcca gccagccaat ggaagagagg ggctgagcca tgggggtttg    7200
gggctaagaa gttcaccagc cctgagccat ggsnsccctc agcctgcctg aagagaggaa    7260
actggcgatc tcccagggct ctctggacca tacncggagg agttttcnng tgtggtctcc    7320
agctcctctc cagacacaga gacatgggag tgggagcgg acgttggccc tggccctgtg    7380
cagggaaagg gatggtcagg cccagttctc gtgccccttta gagggaatg aaccatggca    7440 cctttgagag aggggggcact gtggtcaggc ccagcctctc tggcnnagtc ccgggatcct    7500
gatggcaccc acacagagga cctctttggg gcaagatcca ggtggntccc ataggtcttg    7560
tgaaaaggct ttttcaggga aaatatttt actagtccaa tcaccccag gacctcttca    7620 gctgctgaca atcctatta gcatatgcaa atcttttaac atagagaact gtcaccctga    7680
ggtaacaggg tcaactggcg aagagcaggc caggggcctt ggctgnncca ttccagctct    7740
nccacngann ncctccwmnc nnnnncatnn ctcccaggcc acctcagtct canctgccgg    7800
ctctgggctg gctnctccta acctacctnn ccgagctgtc ggagggctgg acatttgtgg    7860
cagtgctgaa nggggcattg snggcgagta aagtattakg tttcttcttg tcaccccagt    7920
```

-continued

```
tcccttggtg caaccccag acccaaccca tgcccctgac agatctagtt ctcttctsct    7980 gtgttcccttt tgagtccngt gtgggacacg gtttaactgt cccagcgaga tttctccaag  8040
tngaaatcct attttttgtag atctccatgc tttgnctctc aaggcttgga gaggtatgtg  8100
cccctcctng gbnctcaccg cctgctacac aggcaggaat gcggnttggg aggcaggtcg   8160
ggctssnagc ccagctggcc ggaaggagac tgtggttttt gtgtgtgtgg acagncggg    8220 agctttgaga caggntgcct ggggctggct gcagacggtg tggttggggg tgggaggtga   8280
gctagaccnn ncccttagct tttagcctgg ctgtcacctt tttaatttcc agaactgcac   8340
aatgaccagn aggaggggag aagagagtag gaaaaaggag ggaaggacag acatcaagtg   8400
ccagatgttg tctgaactaa tcgagcactt ctcaccaaac ttcnngtata aataaaatac   8460
atannnnggg gcaaaccaat aaatggctta c                                  8491
```

<210> SEQ ID NO 4
<211> LENGTH: 2016
<212> TYPE: PRT
<213> ORGANISM: Homo sapiens

<400> SEQUENCE: 4

```
Met Ala Asn Phe Leu Leu Pro Arg Gly Thr Ser Ser Phe Arg Arg Phe
1               5                   10                  15

Thr Arg Glu Ser Leu Ala Ala Ile Glu Lys Arg Met Ala Glu Lys Gln
            20                  25                  30

Ala Arg Gly Ser Thr Thr Leu Gln Glu Ser Arg Glu Gly Leu Pro Glu
        35                  40                  45

Glu Glu Ala Pro Arg Pro Gln Leu Asp Leu Gln Ala Ser Lys Lys Leu
    50                  55                  60

Pro Asp Leu Tyr Gly Asn Pro Pro Gln Glu Leu Ile Gly Glu Pro Leu
65                  70                  75                  80

Glu Asp Leu Asp Pro Phe Tyr Ser Thr Gln Lys Thr Phe Ile Val Leu
                85                  90                  95

Asn Lys Gly Lys Thr Ile Phe Arg Phe Ser Ala Thr Asn Ala Leu Tyr
            100                 105                 110

Val Leu Ser Pro Phe His Pro Val Arg Arg Ala Ala Val Lys Ile Leu
        115                 120                 125

Val His Ser Leu Phe Asn Met Leu Ile Met Cys Thr Ile Leu Thr Asn
    130                 135                 140

Cys Val Phe Met Ala Gln His Asp Pro Pro Trp Thr Lys Tyr Val
145                 150                 155                 160

Glu Tyr Thr Phe Thr Ala Ile Tyr Thr Phe Glu Ser Leu Val Lys Ile
                165                 170                 175

Leu Ala Arg Ala Phe Cys Leu His Ala Phe Thr Phe Leu Arg Asp Pro
            180                 185                 190

Trp Asn Trp Leu Asp Phe Ser Val Ile Met Ala Tyr Thr Thr Glu
        195                 200                 205

Phe Val Asp Leu Gly Asn Val Ser Ala Leu Arg Thr Phe Arg Val Leu
    210                 215                 220

Arg Ala Leu Lys Thr Ile Ser Val Ile Ser Gly Leu Lys Thr Ile Val
225                 230                 235                 240

Gly Ala Leu Ile Gln Ser Val Lys Lys Leu Ala Asp Val Met Val Leu
                245                 250                 255

Thr Val Phe Cys Leu Ser Val Phe Ala Leu Ile Gly Leu Gln Leu Phe
            260                 265                 270
```

-continued

```
Met Gly Asn Leu Arg His Lys Cys Val Arg Asn Phe Thr Ala Leu Asn
            275                 280                 285
Gly Thr Asn Gly Ser Val Glu Ala Asp Gly Leu Val Trp Glu Ser Leu
        290                 295                 300
Asp Leu Tyr Leu Ser Asp Pro Glu Asn Tyr Leu Leu Lys Asn Gly Thr
305                 310                 315                 320
Ser Asp Val Leu Leu Cys Gly Asn Ser Ser Asp Ala Gly Thr Cys Pro
                325                 330                 335
Glu Gly Tyr Arg Cys Leu Lys Ala Gly Glu Asn Pro Asp His Gly Tyr
            340                 345                 350
Thr Ser Phe Asp Ser Phe Ala Trp Ala Phe Leu Ala Leu Phe Arg Leu
        355                 360                 365
Met Thr Gln Asp Cys Trp Glu Arg Leu Tyr Gln Gln Thr Leu Arg Ser
    370                 375                 380
Ala Gly Lys Ile Tyr Met Ile Phe Phe Met Leu Val Ile Phe Leu Gly
385                 390                 395                 400
Ser Phe Tyr Leu Val Asn Leu Ile Leu Ala Val Val Ala Met Ala Tyr
                405                 410                 415
Glu Glu Gln Asn Gln Ala Thr Ile Ala Glu Thr Glu Glu Lys Glu Lys
            420                 425                 430
Arg Phe Gln Glu Ala Met Glu Met Leu Lys Lys Glu His Glu Ala Leu
        435                 440                 445
Thr Ile Arg Gly Val Asp Thr Val Ser Arg Ser Ser Leu Glu Met Ser
    450                 455                 460
Pro Leu Ala Pro Val Asn Ser His Glu Arg Arg Ser Lys Arg Arg Lys
465                 470                 475                 480
Arg Met Ser Ser Gly Thr Glu Glu Cys Gly Glu Asp Arg Leu Pro Lys
                485                 490                 495
Ser Asp Ser Glu Asp Gly Pro Arg Ala Met Asn His Leu Ser Leu Thr
            500                 505                 510
Arg Gly Leu Ser Arg Thr Ser Met Lys Pro Arg Ser Ser Arg Gly Ser
        515                 520                 525
Ile Phe Thr Phe Arg Arg Arg Asp Leu Gly Ser Glu Ala Asp Phe Ala
    530                 535                 540
Asp Asp Glu Asn Ser Thr Ala Arg Glu Ser Glu Ser His His Thr Ser
545                 550                 555                 560
Leu Leu Val Pro Trp Pro Leu Arg Arg Thr Ser Ala Gln Gly Gln Pro
                565                 570                 575
Ser Pro Gly Thr Ser Ala Pro Gly His Ala Leu His Gly Lys Lys Asn
            580                 585                 590
Ser Thr Val Asp Cys Asn Gly Val Val Ser Leu Leu Gly Ala Gly Asp
        595                 600                 605
Pro Glu Ala Thr Ser Pro Gly Ser His Leu Leu Arg Pro Val Met Leu
    610                 615                 620
Glu His Pro Pro Asp Thr Thr Thr Pro Ser Glu Glu Pro Gly Gly Pro
625                 630                 635                 640
Gln Met Leu Thr Ser Gln Ala Pro Cys Val Asp Gly Phe Glu Glu Pro
                645                 650                 655
Gly Ala Arg Gln Arg Ala Leu Ser Ala Val Ser Val Leu Thr Ser Ala
            660                 665                 670
Leu Glu Glu Leu Glu Glu Ser Arg His Lys Cys Pro Pro Cys Trp Asn
        675                 680                 685
Arg Leu Ala Gln Arg Tyr Leu Ile Trp Glu Cys Cys Pro Leu Trp Met
```

```
              690             695             700
Ser Ile Lys Gln Gly Val Lys Leu Val Val Met Asp Pro Phe Thr Asp
705             710             715             720

Leu Thr Ile Thr Met Cys Ile Val Leu Asn Thr Leu Phe Met Ala Leu
                725             730             735

Glu His Tyr Asn Met Thr Ser Glu Phe Glu Glu Met Leu Gln Val Gly
                740             745             750

Asn Leu Val Phe Thr Gly Ile Phe Thr Ala Glu Met Thr Phe Lys Ile
                755             760             765

Ile Ala Leu Asp Pro Tyr Tyr Tyr Phe Gln Gln Gly Trp Asn Ile Phe
770             775             780

Asp Ser Ile Ile Val Ile Leu Ser Leu Met Glu Leu Gly Leu Ser Arg
785             790             795             800

Met Ser Asn Leu Ser Val Leu Arg Ser Phe Arg Leu Leu Arg Val Phe
                805             810             815

Lys Leu Ala Lys Ser Trp Pro Thr Leu Asn Thr Leu Ile Lys Ile Ile
                820             825             830

Gly Asn Ser Val Gly Ala Leu Gly Asn Leu Thr Leu Val Leu Ala Ile
                835             840             845

Ile Val Phe Ile Phe Ala Val Val Gly Met Gln Leu Phe Gly Lys Asn
850             855             860

Tyr Ser Glu Leu Arg Asp Ser Asp Ser Gly Leu Leu Pro Arg Trp His
865             870             875             880

Met Met Asp Phe Phe His Ala Phe Leu Ile Ile Phe Arg Ile Leu Cys
                885             890             895

Gly Glu Trp Ile Glu Thr Met Trp Asp Cys Met Glu Val Ser Gly Gln
                900             905             910

Ser Leu Cys Leu Leu Val Phe Leu Leu Val Met Val Ile Gly Asn Leu
                915             920             925

Val Val Leu Asn Leu Phe Leu Ala Leu Leu Leu Ser Ser Phe Ser Ala
                930             935             940

Asp Asn Leu Thr Ala Pro Asp Glu Asp Arg Glu Met Asn Asn Leu Gln
945             950             955             960

Leu Ala Leu Ala Arg Ile Gln Arg Gly Leu Arg Phe Val Lys Arg Thr
                965             970             975

Thr Trp Asp Phe Cys Cys Gly Leu Leu Arg His Arg Pro Gln Lys Pro
                980             985             990

Ala Ala Leu Ala Ala Gln Gly Gln Leu Pro Ser Cys Ile Ala Thr Pro
                995            1000            1005

Tyr Ser Pro Pro Pro Pro Glu Thr Glu Lys Val Pro Pro Thr Arg
       1010            1015            1020

Lys Glu Thr Gln Phe Glu Glu Gly Glu Gln Pro Gly Gln Gly Thr
       1025            1030            1035

Pro Gly Asp Pro Glu Pro Val Cys Val Pro Ile Ala Val Ala Glu
       1040            1045            1050

Ser Asp Thr Asp Asp Gln Glu Glu Asp Glu Glu Asn Ser Leu Gly
       1055            1060            1065

Thr Glu Glu Glu Ser Ser Lys Gln Gln Glu Ser Gln Pro Val Ser
       1070            1075            1080

Gly Trp Pro Arg Gly Pro Pro Asp Ser Arg Thr Trp Ser Gln Val
       1085            1090            1095

Ser Ala Thr Ala Ser Ser Glu Ala Glu Ala Ser Ala Ser Gln Ala
       1100            1105            1110
```

```
Asp Trp Arg Gln Gln Trp Lys Ala Glu Pro Gln Ala Pro Gly Cys
    1115                1120                1125

Gly Glu Thr Pro Glu Asp Ser Cys Ser Glu Gly Ser Thr Ala Asp
    1130                1135                1140

Met Thr Asn Thr Ala Glu Leu Leu Glu Gln Ile Pro Asp Leu Gly
    1145                1150                1155

Gln Asp Val Lys Asp Pro Glu Asp Cys Phe Thr Glu Gly Cys Val
    1160                1165                1170

Arg Arg Cys Pro Cys Cys Ala Val Asp Thr Thr Gln Ala Pro Gly
    1175                1180                1185

Lys Val Trp Trp Arg Leu Arg Lys Thr Cys Tyr His Ile Val Glu
    1190                1195                1200

His Ser Trp Phe Glu Thr Phe Ile Ile Phe Met Ile Leu Leu Ser
    1205                1210                1215

Ser Gly Ala Leu Ala Phe Glu Asp Ile Tyr Leu Glu Glu Arg Lys
    1220                1225                1230

Thr Ile Lys Val Leu Leu Glu Tyr Ala Asp Lys Met Phe Thr Tyr
    1235                1240                1245

Val Phe Val Leu Glu Met Leu Leu Lys Trp Val Ala Tyr Gly Phe
    1250                1255                1260

Lys Lys Tyr Phe Thr Asn Ala Trp Cys Trp Leu Asp Phe Leu Ile
    1265                1270                1275

Val Asp Val Ser Leu Val Ser Leu Val Ala Asn Thr Leu Gly Phe
    1280                1285                1290

Ala Glu Met Gly Pro Ile Lys Ser Leu Arg Thr Leu Arg Ala Leu
    1295                1300                1305

Arg Pro Leu Arg Ala Leu Ser Arg Phe Glu Gly Met Arg Val Val
    1310                1315                1320

Val Asn Ala Leu Val Gly Ala Ile Pro Ser Ile Met Asn Val Leu
    1325                1330                1335

Leu Val Cys Leu Ile Phe Trp Leu Ile Phe Ser Ile Met Gly Val
    1340                1345                1350

Asn Leu Phe Ala Gly Lys Phe Gly Arg Cys Ile Asn Gln Thr Glu
    1355                1360                1365

Gly Asp Leu Pro Leu Asn Tyr Thr Ile Val Asn Asn Lys Ser Gln
    1370                1375                1380

Cys Glu Ser Leu Asn Leu Thr Gly Glu Leu Tyr Trp Thr Lys Val
    1385                1390                1395

Lys Val Asn Phe Asp Asn Val Gly Ala Gly Tyr Leu Ala Leu Leu
    1400                1405                1410

Gln Val Ala Thr Phe Lys Gly Trp Met Asp Ile Met Tyr Ala Ala
    1415                1420                1425

Val Asp Ser Arg Gly Tyr Glu Glu Gln Pro Gln Trp Glu Tyr Asn
    1430                1435                1440

Leu Tyr Met Tyr Ile Tyr Phe Val Ile Phe Ile Ile Phe Gly Ser
    1445                1450                1455

Phe Phe Thr Leu Asn Leu Phe Ile Gly Val Ile Ile Asp Asn Phe
    1460                1465                1470

Asn Gln Gln Lys Lys Lys Leu Gly Gly Gln Asp Ile Phe Met Thr
    1475                1480                1485

Glu Glu Gln Lys Lys Tyr Tyr Asn Ala Met Lys Lys Leu Gly Ser
    1490                1495                1500
```

-continued

```
Lys Lys Pro Gln Lys Pro Ile Pro Arg Pro Leu Asn Lys Tyr Gln
1505                1510                1515

Gly Phe Ile Phe Asp Ile Val Thr Lys Gln Ala Phe Asp Val Thr
    1520                1525                1530

Ile Met Phe Leu Ile Cys Leu Asn Met Val Thr Met Met Val Glu
    1535                1540                1545

Thr Asp Asp Gln Ser Pro Glu Lys Ile Asn Ile Leu Ala Lys Ile
    1550                1555                1560

Asn Leu Leu Phe Val Ala Ile Phe Thr Gly Glu Cys Ile Val Lys
    1565                1570                1575

Leu Ala Ala Leu Arg His Tyr Tyr Phe Thr Asn Ser Trp Asn Ile
    1580                1585                1590

Phe Asp Phe Val Val Val Ile Leu Ser Ile Val Gly Thr Val Leu
    1595                1600                1605

Ser Asp Ile Ile Gln Lys Tyr Phe Phe Ser Pro Thr Leu Phe Arg
    1610                1615                1620

Val Ile Arg Leu Ala Arg Ile Gly Arg Ile Leu Arg Leu Ile Arg
    1625                1630                1635

Gly Ala Lys Gly Ile Arg Thr Leu Leu Phe Ala Leu Met Met Ser
    1640                1645                1650

Leu Pro Ala Leu Phe Asn Ile Gly Leu Leu Phe Leu Val Met
    1655                1660                1665

Phe Ile Tyr Ser Ile Phe Gly Met Ala Asn Phe Ala Tyr Val Lys
    1670                1675                1680

Trp Glu Ala Gly Ile Asp Asp Met Phe Asn Phe Gln Thr Phe Ala
    1685                1690                1695

Asn Ser Met Leu Cys Leu Phe Gln Ile Thr Thr Ser Ala Gly Trp
    1700                1705                1710

Asp Gly Leu Leu Ser Pro Ile Leu Asn Thr Gly Pro Pro Tyr Cys
    1715                1720                1725

Asp Pro Thr Leu Pro Asn Ser Asn Gly Ser Arg Gly Asp Cys Gly
    1730                1735                1740

Ser Pro Ala Val Gly Ile Leu Phe Phe Thr Thr Tyr Ile Ile Ile
    1745                1750                1755

Ser Phe Leu Ile Val Val Asn Met Tyr Ile Ala Ile Ile Leu Glu
    1760                1765                1770

Asn Phe Ser Val Ala Thr Glu Glu Ser Thr Glu Pro Leu Ser Glu
    1775                1780                1785

Asp Asp Phe Asp Met Phe Tyr Glu Ile Trp Glu Lys Phe Asp Pro
    1790                1795                1800

Glu Ala Thr Gln Phe Ile Glu Tyr Ser Val Leu Ser Asp Phe Ala
    1805                1810                1815

Asp Ala Leu Ser Glu Pro Leu Arg Ile Ala Lys Pro Asn Gln Ile
    1820                1825                1830

Ser Leu Ile Asn Met Asp Leu Pro Met Val Ser Gly Asp Arg Ile
    1835                1840                1845

His Cys Met Asp Ile Leu Phe Ala Phe Thr Lys Arg Val Leu Gly
    1850                1855                1860

Glu Ser Gly Glu Met Asp Ala Leu Lys Ile Gln Met Glu Glu Lys
    1865                1870                1875

Phe Met Ala Ala Asn Pro Ser Lys Ile Ser Tyr Glu Pro Ile Thr
    1880                1885                1890

Thr Thr Leu Arg Arg Lys His Glu Glu Val Ser Ala Met Val Ile
```

```
                 1895                1900                1905

Gln Arg  Ala Phe Arg Arg His  Leu Leu Gln Arg Ser  Leu Lys His
    1910                1915                1920

Ala Ser  Phe Leu Phe Arg Gln  Gln Ala Gly Ser Gly  Leu Ser Glu
    1925                1930                1935

Glu Asp  Ala Pro Glu Arg Glu  Gly Leu Ile Ala Tyr  Val Met Ser
    1940                1945                1950

Glu Asn  Phe Ser Arg Pro Leu  Gly Pro Pro Ser Ser  Ser Ser Ile
    1955                1960                1965

Ser Ser  Thr Ser Phe Pro Pro  Ser Tyr Asp Ser Val  Thr Arg Ala
    1970                1975                1980

Thr Ser  Asp Asn Leu Gln Val  Arg Gly Ser Asp Tyr  Ser His Ser
    1985                1990                1995

Glu Asp  Leu Ala Asp Phe Pro  Pro Ser Pro Asp Arg  Asp Arg Glu
    2000                2005                2010

Ser Ile  Val
    2015

<210> SEQ ID NO 5
<211> LENGTH: 7008
<212> TYPE: DNA
<213> ORGANISM: Homo sapiens

<400> SEQUENCE: 5
gagcgctcca agatggcgcc caccgcagtc ccgcccgccg catcctcggc gcctttgcag      60
tccggccgcg cctcccgggc cccgcgttag ggccgccgct gcctccctcg ccgccgccgc     120
tgccagctga cctgtcctgg acgcagcata actaacgaag ctgctgcagg atgagaagat     180
ggcagcgcgg ctgcttgcac caccaggccc tgatagtttc aagcctttca cccctgagtc     240
actggcaaac attgagaggc gcattgctga gagcaagctc aagaaaccac caaaggccga     300
tggcagtcat cgggaggacg atgaggacag caagcccaag ccaaacagcg acctggaagc     360
agggaagagt ttgcctttca tctacgggga catcccccaa ggcctggttg cagttcccct     420
ggaggacttt gacccatact atttgacgca gaaaaccttt gtagtattaa acagagggaa     480
aactctcttc agatttagtg ccacgcctgc cttgtacatt ttaagtcctt ttaacctgat     540
aagaagaata gctattaaaa ttttgataca ttcagtattt agcatgatca ttatgtgcac     600
tattttgacc aactgtgtat tcatgacttt tagtaaccct cctgactggt cgaagaatgt     660
ggagtacacg ttcacaggga tttatacatt tgaatcacta gtgaaaatca ttgcaagagg     720
tttctgcata gatggcttta ccttttttacg ggatccatgg aactggttag atttcagtgt     780
catcatgatg gcgtatataa cagagtttgt aaacctaggc aatgtttcag ctctacgcac     840
tttcagggta ctgagggctt tgaaaactat ttcggtaatc ccaggcctga gacaattgt      900 gggtgccctg attcagtctg tgaagaaact gtcagatgtg atgatcctga cagtgttctg     960
cctgagtgtt tttgccttga tcggactgca gctgttcatg gggaaccttc gaaacaagtg    1020
tgttgtgtgg cccataaact tcaacgagag ctatcttgaa aatggcacca aaggctttga    1080
ttgggaagag tatatcaaca ataaaacaaa tttctacaca gttcctggca tgctggaacc    1140
tttactctgt gggaacagtt ctgatgctgg gcaatgccca gagggatacc agtgtatgaa    1200
agcaggaagg aaccccaact atggttacac aagttttgac acttttagct gggccttctt    1260
ggcattattt cgcctatga cccaggacta ttgggaaaac ttgtatcaat tgactttacg    1320
agcagccggg aaaacataca tgatcttctt cgtcttggtc atctttgtgg gttctttcta    1380
```

```
tctggtgaac ttgatcttgg ctgtggtggc catggcttat gaagaacaga atcaggcaac    1440
actggaggag gcagaacaaa aagaggctga atttaaagca atgttggagc aacttaagaa    1500
gcaacaggaa gaggcacagg ctgctgcgat ggccacttca gcaggaactg tctcagaaga    1560
tgccatagag gaagaaggtg aagaaggagg gggctcccct cggagctctt ctgaaatctc    1620
taaactcagc tcaaagagtg caaaggaaag acgtaacagg agaaagaaga ggaagcaaaa    1680
ggaactctct gaaggagagg agaaagggga tcccgagaag gtgtttaagt cagagtcaga    1740
agatggcatg agaaggaagg cctttcggct gccagacaac agaatagggg ggaaattttc    1800
catcatgaat cagtcactgc tcagcatccc aggctcgccc ttcctctccc gccacaacag    1860
caagagcagc atcttcagtt tcaggggacc tgggcggttc cgagacccgg gctccgagaa    1920
tgagttcgcg gatgacgagc acagcacggt ggaggagagc gagggccgcc gggactccct    1980
cttcatcccc atccgggccc gcgagcgccg gagcagctac agcggctaca gcggctacag    2040
ccagggcagc cgctcctcgc gcatcttccc cagcctgcgg cgcagcgtga gcgcaacag    2100 cacggtggac tgcaacggcg tggtgtccct catcggcggc cccggctccc acatcggcgg    2160
gcgtctcctg ccagaggcta caactgaggt ggaaattaag aagaaaggcc ctggatctct    2220
tttagtttcc atggaccaat tagcctccta cgggcggaag gacagaatca acagtataat    2280
gagtgttgtt acaaatacac tagtagaaga actggaagag tctcagagaa agtgcccgcc    2340
atgctggtat aaatttgcca acactttcct catctgggag tgccacccct actggataaa    2400
actgaaagag attgtgaact tgatagttat ggacccttt gtggatttag ccatcaccat    2460
ctgcatcgtc ctgaatacac tgtttatggc aatggagcac catcctatga caccacaatt    2520
tgaacatgtc ttggctgtag gaaatctggt tttcactgga attttcacag cggaaatgtt    2580
cctgaagctc atagccatgg atccctacta ttatttccaa gaaggttgga acattttga    2640 cggatttatt gtctccctca gtttaatgga actgagtcta gcagacgtgg aggggctttc    2700
agtgctgcga tctttccgat tgctccgagt cttcaaattg gccaaatcct ggcccaccct    2760
gaacatgcta atcaagatta ttggaaattc agtgggtgcc ctgggcaacc tgacactggt    2820
gctggccatt attgtcttca tctttgccgt ggtggggatg caactctttg gaaaaagcta    2880
caaagagtgt gtctgcaaga tcaaccagga ctgtgaactc cctcgctggc atatgcatga    2940 cttttttccat tccttcctca ttgtctttcg agtgttgtgc ggggagtgga ttgagaccat    3000
gtgggactgc atggaagtgg caggccaggc catgtgcctc attgtcttta tgatggtcat    3060
ggtgattggc aacttggtgg tgctgaacct gtttctggcc ttgctcctga gctccttcag    3120
tgcagacaac ctggctgcca cagatgacga tggggaaatg aacaacctcc agatctcagt    3180
gatccgtatc aagaagggtg tggcctggac aaaactaaag gtgcacgcct tcatgcaggc    3240
ccactttaag cagcgtgagg ctgatgaggt gaagcctctg gatgagttgt atgaaaagaa    3300
ggccaactgt atcgccaatc acaccggtgc agacatccac cggaatggtg acttccagaa    3360
gaatggcaat ggcacaacca gcggcattgg cagcagcgtg gagaagtaca tcattgatga    3420
ggaccacatg tccttcatca acaaccccaa cttgactgta cgggtaccca ttgctgtggg    3480
cgagtctgac tttgagaacc tcaacacaga ggatgttagc agcgagtcgg atcctgaagg    3540
cagcaaagat aaaactagatg acaccagctc ctctgaagga agcaccattg atatcaaacc    3600
agaagtagaa gaggtccctg tggaacagct tgaggaatac ttggatccag atgcctgctt    3660
cacagaaggt tgtgtccagc ggttcaagtg ctgccaggtc aacatcgagg aagggctagg    3720
```

```
caagtcttgg tggatcctgc ggaaaacctg cttcctcatc gtggagcaca actggtttga    3780
gaccttcatc atcttcatga ttctgctgag cagtggcgcc ctggccttcg aggacatcta    3840
cattgagcag agaaagacca tccgcaccat cctggaatat gctgacaaag tcttcaccta    3900
tatcttcatc ctggagatgt tgctcaagtg gacagcctat ggcttcgtca agttcttcac    3960
caatgcctgg tgttggctgg acttcctcat tgtggctgtc tctttagtca gccttatagc    4020
taatgccctg ggctactcgg aactaggtgc cataaagtcc cttaggaccc taagagcttt    4080
gagacccta agagcctat cacgatttga agggatgagg gtggtggtga atgccttggt    4140
gggcgccatc ccctccatca tgaatgtgct gctggtgtgt ctcatcttct ggctgatttt    4200
cagcatcatg ggagttaact tgtttgcggg aaagtaccac tactgcttta atgagacttc    4260
tgaaatccga tttgaaattg aagatgtcaa caataaaact gaatgtgaaa agcttatgga    4320
ggggaacaat acagagatca gatggaagaa cgtgaagatc aactttgaca atgttggggc    4380
aggatacctg gccttcttc aagtagcaac cttcaaaggc tggatggaca tcatgtatgc    4440
agctgtagat tcccggaagc ctgatgagca gcctaagtat gaggacaata tctacatgta    4500
catctatttt gtcatcttca tcatcttcgg ctccttcttc accctgaacc tgttcattgg    4560
tgtcatcatt gataacttca atcaacaaaa gaaaaagttc ggaggtcagg acatcttcat    4620
gaccgaagaa cagaagaagt actacaatgc catgaaaaag ctgggctcaa gaagccaca    4680
gaaacccatt ccccgcccct tgaacaaaat ccaggaatc gtctttgatt tgtcactca    4740
gcaagccttt gacattgtta tcatgatgct catctgcctt aacatggtga caatgatggt    4800
ggagacagac actcaaagca agcagatgga gaacatcctc tactggatta acctggtgtt    4860
tgttatcttc ttcaccctgtg agtgtgtgct caaaatgttt gcgttgaggc actactactt    4920
caccattggc tggaacatct tcgacttcgt ggtagtcatc ctctccattg tgggaatgtt    4980
cctggcagat ataattgaga aatactttgt ttccccaacc ctattccgag tcatccgatt    5040
ggccccgtatt gggcgcatct tgcgtctgat caaaggcgcc aaagggattc gtaccctgct    5100
ctttgccctta atgatgtcct tgcctgccct gttcaacatc ggccttctgc tcttcctggt    5160
catgttcatc ttctccattt ttgggatgtc caatttttgca tatgtgaagc acgaggctgg    5220
tatcgatgac atgttcaact ttgagacatt tggcaacagc atgatctgcc tgtttcaaat    5280
cacaacctca gctggttggg atggcctgct gctgcccatc ctaaaccgcc ccctgactg    5340
cagcctagat aaggaacacc cagggagtgg ctttaaggga gattgtggga accccctagt    5400
gggcatcttc ttctttgtaa gctacatcat catctctttc ctaattgtcg tgaacatgta    5460
cattgccatc atcctggaga acttcagtgt agccacagag gaaagtgcag accctctgag    5520
tgaggatgac tttgagacct tctatgagat ctgggagaag ttcgaccccg atgccaccca    5580
gttcattgag tactgtaagc tggcagactt tgcagatgcc ttggagcatc tctccgagt    5640
gcccaagcca ataccattg agctcatcgc tatggatctg ccaatggtga gcgggatcg    5700
catccactgc ttggacatcc tttttgcctt caccaagcgg gtcctgggag atagcgggga    5760
gttggacatc ctgcggcagc agatggaaga gcggttcgtg gcatccaatc cttccaaagt    5820
gtcttacgag ccaatcacaa ccacactgcg tcgcaagcag gaggaggtat ctgcagtggt    5880
cctgcagcgt gcctaccggg gacatttggc aaggcgggc ttcatctgca aaaagacaac    5940
ttctaataag ctggagaatg gaggcacaca ccgggagaaa aagagagca ccccatctac    6000
agcctccctc ccgtcctatg acagtgtaac taaacctgaa aaggagaaac agcagcgggc    6060
agaggaagga agaagggaaa gagccaaaag acaaaaagag gtcagagaat ccaagtgtta    6120
```

```
gaggagaaca aaaattcagt attatacaga tctaaaactc gcaagtgaaa gattgtttac    6180
aaacttcctg aatattatca atgcagaaca gctgtggaga ctctaacctg aagatctata    6240
ccaaacgtcg tctgcttacc acgtaacaca gctgcatctt gagcagtgac ctgccaaggg    6300
caaaggaccc cgctccctag acttacagat tttctaatgc ttgggcaggt ggttactgca    6360
tgttccacat cagtcaatgc aacttaggac aaaactaacc agatacagaa acagaagaga    6420
ggctgccggg accagcatat ttccgttgca gccaaatgga ttttattttt tcattttatt    6480
gattctcaga agcagaaagc atcactttaa aagttcgttt gttcatgcaa actatatttg    6540
cattcttaca ttagttaagc taagcagcaa aaagaaaaca cacacacaca ctcacattta    6600
gcccatgtca tttaattgtc agtttctttg acataaagcg catcttctcc acatgggctt    6660
cacgtggttt ggagatgggt gggggaaaac aatcaggttt cttcaggctg aggaggactt    6720
gctcaggccg attccaaaca ttgtgctcgt tcaatgcgta gaaatgattt gcatgatggc    6780
atgccgtgat cagaagtcat gcatgagatc catacaccac aggacactac taatctagtc    6840
ccttgcactg ggtcagcctt tggacaggac ccagccctgc accgttcact gtatttggag    6900
aaaatggtaa gagttccata ccgggctaca attctttgag ttcttaaaag tccttcatac    6960
accttctggg tagggaaaca accaactaat tgactaacac caccaacg              7008
```

<210> SEQ ID NO 6
<211> LENGTH: 1980
<212> TYPE: PRT
<213> ORGANISM: Homo sapiens

<400> SEQUENCE: 6

Met Ala Ala Arg Leu Leu Ala Pro Pro Gly Pro Asp Ser Phe Lys Pro
1               5                   10                  15

Phe Thr Pro Glu Ser Leu Ala Asn Ile Glu Arg Arg Ile Ala Glu Ser
                20                  25                  30

Lys Leu Lys Lys Pro Pro Lys Ala Asp Gly Ser His Arg Glu Asp Asp
            35                  40                  45

Glu Asp Ser Lys Pro Lys Pro Asn Ser Asp Leu Glu Ala Gly Lys Ser
        50                  55                  60

Leu Pro Phe Ile Tyr Gly Asp Ile Pro Gln Gly Leu Val Ala Val Pro
65                  70                  75                  80

Leu Glu Asp Phe Asp Pro Tyr Tyr Leu Thr Gln Lys Thr Phe Val Val
                85                  90                  95

Leu Asn Arg Gly Lys Thr Leu Phe Arg Phe Ser Ala Thr Pro Ala Leu
            100                 105                 110

Tyr Ile Leu Ser Pro Phe Asn Leu Ile Arg Arg Ile Ala Ile Lys Ile
            115                 120                 125

Leu Ile His Ser Val Phe Ser Met Ile Ile Met Cys Thr Ile Leu Thr
        130                 135                 140

Asn Cys Val Phe Met Thr Phe Ser Asn Pro Pro Asp Trp Ser Lys Asn
145                 150                 155                 160

Val Glu Tyr Thr Phe Thr Gly Ile Tyr Thr Phe Glu Ser Leu Val Lys
                165                 170                 175

Ile Ile Ala Arg Gly Phe Cys Ile Asp Gly Phe Thr Phe Leu Arg Asp
            180                 185                 190

Pro Trp Asn Trp Leu Asp Phe Ser Val Ile Met Met Ala Tyr Ile Thr
        195                 200                 205

Glu Phe Val Asn Leu Gly Asn Val Ser Ala Leu Arg Thr Phe Arg Val

-continued

```
             210                 215                 220
Leu Arg Ala Leu Lys Thr Ile Ser Val Ile Pro Gly Leu Lys Thr Ile
225                 230                 235                 240

Val Gly Ala Leu Ile Gln Ser Val Lys Lys Leu Ser Asp Val Met Ile
                245                 250                 255

Leu Thr Val Phe Cys Leu Ser Val Phe Ala Leu Ile Gly Leu Gln Leu
                260                 265                 270

Phe Met Gly Asn Leu Arg Asn Lys Cys Val Val Trp Pro Ile Asn Phe
                275                 280                 285

Asn Glu Ser Tyr Leu Glu Asn Gly Thr Lys Gly Phe Asp Trp Glu Glu
                290                 295                 300

Tyr Ile Asn Asn Lys Thr Asn Phe Tyr Thr Val Pro Gly Met Leu Glu
305                 310                 315                 320

Pro Leu Leu Cys Gly Asn Ser Ser Asp Ala Gly Gln Cys Pro Glu Gly
                325                 330                 335

Tyr Gln Cys Met Lys Ala Gly Arg Asn Pro Asn Tyr Gly Tyr Thr Ser
                340                 345                 350

Phe Asp Thr Phe Ser Trp Ala Phe Leu Ala Leu Phe Arg Leu Met Thr
                355                 360                 365

Gln Asp Tyr Trp Glu Asn Leu Tyr Gln Leu Thr Leu Arg Ala Ala Gly
                370                 375                 380

Lys Thr Tyr Met Ile Phe Phe Val Leu Val Ile Phe Val Gly Ser Phe
385                 390                 395                 400

Tyr Leu Val Asn Leu Ile Leu Ala Val Val Ala Met Ala Tyr Glu Glu
                405                 410                 415

Gln Asn Gln Ala Thr Leu Glu Glu Ala Glu Gln Lys Glu Ala Glu Phe
                420                 425                 430

Lys Ala Met Leu Glu Gln Leu Lys Lys Gln Gln Glu Glu Ala Gln Ala
                435                 440                 445

Ala Ala Met Ala Thr Ser Ala Gly Thr Val Ser Glu Asp Ala Ile Glu
                450                 455                 460

Glu Glu Gly Glu Glu Gly Gly Gly Ser Pro Arg Ser Ser Ser Glu Ile
465                 470                 475                 480

Ser Lys Leu Ser Ser Lys Ser Ala Lys Glu Arg Arg Asn Arg Arg Lys
                485                 490                 495

Lys Arg Lys Gln Lys Glu Leu Ser Glu Gly Glu Lys Gly Asp Pro
                500                 505                 510

Glu Lys Val Phe Lys Ser Glu Ser Glu Asp Gly Met Arg Arg Lys Ala
                515                 520                 525

Phe Arg Leu Pro Asp Asn Arg Ile Gly Arg Lys Phe Ser Ile Met Asn
530                 535                 540

Gln Ser Leu Leu Ser Ile Pro Gly Ser Pro Phe Leu Ser Arg His Asn
545                 550                 555                 560

Ser Lys Ser Ser Ile Phe Ser Phe Arg Gly Pro Gly Arg Phe Arg Asp
                565                 570                 575

Pro Gly Ser Glu Asn Glu Phe Ala Asp Asp Glu His Ser Thr Val Glu
                580                 585                 590

Glu Ser Glu Gly Arg Arg Asp Ser Leu Phe Ile Pro Ile Arg Ala Arg
                595                 600                 605

Glu Arg Arg Ser Ser Tyr Ser Gly Tyr Ser Gly Tyr Ser Gln Gly Ser
                610                 615                 620

Arg Ser Ser Arg Ile Phe Pro Ser Leu Arg Arg Ser Val Lys Arg Asn
625                 630                 635                 640
```

-continued

Ser Thr Val Asp Cys Asn Gly Val Ser Leu Ile Gly Pro Gly
            645                 650                 655

Ser His Ile Gly Gly Arg Leu Leu Pro Glu Ala Thr Thr Glu Val Glu
            660                 665                 670

Ile Lys Lys Lys Gly Pro Gly Ser Leu Leu Val Ser Met Asp Gln Leu
            675                 680                 685

Ala Ser Tyr Gly Arg Lys Asp Arg Ile Asn Ser Ile Met Ser Val Val
        690                 695                 700

Thr Asn Thr Leu Val Glu Glu Leu Glu Ser Gln Arg Lys Cys Pro
705                 710                 715                 720

Pro Cys Trp Tyr Lys Phe Ala Asn Thr Phe Leu Ile Trp Glu Cys His
                725                 730                 735

Pro Tyr Trp Ile Lys Leu Lys Glu Ile Val Asn Leu Ile Val Met Asp
                740                 745                 750

Pro Phe Val Asp Leu Ala Ile Thr Ile Cys Ile Val Leu Asn Thr Leu
            755                 760                 765

Phe Met Ala Met Glu His His Pro Met Thr Pro Gln Phe Glu His Val
770                 775                 780

Leu Ala Val Gly Asn Leu Val Phe Thr Gly Ile Phe Thr Ala Glu Met
785                 790                 795                 800

Phe Leu Lys Leu Ile Ala Met Asp Pro Tyr Tyr Tyr Phe Gln Glu Gly
                805                 810                 815

Trp Asn Ile Phe Asp Gly Phe Ile Val Ser Leu Ser Leu Met Glu Leu
                820                 825                 830

Ser Leu Ala Asp Val Glu Gly Leu Ser Val Leu Arg Ser Phe Arg Leu
                835                 840                 845

Leu Arg Val Phe Lys Leu Ala Lys Ser Trp Pro Thr Leu Asn Met Leu
            850                 855                 860

Ile Lys Ile Ile Gly Asn Ser Val Gly Ala Leu Gly Asn Leu Thr Leu
865                 870                 875                 880

Val Leu Ala Ile Ile Val Phe Ile Phe Ala Val Val Gly Met Gln Leu
                885                 890                 895

Phe Gly Lys Ser Tyr Lys Glu Cys Val Cys Lys Ile Asn Gln Asp Cys
            900                 905                 910

Glu Leu Pro Arg Trp His Met His Asp Phe Phe His Ser Phe Leu Ile
            915                 920                 925

Val Phe Arg Val Leu Cys Gly Glu Trp Ile Glu Thr Met Trp Asp Cys
        930                 935                 940

Met Glu Val Ala Gly Gln Ala Met Cys Leu Ile Val Phe Met Met Val
945                 950                 955                 960

Met Val Ile Gly Asn Leu Val Val Leu Asn Leu Phe Leu Ala Leu Leu
                965                 970                 975

Leu Ser Ser Phe Ser Ala Asp Asn Leu Ala Ala Thr Asp Asp Gly
            980                 985                 990

Glu Met Asn Asn Leu Gln Ile Ser Val Ile Arg Ile Lys Lys Gly Val
            995                 1000                1005

Ala Trp Thr Lys Leu Lys Val His Ala Phe Met Gln Ala His Phe
        1010                1015                1020

Lys Gln Arg Glu Ala Asp Val Lys Pro Leu Asp Glu Leu Tyr
        1025                1030                1035

Glu Lys Lys Ala Asn Cys Ile Ala Asn His Thr Gly Ala Asp Ile
        1040                1045                1050

-continued

```
His Arg Asn Gly Asp Phe Gln Lys Asn Gly Asn Gly Thr Thr Ser
1055                1060                1065

Gly Ile Gly Ser Ser Val Glu Lys Tyr Ile Ile Asp Glu Asp His
1070                1075                1080

Met Ser Phe Ile Asn Asn Pro Asn Leu Thr Val Arg Val Pro Ile
1085                1090                1095

Ala Val Gly Glu Ser Asp Phe Glu Asn Leu Asn Thr Glu Asp Val
1100                1105                1110

Ser Ser Glu Ser Asp Pro Glu Gly Ser Lys Asp Lys Leu Asp Asp
1115                1120                1125

Thr Ser Ser Ser Glu Gly Ser Thr Ile Asp Ile Lys Pro Glu Val
1130                1135                1140

Glu Glu Val Pro Val Glu Gln Pro Glu Glu Tyr Leu Asp Pro Asp
1145                1150                1155

Ala Cys Phe Thr Glu Gly Cys Val Gln Arg Phe Lys Cys Cys Gln
1160                1165                1170

Val Asn Ile Glu Glu Gly Leu Gly Lys Ser Trp Trp Ile Leu Arg
1175                1180                1185

Lys Thr Cys Phe Leu Ile Val Glu His Asn Trp Phe Glu Thr Phe
1190                1195                1200

Ile Ile Phe Met Ile Leu Leu Ser Ser Gly Ala Leu Ala Phe Glu
1205                1210                1215

Asp Ile Tyr Ile Glu Gln Arg Lys Thr Ile Arg Thr Ile Leu Glu
1220                1225                1230

Tyr Ala Asp Lys Val Phe Thr Tyr Ile Phe Ile Leu Glu Met Leu
1235                1240                1245

Leu Lys Trp Thr Ala Tyr Gly Phe Val Lys Phe Thr Asn Ala
1250                1255                1260

Trp Cys Trp Leu Asp Phe Leu Ile Val Ala Val Ser Leu Val Ser
1265                1270                1275

Leu Ile Ala Asn Ala Leu Gly Tyr Ser Glu Leu Gly Ala Ile Lys
1280                1285                1290

Ser Leu Arg Thr Leu Arg Ala Leu Arg Pro Leu Arg Ala Leu Ser
1295                1300                1305

Arg Phe Glu Gly Met Arg Val Val Val Asn Ala Leu Val Gly Ala
1310                1315                1320

Ile Pro Ser Ile Met Asn Val Leu Leu Val Cys Leu Ile Phe Trp
1325                1330                1335

Leu Ile Phe Ser Ile Met Gly Val Asn Leu Phe Ala Gly Lys Tyr
1340                1345                1350

His Tyr Cys Phe Asn Glu Thr Ser Glu Ile Arg Phe Glu Ile Glu
1355                1360                1365

Asp Val Asn Asn Lys Thr Glu Cys Glu Lys Leu Met Glu Gly Asn
1370                1375                1380

Asn Thr Glu Ile Arg Trp Lys Asn Val Lys Ile Asn Phe Asp Asn
1385                1390                1395

Val Gly Ala Gly Tyr Leu Ala Leu Leu Gln Val Ala Thr Phe Lys
1400                1405                1410

Gly Trp Met Asp Ile Met Tyr Ala Ala Val Asp Ser Arg Lys Pro
1415                1420                1425

Asp Glu Gln Pro Lys Tyr Glu Asp Asn Ile Tyr Met Tyr Ile Tyr
1430                1435                1440

Phe Val Ile Phe Ile Ile Phe Gly Ser Phe Phe Thr Leu Asn Leu
```

-continued

```
            1445                1450                1455

Phe Ile Gly Val Ile Ile Asp Asn Phe Asn Gln Gln Lys Lys Lys
    1460                1465                1470

Phe Gly Gly Gln Asp Ile Phe Met Thr Glu Glu Gln Lys Lys Tyr
    1475                1480                1485

Tyr Asn Ala Met Lys Lys Leu Gly Ser Lys Lys Pro Gln Lys Pro
    1490                1495                1500

Ile Pro Arg Pro Leu Asn Lys Ile Gln Gly Ile Val Phe Asp Phe
    1505                1510                1515

Val Thr Gln Gln Ala Phe Asp Ile Val Ile Met Met Leu Ile Cys
    1520                1525                1530

Leu Asn Met Val Thr Met Met Val Glu Thr Asp Thr Gln Ser Lys
    1535                1540                1545

Gln Met Glu Asn Ile Leu Tyr Trp Ile Asn Leu Val Phe Val Ile
    1550                1555                1560

Phe Phe Thr Cys Glu Cys Val Leu Lys Met Phe Ala Leu Arg His
    1565                1570                1575

Tyr Tyr Phe Thr Ile Gly Trp Asn Ile Phe Asp Phe Val Val Val
    1580                1585                1590

Ile Leu Ser Ile Val Gly Met Phe Leu Ala Asp Ile Ile Glu Lys
    1595                1600                1605

Tyr Phe Val Ser Pro Thr Leu Phe Arg Val Ile Arg Leu Ala Arg
    1610                1615                1620

Ile Gly Arg Ile Leu Arg Leu Ile Lys Gly Ala Lys Gly Ile Arg
    1625                1630                1635

Thr Leu Leu Phe Ala Leu Met Met Ser Leu Pro Ala Leu Phe Asn
    1640                1645                1650

Ile Gly Leu Leu Leu Phe Leu Val Met Phe Ile Phe Ser Ile Phe
    1655                1660                1665

Gly Met Ser Asn Phe Ala Tyr Val Lys His Glu Ala Gly Ile Asp
    1670                1675                1680

Asp Met Phe Asn Phe Glu Thr Phe Gly Asn Ser Met Ile Cys Leu
    1685                1690                1695

Phe Gln Ile Thr Thr Ser Ala Gly Trp Asp Gly Leu Leu Leu Pro
    1700                1705                1710

Ile Leu Asn Arg Pro Pro Asp Cys Ser Leu Asp Lys Glu His Pro
    1715                1720                1725

Gly Ser Gly Phe Lys Gly Asp Cys Gly Asn Pro Ser Val Gly Ile
    1730                1735                1740

Phe Phe Phe Val Ser Tyr Ile Ile Ile Ser Phe Leu Ile Val Val
    1745                1750                1755

Asn Met Tyr Ile Ala Ile Ile Leu Glu Asn Phe Ser Val Ala Thr
    1760                1765                1770

Glu Glu Ser Ala Asp Pro Leu Ser Glu Asp Asp Phe Glu Thr Phe
    1775                1780                1785

Tyr Glu Ile Trp Glu Lys Phe Asp Pro Asp Ala Thr Gln Phe Ile
    1790                1795                1800

Glu Tyr Cys Lys Leu Ala Asp Phe Ala Asp Ala Leu Glu His Pro
    1805                1810                1815

Leu Arg Val Pro Lys Pro Asn Thr Ile Glu Leu Ile Ala Met Asp
    1820                1825                1830

Leu Pro Met Val Ser Gly Asp Arg Ile His Cys Leu Asp Ile Leu
    1835                1840                1845
```

```
Phe Ala Phe Thr Lys Arg Val Leu Gly Asp Ser Gly Glu Leu Asp
    1850                1855                1860

Ile Leu Arg Gln Gln Met Glu Glu Arg Phe Val Ala Ser Asn Pro
    1865                1870                1875

Ser Lys Val Ser Tyr Glu Pro Ile Thr Thr Thr Leu Arg Arg Lys
    1880                1885                1890

Gln Glu Glu Val Ser Ala Val Val Leu Gln Arg Ala Tyr Arg Gly
    1895                1900                1905

His Leu Ala Arg Arg Gly Phe Ile Cys Lys Lys Thr Thr Ser Asn
    1910                1915                1920

Lys Leu Glu Asn Gly Gly Thr His Arg Glu Lys Lys Glu Ser Thr
    1925                1930                1935

Pro Ser Thr Ala Ser Leu Pro Ser Tyr Asp Ser Val Thr Lys Pro
    1940                1945                1950

Glu Lys Glu Lys Gln Gln Arg Ala Glu Glu Gly Arg Arg Glu Arg
    1955                1960                1965

Ala Lys Arg Gln Lys Glu Val Arg Glu Ser Lys Cys
    1970                1975                1980

<210> SEQ ID NO 7
<211> LENGTH: 33
<212> TYPE: DNA
<213> ORGANISM: artificial sequence
<220> FEATURE:
<223> OTHER INFORMATION: primer sequence
<220> FEATURE:
<221> NAME/KEY: misc_feature
<222> LOCATION: (10)..(10)
<223> OTHER INFORMATION: C/T
<220> FEATURE:
<221> NAME/KEY: misc_feature
<222> LOCATION: (14)..(14)
<223> OTHER INFORMATION: C/T
<220> FEATURE:
<221> NAME/KEY: misc_feature
<222> LOCATION: (16)..(16)
<223> OTHER INFORMATION: inosine
<220> FEATURE:
<221> NAME/KEY: misc_feature
<222> LOCATION: (19)..(19)
<223> OTHER INFORMATION: inosine
<220> FEATURE:
<221> NAME/KEY: misc_feature
<222> LOCATION: (22)..(22)
<223> OTHER INFORMATION: C/T
<220> FEATURE:
<221> NAME/KEY: misc_feature
<222> LOCATION: (23)..(23)
<223> OTHER INFORMATION: inosine
<220> FEATURE:
<221> NAME/KEY: misc_feature
<222> LOCATION: (24)..(24)
<223> OTHER INFORMATION: any base
<220> FEATURE:
<221> NAME/KEY: misc_feature
<222> LOCATION: (25)..(25)
<223> OTHER INFORMATION: A, T or C
<220> FEATURE:
<221> NAME/KEY: misc_feature
<222> LOCATION: (28)..(28)
<223> OTHER INFORMATION: A, T or C
<220> FEATURE:
<221> NAME/KEY: misc_feature
<222> LOCATION: (25)..(25)
<223> OTHER INFORMATION: insine

<400> SEQUENCE: 7
gcgaagcttn tggntnatnt tnnnnatnat ggg                          33
```

<210> SEQ ID NO 8
<211> LENGTH: 28
<212> TYPE: DNA
<213> ORGANISM: artificial sequence
<220> FEATURE:
<223> OTHER INFORMATION: primer sequence
<220> FEATURE:
<221> NAME/KEY: misc_feature
<222> LOCATION: (15)..(15)
<223> OTHER INFORMATION: any base
<220> FEATURE:
<221> NAME/KEY: misc_feature
<222> LOCATION: (11)..(11)
<223> OTHER INFORMATION: inosine
<220> FEATURE:
<221> NAME/KEY: misc_feature
<222> LOCATION: (14)..(14)
<223> OTHER INFORMATION: inosine
<220> FEATURE:
<221> NAME/KEY: misc_feature
<222> LOCATION: (16)..(16)
<223> OTHER INFORMATION: inosine
<220> FEATURE:
<221> NAME/KEY: misc_feature
<222> LOCATION: (20)..(20)
<223> OTHER INFORMATION: inosine
<220> FEATURE:
<221> NAME/KEY: misc_feature
<222> LOCATION: (17)..(17)
<223> OTHER INFORMATION: A/G
<220> FEATURE:
<221> NAME/KEY: misc_feature
<222> LOCATION: (23)..(23)
<223> OTHER INFORMATION: any base
<220> FEATURE:
<221> NAME/KEY: misc_feature
<222> LOCATION: (26)..(26)
<223> OTHER INFORMATION: C/T

<400> SEQUENCE: 8
ataggatcca nccnnnnaan gcnacntg                                28

<210> SEQ ID NO 9
<211> LENGTH: 20
<212> TYPE: DNA
<213> ORGANISM: artificial sequence
<220> FEATURE:
<223> OTHER INFORMATION: primer sequence

<400> SEQUENCE: 9
tacaattctc cggtcaagtt                                         20

<210> SEQ ID NO 10
<211> LENGTH: 20
<212> TYPE: DNA
<213> ORGANISM: artificial sequence
<220> FEATURE:
<223> OTHER INFORMATION: primer sequence

<400> SEQUENCE: 10
atgttagtca aaatgtgcga                                         20

<210> SEQ ID NO 11
<211> LENGTH: 20
<212> TYPE: DNA
<213> ORGANISM: artificial sequence
<220> FEATURE:
<223> OTHER INFORMATION: primer sequence

<400> SEQUENCE: 11
catcctcacc aactgcgtgt                                           20

<210> SEQ ID NO 12
<211> LENGTH: 20
<212> TYPE: DNA
<213> ORGANISM: artificial sequence
<220> FEATURE:
<223> OTHER INFORMATION: primer sequence

<400> SEQUENCE: 12
cactgaggta aaggtccagg                                           20

<210> SEQ ID NO 13
<211> LENGTH: 20
<212> TYPE: DNA
<213> ORGANISM: artificial sequence
<220> FEATURE:
<223> OTHER INFORMATION: primer sequence

<400> SEQUENCE: 13
agaccatccg caccatcctg                                           20

<210> SEQ ID NO 14
<211> LENGTH: 20
<212> TYPE: DNA
<213> ORGANISM: artificial sequence
<220> FEATURE:
<223> OTHER INFORMATION: primer sequence

<400> SEQUENCE: 14
tgtcaaagtt gatcttcacg                                           20

<210> SEQ ID NO 15
<211> LENGTH: 20
<212> TYPE: DNA
<213> ORGANISM: artificial sequence
<220> FEATURE:
<223> OTHER INFORMATION: primer sequence

<400> SEQUENCE: 15
tatgaccatg aataacccgc                                           20

<210> SEQ ID NO 16
<211> LENGTH: 20
<212> TYPE: DNA
<213> ORGANISM: artificial sequence
<220> FEATURE:
<223> OTHER INFORMATION: primer sequence

<400> SEQUENCE: 16
tcaggtttcc catgaacagc                                           20

<210> SEQ ID NO 17
<211> LENGTH: 20
<212> TYPE: DNA
<213> ORGANISM: artificial sequence
<220> FEATURE:
<223> OTHER INFORMATION: primer sequence

<400> SEQUENCE: 17
tatacaccca tctccagcga                                           20

<210> SEQ ID NO 18
<211> LENGTH: 20
<212> TYPE: DNA
<213> ORGANISM: artificial sequence

```
<220> FEATURE:
<223> OTHER INFORMATION: primer sequence

<400> SEQUENCE: 18
catctcctca ttcacgaagc                                              20

<210> SEQ ID NO 19
<211> LENGTH: 20
<212> TYPE: DNA
<213> ORGANISM: artificial sequence
<220> FEATURE:
<223> OTHER INFORMATION: primer sequence

<400> SEQUENCE: 19
ctgctggtct tcttgcttgt                                              20

<210> SEQ ID NO 20
<211> LENGTH: 20
<212> TYPE: DNA
<213> ORGANISM: artificial sequence
<220> FEATURE:
<223> OTHER INFORMATION: primer sequence

<400> SEQUENCE: 20
gctgttctcc tcatcctctt                                              20

<210> SEQ ID NO 21
<211> LENGTH: 20
<212> TYPE: DNA
<213> ORGANISM: artificial sequence
<220> FEATURE:
<223> OTHER INFORMATION: primer sequence

<400> SEQUENCE: 21
aaccctattc cgagtcatcc                                              20

<210> SEQ ID NO 22
<211> LENGTH: 20
<212> TYPE: DNA
<213> ORGANISM: artificial sequence
<220> FEATURE:
<223> OTHER INFORMATION: primer sequence

<400> SEQUENCE: 22
tgcactttcc tctgtggcta                                              20

<210> SEQ ID NO 23
<211> LENGTH: 20
<212> TYPE: DNA
<213> ORGANISM: artificial sequence
<220> FEATURE:
<223> OTHER INFORMATION: primer sequence

<400> SEQUENCE: 23
aaggaagaca aagggaaaga                                              20

<210> SEQ ID NO 24
<211> LENGTH: 20
<212> TYPE: DNA
<213> ORGANISM: artificial sequence
<220> FEATURE:
<223> OTHER INFORMATION: primer sequence

<400> SEQUENCE: 24
tcctgtgaaa agatgacaag                                              20
```

<210> SEQ ID NO 25
<211> LENGTH: 1012
<212> TYPE: DNA
<213> ORGANISM: Homo sapiens

<400> SEQUENCE: 25

| | | | | | |
|---|---|---|---|---|---|
| gagcgcggcg | cgggccacca | tgggggccca | gctcagcacg | ttgggccata | tggtgctctt | 60 |
| cccagtctgg | ttcctgtaca | gtctgctcat | gaagctgttc | cagcgctcca | cgccagccat | 120 |
| caccctcgag | agcccggaca | tcaagtaccc | gctgcggctc | atcgaccggg | agatcatcag | 180 |
| ccatgacacc | cggcgcttcc | gctttgccct | gccgtcaccc | cagcacatcc | tgggcctccc | 240 |
| tgtcggccag | cacatctacc | tctcggctcg | aattgatgga | aacctggtcg | tccggcccta | 300 |
| tacacccatc | tccagcgatg | atgacaaggg | cttcgtggac | ctggtcatca | aggtttactt | 360 |
| caaggacacc | catcccaagt | tcccgctggg | agggaagatg | tctcagtacc | tggagagcat | 420 |
| gcagattgga | gacaccattg | agttccgggg | ccccagtggg | ctgctggtct | accagggcaa | 480 |
| agggaagttc | gccatccgac | ctgacaaaaa | gtccaaccct | atcatcagga | cagtgaagtc | 540 |
| tgtgggcatg | atcgcgggag | ggacaggcat | caccccgatg | ctgcaggtga | tccgcgccat | 600 |
| catgaaggac | cctgatgacc | acactgtgtg | ccacctgctc | tttgccaacc | agaccgagaa | 660 |
| ggacatcctg | ctgcgacctg | agctggagga | actcaggaac | aaacattctg | cacgcttcaa | 720 |
| gctctggtac | acgctggaca | gagcccctga | agcctgggac | tacggccagg | gcttcgtgaa | 780 |
| tgaggagatg | atccgggacc | accttccacc | cccagaggag | gagccgctgg | tgctgatgtg | 840 |
| tggccccca | cccatgatcc | agtacgcctg | ccttcccaac | ctggaccacg | tgggccaccc | 900 |
| cacggagcgc | tgcttcgtct | ctgagggcc | gggcaccggt | cacacggcca | ccgcccccgc | 960 |
| gcaccccacg | ccctgttcac | gctcacccag | tcacctcccc | acatcgcaca | ct | 1012 |

<210> SEQ ID NO 26
<211> LENGTH: 349
<212> TYPE: DNA
<213> ORGANISM: Homo sapiens

<400> SEQUENCE: 26

| | | | | | |
|---|---|---|---|---|---|
| cggactggac | caaaaatgtc | gagtacactt | ttactggaat | atatactttt | gaatcacttg | 60 |
| taaaaatcct | tgcaagaggc | ttctgtgtag | gagaattcac | ttttcttcgt | gacccgtgga | 120 |
| actggctgga | ttttgtcgtc | attgtttttg | cgtatttaac | agaatttgta | aacctaggca | 180 |
| atgtttcagc | tcttcgaact | ttcagagtat | tgagagcttt | gaaaactatt | tctgtaatcc | 240 |
| caggcctgaa | gacaattgta | ggggctttga | tccagtcagt | gaagaagctt | tctgatgtca | 300 |
| tgatcctgac | tgtgttctgt | ctgagtgtgt | ttgcactaat | tggactaca | | 349 |

<210> SEQ ID NO 27
<211> LENGTH: 349
<212> TYPE: DNA
<213> ORGANISM: Homo sapiens

<400> SEQUENCE: 27

| | | | | | |
|---|---|---|---|---|---|
| cggactggac | caaaaatgtc | gagtacactt | ttactggaat | atatactttt | gaatcacttg | 60 |
| taaaaatcct | tgcaagaggc | ttctgtgtag | gagaattcac | ttttcttcgt | gacccgtgga | 120 |
| actggctgga | ttttgtcgtc | attgtttttg | cgtatttaac | agaatttgta | aacctaggca | 180 |
| atgtttcagc | tcttcgaact | ttcagagtat | tgagagcttt | gaaaactatt | tctgtaatcc | 240 |
| caggcctgaa | gacaattgta | ggggctttga | tccagtcagt | gaagaagctt | tctgatgtca | 300 |

```
tgatcctgac tgtgttctgt ctgagtgtgt ttgcactaat tggactaca         349

<210> SEQ ID NO 28
<211> LENGTH: 423
<212> TYPE: DNA
<213> ORGANISM: Homo sapiens

<400> SEQUENCE: 28
gaatatgctg acaaagtctt cacctatatc ttcatcctgg agatgttgct caagtggaca    60
gcctatggct tcgtcaagtt cttcaccaat gcctggtgtt ggctggactt cctcattgtg   120
gctgtaccat taaatttgtc tggcttaatt taatggggac ttctgggacc tgcagagact   180
gtaaagggcg agggtggtgg tgaatgcctt ggtgggcgcc atcccctcca tcatgaatgt   240
gctgctggtg tgtctcatct tctggctgat tttcagcatc atgggagtta acttgtttgc   300
gggaaagtac cactactgct ttaatgagac ttctgaaatc cgatttgaaa ttgaagatgt   360
caacaataaa actgaatgtg aaaagcttat ggaggggaac aatacagaga tcagatggaa   420
gaa                                                                423

<210> SEQ ID NO 29
<211> LENGTH: 423
<212> TYPE: DNA
<213> ORGANISM: Homo sapiens

<400> SEQUENCE: 29
gaatatgctg acaaagtctt cacctatatc ttcatcctgg agatgttgct caagtggaca    60
gcctatggct tcgtcaagtt cttcaccaat gcctggtgtt ggctggactt cctcattgtg   120
gctgtaccat taaatttgtc tggcttaatt taatggggac ttctgggacc tgcagagact   180
gtaaagggcg agggtggtgg tgaatgcctt ggtgggcgcc atcccctcca tcatgaatgt   240
gctgctggtg tgtctcatct tctggctgat tttcagcatc atgggagtta acttgtttgc   300
gggaaagtac cactactgct ttaatgagac ttctgaaatc cgatttgaaa ttgaagatgt   360
caacaataaa actgaatgtg aaaagcttat ggaggggaac aatacagaga tcagatggaa   420
gaa                                                                423

<210> SEQ ID NO 30
<211> LENGTH: 469
<212> TYPE: DNA
<213> ORGANISM: Homo sapiens

<400> SEQUENCE: 30
tcatggccca gcacgaccct ccaccctgga ccaagtatgt cgagtacacc ttcaccgcca    60
tttacccttt tgagtctctg gtcaagattc tggctcgagg cttctgcctg cacgcgttca   120
ctttccttcg ggacccatgg aactggctgg actttagtgt gattatcatg gcgtatgtat   180
cagaaaatat aaaactaggc aatttgtcgg ctcttcgaac tttcagagtc ctgagagctc   240
taaaaactat ttcagttatc ccagggctga agaccatcgt gggggccctg atccagtctg   300
tgaagaagct ggctgatgtg atggtcctca cagtcttctg cctcagcgtc tttgccctca   360
tcggcctgca gctcttcatg ggcaacctaa ggcacaagtg cgtgcgcaac ttcacagcgc   420
tcaacggcac caacggctcc gtggaggccg acggcttggt ctgggaatc                469

<210> SEQ ID NO 31
<211> LENGTH: 469
<212> TYPE: DNA
```

```
<213> ORGANISM: Homo sapiens

<400> SEQUENCE: 31
tcatggccca gcacgaccct ccaccctgga ccaagtatgt cgagtacacc ttcaccgcca      60
tttacacctt tgagtctctg gtcaagattc tggctcgagg cttctgcctg cacgcgttca     120
ctttccttcg ggacccatgg aactggctgg actttagtgt gattatcatg gcgtatgtat     180
cagaaaatat aaaactaggc aatttgtcgg ctcttcgaac tttcagagtc ctgagagctc     240
taaaaactat ttcagttatc ccagggctga agaccatcgt gggggccctg atccagtctg     300
tgaagaagct ggctgatgtg atggtcctca cagtcttctg cctcagcgtc tttgccctca     360
tcggcctgca gctcttcatg ggcaacctaa ggcacaagtg cgtgcgcaac ttcacagcgc     420
tcaacggcac caacggctcc gtggaggccg acggcttggt ctgggaatc                 469

<210> SEQ ID NO 32
<211> LENGTH: 469
<212> TYPE: DNA
<213> ORGANISM: Homo sapiens

<400> SEQUENCE: 32
tcatggccca gcacgaccct ccaccctgga ccaagtatgt cgagtacacc ttcaccgcca      60
tttacacctt tgagtctctg gtcaagattc tggctcgagg cttctgcctg cacgcgttca     120
ctttccttcg ggacccatgg aactggctgg actttagtgt gattatcatg gcgtatgtat     180
cagaaaatat aaaactaggc aatttgtcgg ctcttcgaac tttcagagtc ctgagagctc     240
taaaaactat ttcagttatc ccagggctga agaccatcgt gggggccctg atccagtctg     300
tgaagaagct ggctgatgtg atggtcctca cagtcttctg cctcagcgtc tttgccctca     360
tcggcctgca gctcttcatg ggcaacctaa ggcacaagtg cgtgcgcaac ttcacagcgc     420
tcaacggcac caacggctcc gtggaggccg acggcttggt ctgggaatc                 469

<210> SEQ ID NO 33
<211> LENGTH: 469
<212> TYPE: DNA
<213> ORGANISM: Homo sapiens

<400> SEQUENCE: 33
tcatggccca gcacgaccct ccaccctgga ccaagtatgt cgagtacacc ttcaccgcca      60
tttacacctt tgagtctctg gtcaagattc tggctcgagg cttctgcctg cacgcgttca     120
ctttccttcg ggacccatgg aactggctgg actttagtgt gattatcatg gcgtatgtat     180
cagaaaatat aaaactaggc aatttgtcgg ctcttcgaac tttcagagtc ctgagagctc     240
taaaaactat ttcagttatc ccagggctga agaccatcgt gggggccctg atccagtctg     300
tgaagaagct ggctgatgtg atggtcctca cagtcttctg cctcagcgtc tttgccctca     360
tcggcctgca gctcttcatg ggcaacctaa ggcacaagtg cgtgcgcaac ttcacagcgc     420
tcaacggcac caacggctcc gtggaggccg acggcttggt ctgggaatc                 469

<210> SEQ ID NO 34
<211> LENGTH: 469
<212> TYPE: DNA
<213> ORGANISM: Homo sapiens

<400> SEQUENCE: 34
tcatggccca gcacgaccct ccaccctgga ccaagtatgt cgagtacacc ttcaccgcca      60
tttacacctt tgagtctctg gtcaagattc tggctcgagg cttctgcctg cacgcgttca     120
```

```
ctttccttcg ggacccatgg aactggctgg actttagtgt gattatcatg gcatacacaa    180
ctgaatttgt ggacctgggc aatgtctcag ccttacgcac cttccgagtc ctccgggccc    240
tgaaaactat atcagtcatt tcagggctga agaccatcgt gggggccctg atccagtctg    300
tgaagaagct ggctgatgtg atggtcctca cagtcttctg cctcagcgtc tttgccctca    360
tcggcctgca gctcttcatg ggcaacctaa ggcacaagtg cgtgcgcaac ttcacagcgc    420
tcaacggcac caacggctcc gtggaggccg acggcttggt ctgggaatc                469

<210> SEQ ID NO 35
<211> LENGTH: 469
<212> TYPE: DNA
<213> ORGANISM: Homo sapiens

<400> SEQUENCE: 35
tcatggccca gcacgaccct ccaccctgga ccaagtatgt cgagtacacc ttcaccgcca     60
tttacacctt tgagtctctg gtcaagattc tggctcgagg cttctgcctg cacgcgttca    120
ctttccttcg ggacccatgg aactggctgg actttagtgt gattatcatg gcatacacaa    180
ctgaatttgt ggacctgggc aatgtctcag ccttacgcac cttccgagtc ctccgggccc    240
tgaaaactat atcagtcatt tcagggctga agaccatcgt gggggccctg atccagtctg    300
tgaagaagct ggctgatgtg atggtcctca cagtcttctg cctcagcgtc tttgccctca    360
tcggcctgca gctcttcatg ggcaacctaa ggcacaagtg cgtgcgcaac ttcacagcgc    420
tcaacggcac caacggctcc gtggaggccg acggcttggt ctgggaatc                469

<210> SEQ ID NO 36
<211> LENGTH: 469
<212> TYPE: DNA
<213> ORGANISM: Homo sapiens

<400> SEQUENCE: 36
tcatggccca gcacgaccct ccaccctgga ccaagtatgt cgagtacacc ttcaccgcca     60
tttacacctt tgagtctctg gtcaagattc tagctcgagg cttctgcctg cacgcgttca    120
ctttccttcg ggacccatgg aactggctgg actttagtgt gattatcatg gcgtatgtat    180
cagaaaatat aaaactaggc aatttgtcgg ctcttcgaac tttcagagtc ctgagagctc    240
taaaaactat ttcagttatc ccagggctga agaccatcgt gggggccctg atccagtctg    300
tgaagaagct ggctgatgtg atggtcctca cagtcttctg cctcagcgtc tttgccctca    360
tcggcctgca gctcttcatg ggcaacctaa ggcacaagtg cgtgcgcaac ttcacagcgc    420
tcaacggcac caacggctcc gtggaggccg acggcttggt ctgggaatc                469

<210> SEQ ID NO 37
<211> LENGTH: 340
<212> TYPE: DNA
<213> ORGANISM: Homo sapiens

<400> SEQUENCE: 37
tcatggccca gcacgaccct ccaccctgga ccaagtatgt cgagtatgta tcagaaaata     60
taaaactagg caatttgtcg gctcttcgaa ctttcagagt cctgagagct ctaaaaacta    120
tttcagttat cccagggctg aagaccatcg tgggggccct gatccagtct gtgaagaagc    180
tggctgatgt gatggtcctc acagtcttct gcctcagcgt ctttgccctc atcggcctgc    240
agctcttcat gggcaaccta aggcacaagt gcgtgcgcaa cttcacagcg ctcaacggca    300
```

```
ccaacggctc cgtggaggcc gacggcttgg tctgggaatc                              340
```

<210> SEQ ID NO 38
<211> LENGTH: 467
<212> TYPE: DNA
<213> ORGANISM: Homo sapiens

<400> SEQUENCE: 38

```
tcatgcccag cacgaccctc caccctggac caagtatgtc gagtacacct tcaccgccat         60
ttacaccttt gagtctctgg tcaagattct ggctcgaggc ttctgcctgc acgcgttcac        120
tttcttcggg acccatggaa ctggctggac tttagtgtga ttatcatggc gtatgtatca        180
gaaaatataa aactaggcaa tttgtcggct cttcgaactt tcagagtcct gagagctcta        240
aaaactattt cagttatccc agggctgaag accatcgtgg gggccctgat ccagtctgtg        300
aagaagctgg ctgatgtgat ggtcctcaca gtcttctgcc tcagcgtctt tgccctcatc        360
ggcctgcagc tcttcatggg caacctaagg cacaagtgcg tgcgcaactt cacagcgctc        420
aacggcacca acggctccgt ggaggccgac ggcttggtct gggaatc                      467
```

<210> SEQ ID NO 39
<211> LENGTH: 468
<212> TYPE: DNA
<213> ORGANISM: Homo sapiens

<400> SEQUENCE: 39

```
tcatggccca gcacgaccct ccacccggga ccaagtatgt cgagtacacc ttcaccgcca         60
tttacacctt tgagtctctg gtcaagattc tagctcgagg cttctgcctg cacgcgttca        120
ctttcttcgg gacccatgga actggctgga ctttagtgtg attatcatgg cgtatgtatc        180
agaaaatata aaactaggca atttgtcggc tcttcgaact ttcagagtcc tgagagctct        240
aaaaactatt tcagttatcc cagggctgaa gaccatcgtg ggggccctga tccagtctgt        300
gaagaagctg gctgatgtga tggtcctcac agtcttctgc ctcagcgtct ttgccctcat        360
cggcctgcag ctcttcatgg gcaacctaag gcacaagtgc gtgcgcaact tcatagcgct        420
caacggcacc aacggctccg tggaggccga cggcttggtc tgggaatc                     468
```

<210> SEQ ID NO 40
<211> LENGTH: 184
<212> TYPE: DNA
<213> ORGANISM: Homo sapiens

<400> SEQUENCE: 40

```
cgtgaacctc tttgcgggga agtttgggag gtgcatcaac cagacagagg gagacttgcc         60
tttgaactac accatcgtga caacaagag ccagtgtgag tccttgaact tgaccggaga         120
attgtactgg accaaggtga agtcaacttt gacaacgtg ggggccgggt acctggccct         180
tctg                                                                    184
```

<210> SEQ ID NO 41
<211> LENGTH: 184
<212> TYPE: DNA
<213> ORGANISM: Homo sapiens

<400> SEQUENCE: 41

```
agtaaatttg tttgctggca agttctatga gtgtattaac accacagatg ggtcacggtt         60
tcctgcaagt caagttccaa atcgttccga atgttttgcc cttatgaatg ttagtcaaaa        120
tgtgcgatgg aaaaacctga agtgaacttt tgataatgtc ggacttggtt acctatctct        180
```

```
gctt                                                                         184

<210> SEQ ID NO 42
<211> LENGTH: 187
<212> TYPE: DNA
<213> ORGANISM: Homo sapiens

<400> SEQUENCE: 42
agttaacttg tttgcgggaa agtaccacta ctgctttaat gagacttctg aaatccgatt            60
tgaaattgaa gatgtcaaca ataaaactga atgtgaaaag cttatggagg ggaacaatac           120
agagatcaga tggaagaacg tgaagatcaa ctttgacaat gttggggcag gatacctggc           180
ccttctt                                                                     187

<210> SEQ ID NO 43
<211> LENGTH: 452
<212> TYPE: DNA
<213> ORGANISM: Homo sapiens

<400> SEQUENCE: 43
tgatgacaag ggcttcgtgg acctggtcat caaggtttac ttcaaggaca cccatcccaa            60
gtttcccgct ggagggaaga tgtctcagta cctggagagc atgcagattg agacaccat           120 tgagttccgg ggccccagtg ggctgctggt ctaccagggc aaagggaagt tcgccatccg           180
acctgacaaa aagtccaacc ctatcatcag gacagtgaag tctgtgggca tgatcgcggg           240
agggacaggc atcaccccga tgctgcaggt gatccgcgcc atcatgaagg accctgatga           300
ccacactgtg tgccacctgc tctttgccaa ccagaccgag aaggacatcc tgctgcgacc           360
tgagctggag gaactcagga acaaacattc tgcacgcttc aagctctggt acacgctgga           420
cagagcccct gaagcctggg actacggcca gg                                         452

<210> SEQ ID NO 44
<211> LENGTH: 452
<212> TYPE: DNA
<213> ORGANISM: Homo sapiens

<400> SEQUENCE: 44
tgatgacaag ggcttcgtgg acctggtcat caaggtttac ttcaaggaca cccatcccaa            60
gtttcccgct ggagggaaga tgtctcagta cctggagagc atgcagattg agacaccat           120 tgagttccgg ggccccagtg ggctgctggt ctaccagggc aaagggaagt tcgccatccg           180
acctgacaaa aagtccaacc ctatcatcag gacagtgaag tctgtgggca tgatcgcggg           240
agggacaggc atcaccccga tgctgcaggt gatccgcgcc atcatgaagg accctgatga           300
ccacactgtg tgccacctgc tctttgccaa ccagaccgag aaggacatcc tgctgcgacc           360
tgagctggag gaactcagga acaaacattc tgcacgcttc aagctctggt acacgctgga           420
cagagcccct gaagcctggg actacggcca gg                                         452

<210> SEQ ID NO 45
<211> LENGTH: 423
<212> TYPE: DNA
<213> ORGANISM: Homo sapiens

<400> SEQUENCE: 45
gaatatgctg acaaagtctt cacctatatc ttcatcctgg agatgttgct caagtggaca            60
gcctatggct tcgtcaagtt cttcaccaat gcctggtgtt ggctggactt cctcattgtg           120
```

```
gctgtaccat taaatttgtc tggcttaatt taatggggac ttctgggacc tgcagagact      180
gtaaagggcg agggtggtgg tgaatgcctt ggtgggcgcc atcccctcca tcatgaatgt      240
gctgctggtg tgtctcatct tctggctgat tttcagcatc atgggagtta acttgtttgc      300
gggaaagtac cactactgct ttaatgagac ttctgaaatc cgatttgaaa ttgaagatgt      360
caacaataaa actgaatgtg aaaagcttat ggagggaac aatacagaga tcagatggaa       420
gaa                                                                   423

<210> SEQ ID NO 46
<211> LENGTH: 423
<212> TYPE: DNA
<213> ORGANISM: Homo sapiens

<400> SEQUENCE: 46
gaatatgctg acaaagtctt cacctatatc ttcatcctgg agatgttgct caagtggaca       60
gcctatggct tcgtcaagtt cttcaccaat gcctggtgtt ggctggactt cctcattgtg      120
gctgtaccat taaatttgtc tggcttaatt taatggggac ttctgggacc tgcagagact      180
gtaaagggcg agggtggtgg tgaatgcctt ggtgggcgcc atcccctcca tcatgaatgt      240
gctgctggtg tgtctcatct tctggctgat tttcagcatc atgggagtta acttgtttgc      300
gggaaagtac cactactgct ttaatgagac ttctgaaatc cgatttgaaa ttgaagatgt      360
caacaataaa actgaatgtg aaaagcttat ggagggaac aatacagaga tcagatggaa       420
gaa                                                                   423

<210> SEQ ID NO 47
<211> LENGTH: 48
<212> TYPE: DNA
<213> ORGANISM: artificial sequence
<220> FEATURE:
<223> OTHER INFORMATION: consensus sequence

<400> SEQUENCE: 47
agtgagtgtg aaagtcttat ggagagcaac aaaactgtcc gatggaaa                   48

<210> SEQ ID NO 48
<211> LENGTH: 45
<212> TYPE: DNA
<213> ORGANISM: Homo sapiens

<400> SEQUENCE: 48
agtcggtgtg aaagccttct gtttaacgaa tccatgctat gggaa                      45

<210> SEQ ID NO 49
<211> LENGTH: 48
<212> TYPE: DNA
<213> ORGANISM: Homo sapiens

<400> SEQUENCE: 49
tccgaatgtt ttgcccttat gaatgttagt caaaatgtgc gatggaaa                   48

<210> SEQ ID NO 50
<211> LENGTH: 48
<212> TYPE: DNA
<213> ORGANISM: Homo sapiens

<400> SEQUENCE: 50
actgattgcc taaaactaat agaaagaaat gagactgctc gatggaaa                   48
```

```
<210> SEQ ID NO 51
<211> LENGTH: 48
<212> TYPE: DNA
<213> ORGANISM: Homo sapiens

<400> SEQUENCE: 51
agtgagtgca aagctctcat tgagagcaat caaactgcca ggtggaaa        48

<210> SEQ ID NO 52
<211> LENGTH: 39
<212> TYPE: DNA
<213> ORGANISM: Homo sapiens

<400> SEQUENCE: 52
agtgactgtc aggctcttgg caagcaagct cggtggaaa                  39

<210> SEQ ID NO 53
<211> LENGTH: 51
<212> TYPE: DNA
<213> ORGANISM: Homo sapiens

<400> SEQUENCE: 53
actgaatgtg aaaagcttat ggaggggaac aatacagaga tcagatggaa g    51

<210> SEQ ID NO 54
<211> LENGTH: 51
<212> TYPE: DNA
<213> ORGANISM: Homo sapiens

<400> SEQUENCE: 54
aacaagtctg agtgcgagag cctcatgcac acaggccagg tccgctggct c    51

<210> SEQ ID NO 55
<211> LENGTH: 51
<212> TYPE: DNA
<213> ORGANISM: Homo sapiens

<400> SEQUENCE: 55
aacaagagcc agtgtgagtc cttgaacttg accggagaat tgtactggac c    51

<210> SEQ ID NO 56
<211> LENGTH: 51
<212> TYPE: DNA
<213> ORGANISM: Rattus rattus

<400> SEQUENCE: 56
aacaagtccg agtgtcacaa tcaaaacagc accggccact tcttctgggt c    51

<210> SEQ ID NO 57
<211> LENGTH: 20
<212> TYPE: DNA
<213> ORGANISM: artificial sequence
<220> FEATURE:
<223> OTHER INFORMATION: articicial sequence

<400> SEQUENCE: 57
ttatgacaga agaacagaag                                       20

<210> SEQ ID NO 58
<211> LENGTH: 20
<212> TYPE: DNA
<213> ORGANISM: artificial sequence
<220> FEATURE:
<223> OTHER INFORMATION: artificial sequence
```

```
-continued

<400> SEQUENCE: 58
ttatgacaga agaacagaag                                               20

<210> SEQ ID NO 59
<211> LENGTH: 20
<212> TYPE: DNA
<213> ORGANISM: artificial sequence
<220> FEATURE:
<223> OTHER INFORMATION: artificial sequence

<400> SEQUENCE: 59
ttatgacgga ggaacagaag                                               20
```